(12) United States Patent
Quibell et al.

(10) Patent No.: US 12,377,084 B2
(45) Date of Patent: Aug. 5, 2025

(54) ERAP1 MODULATORS

(71) Applicant: GREY WOLF THERAPEUTICS LIMITED, Abingdon (GB)

(72) Inventors: Martin Quibell, Oxford (GB); Michael Sparenberg, Oxford (GB); Jason John Shiers, Oxford (GB)

(73) Assignee: Grey Wolf Therapeutics Limited, Abingdon (GB)

( * ) Notice: Subject to any disclaimer, the term of this patent is extended or adjusted under 35 U.S.C. 154(b) by 706 days.

(21) Appl. No.: 17/774,239

(22) PCT Filed: Nov. 12, 2020

(86) PCT No.: PCT/GB2020/052886
§ 371 (c)(1),
(2) Date: May 4, 2022

(87) PCT Pub. No.: WO2021/094763
PCT Pub. Date: May 20, 2021

(65) Prior Publication Data
US 2023/0000851 A1    Jan. 5, 2023

(30) Foreign Application Priority Data

Nov. 14, 2019 (GB) .................................... 1916597
May 22, 2020 (GB) .................................... 2007717

(51) Int. Cl.
*A61K 31/196* (2006.01)
*A61K 31/277* (2006.01)
(Continued)

(52) U.S. Cl.
CPC .......... *A61K 31/451* (2013.01); *A61K 31/196* (2013.01); *A61K 31/277* (2013.01);
(Continued)

(58) Field of Classification Search
CPC . C07C 311/21; C07C 317/34; C07C 2601/02; C07C 2601/14; C07D 207/09;
(Continued)

(56) References Cited

FOREIGN PATENT DOCUMENTS

| WO | WO-2005092845 A1 * | 10/2005 | ........... C07C 311/21 |
|---|---|---|---|
| WO | 2020104822 A1 | 5/2020 | |

OTHER PUBLICATIONS

Maben et al. J. Med. Chem. 2020, 63, 103 (Year: 2019).*
International Search Report and Written Opinion corresponding to International Patent Application No. PCT/GB2020/052886, mailed Feb. 1, 2021.
Pubchem Compounds: "4-Methoxy-3-{[2-(piperidin-1-yl)-5-(trifluoromethyl)phenyl]sulfamoyl}benzioc acid", N.C.B.I., Jul. 19, 2005 (Jul. 19, 2005), XP055659781, Retrieved from the Internet: URL: https://pubchem.ncbi.nlm.nih.gov/compound/4798291- [retrieved on Jan. 21, 2020].
N.C.B.I. Bioassay Record: "MLPCN ERAP1 Measured in Biochemical System Using Plate Reader—7016-01_Inhibitor_Dose_CherryPick_Activity", PubChem AID: 743317, Mar. 17, 2014 (Mar. 17, 2014), XP55659774, Retrieved from the Internet: URL:https://pubchem.ncbi.nlm.nih.gov/bioassay/743317 [retrieved on Jan. 21, 2020].

(Continued)

*Primary Examiner* — Amanda L. Aguirre
(74) *Attorney, Agent, or Firm* — Lathrop GPM LLP; Brian C. Trinque

(57) ABSTRACT

The present invention relates to a compound of formula (I), or a pharmaceutically acceptable salt or hydrate thereof, A compound of formula (I), or a pharmaceutically acceptable salt or hydrate thereof, (I) wherein: Z is a group of formula: (II) wherein P and Q are each independently $CR_{12}R_{13}$; or one of P and Q is $NR_{14}$ and the other is $CR_{12}R_{13}$; the group X—Y is —$NHSO_2$— or —$SO_2NH$—; $R_1$ is H, CN or alkyl; $R_2$ is selected from COOH and a tetrazolyl group; $R_3$ is selected from H, Cl and alkyl; $R_4$ is selected from H and halo; $R_5$ is selected from H, alkyl, haloalkyl, $SO_2$-alkyl, Cl, alkoxy, OH, CN, hydroxyalkyl, alkylthio, heteroaryl, cycloalkyl, heterocycloalkyl and haloalkoxy; $R_6$ is H; $R_7$ is selected from H, CN, haloalkyl, halo, $SO_2$-alkyl, heteroaryl, $SO_2NR_{16}R_{17}$, $CONR_{10}R_{11}$ and alkyl, wherein said heteroaryl group is optionally substituted by one or more substituents selected from alkyl, halo, alkoxy, CN, haloalkyl and OH; $R_8$ is selected from H, alkyl, haloalkyl and halo; $R_9$ is H or halo; and $R_{10}$, $R_{11}$, $R_{12}$, $R_{13}$, $R_{14}$, $R_{16}$ and $R_{17}$ are each independently H or alkyl; $R_{15}$ is selected from alkyl, halo, alkoxy, CN, haloalkyl and OH; and m and n are each independently 0, 1, 2 or 3. Further aspects of the invention relate to such compounds for use in the field of immune-oncology and related applications.

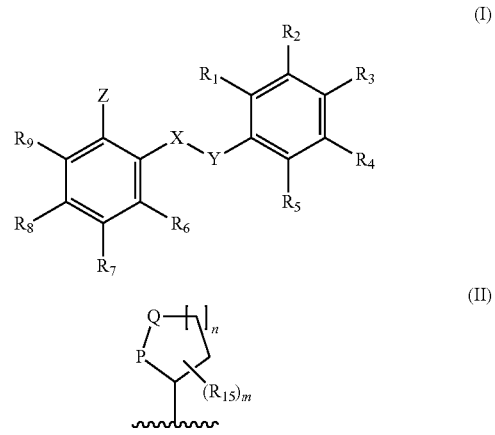

20 Claims, No Drawings

Specification includes a Sequence Listing.

(51) Int. Cl.
| | | |
|---|---|---|
| A61K 31/40 | (2006.01) | |
| A61K 31/41 | (2006.01) | |
| A61K 31/451 | (2006.01) | |
| A61K 31/454 | (2006.01) | |
| A61K 35/15 | (2025.01) | |
| A61K 39/00 | (2006.01) | |
| A61K 39/395 | (2006.01) | |
| C07C 311/21 | (2006.01) | |
| C07C 317/34 | (2006.01) | |
| C07D 207/09 | (2006.01) | |
| C07D 211/28 | (2006.01) | |
| C07D 211/34 | (2006.01) | |
| C07D 257/04 | (2006.01) | |
| C07D 401/10 | (2006.01) | |
| C07D 417/10 | (2006.01) | |

(52) U.S. Cl.
CPC ............ *A61K 31/40* (2013.01); *A61K 31/41* (2013.01); *A61K 31/454* (2013.01); *A61K 35/15* (2013.01); *A61K 39/0011* (2013.01); *A61K 39/3955* (2013.01); *C07C 311/21* (2013.01); *C07C 317/34* (2013.01); *C07D 207/09* (2013.01); *C07D 211/28* (2013.01); *C07D 211/34* (2013.01); *C07D 257/04* (2013.01); *C07D 401/10* (2013.01); *C07D 417/10* (2013.01); *A61K 2039/507* (2013.01); *A61K 2039/572* (2013.01); *A61K 2039/585* (2013.01); *C07C 2601/02* (2017.05); *C07C 2601/14* (2017.05)

(58) Field of Classification Search
CPC .. C07D 211/28; C07D 211/34; C07D 257/04; C07D 401/10; C07D 417/10; C07D 207/06; C07D 211/14; A61K 31/451; A61K 31/196; A61K 31/277; A61K 31/40; A61K 31/41; A61K 31/454; A61K 35/15; A61K 39/0011; A61K 39/3955; A61K 2039/507; A61K 2039/572; A61K 2039/585; A61P 35/00
See application file for complete search history.

(56) References Cited

OTHER PUBLICATIONS

Advanced Organic Chemistry, 3rd Edition, ed. March, J., John Wiley and Sons, New York, 1985).
Berge et al., "Pharmaceutical salts", *Journal of Pharmaceutical Sciences*, 66, 1-19 (1977).
Chen et al., "Silencing or inhibition of endoplasmic reticulum aminopeptidase 1 (ERAP1) suppresses free heavy chain expression and Th17 responses in ankylosing spondylitis", *Annals of the Rheumatic Diseases* 75:916 (2014).
Cifaldi et al., "ERAP1 Regulates Natural Killer Cell Function by Controlling the Engagement of Inhibitory Receptors", *Cancer Research* 75:824 (2015).
Conde-Jaldon et al., "Epistatic interaction of ERAP1 and HLA-B in Behçet disease: a replication study in the Spanish population", *PLoS One* 14;9(7) (2014).
Cornwell et al. "Small-Molecule Inhibition of UBE2T/FANCL-Mediated Ubiquitylation in the Fanconi Anemia Pathway". *ACS Chemical Biology* 14(10):2148-2154 (2019).
Evans et al., "Interaction between ERAP1 and HLA-B27 in ankylosing spondylitis implicates peptide handling in the mechanism for HLA-B27 in disease susceptibility", *Nature Genetics* 10:43(8):761-767 (2011).
Fingl et al., "The Pharmacological Basis of Therapeutics", Chapter 1—General Principles, p. 1-46 (1975).

Handbook of Pharmaceutical Excipients, 2nd Edition, (1994), Edited by A Wade and PJ Weller.
James et al., "Induction of Protective Antitumor Immunity through Attenuation of ERAAP Function", *Journal of Immunology* 190:5839 (2013).
Karttunen et al., "Detection of rare antigen-presenting cells by the lacZ T-cell activation assay suggests an expression cloning strategy for T-cell antigens", *PNAS USA* 89:6020-6024 (1992).
Kim et al., "Human cytomegalovirus microRNA miR-US4-1 inhibits CD8+T cell responses by targeting the aminopeptidase ERAP1", *Nature Immunology* 12:984 (2011).
Kuiper et al., "Intraocular interleukin-17 and proinflammatory cytokines in HLA-A29-associated birdshot chorioretinopathy", *American Journal of Ophthalmology* 152(2):177-182 (2011).
Kuiper et al., "Interleukin-17 production and T helper 17 cells in peripheral blood mononuclear cells in response to ocular lysate in patients with birdshot chorioretinopathy", *Molecular Vision* 19:2606-2614 (2013).
Kuiper et al., "A genome-wide association study identifies a functional ERAP2 haplotype associated with birdshot chorioretinopathy", *Human Molecular Genetics* 23(22):6081-6087 (2014).
Kuiper et al., "Functionally distinct ERAP1 and ERAP2 are a hallmark of HLA-A29-(Birdshot) Uveitis", *Human Molecular Genetics* doi: 10.1093/hmg/ddy319 (2018).
Maben, "The Relationship Between Inhibition, Conformation, and Catalysis of the Aminopeptidase ERAP1", GSBS Dissertations and Theses. https://doi.org/10.13028/hjqm-ag71. Retrieved from https://escholarship.umassmed.edu/gsbs_diss/1003 (2018).
Maben et al., "Discovery of Selective Inhibitors of Endoplasmic Reticulum Aminopeptidase 1", *Journal of Medicinal Chemistry*, 63(1):103-121 (2020).
Nagarajan et al., "ERAAP Shapes the Peptidome Associated with Classical and Nonclassical MHC Class I Molecules"; *Journal of Immunology* 197:1035 (2016).
Nicolaou et al., "Calicheamicin θ: A Rationally Designed Molecule with Extremely Potent and Selective DNA Cleaving Properties and Apoptosis Inducing Activity", Angewandte Chemie Intl. Ed. Engl., 33:183-186 (1994).
Pepelyayeva et al., "ERAP1 deficient mice have reduced Type 1 regulatory T cells and develop skeletal and intestinal features of Ankylosing Spondylitis", *Science Reports* 8:12464 (2018).
Purcell et al., "Mass spectrometry-based identification of MHC-bound peptides for immunopeptidomics", *Nature Protocols* 14:1687-1707 (2019).
Reeves et al., "Functionally distinct ERAP1 allotype combinations distinguish individuals with Ankylosing Spondylitis", *PNAS USA* 111:17594-17599 (2014).
Reeves et al., "The role of polymorphic ERAP1 in autoinflammatory disease", *Bioscience Reports* 29, p. 38 (2018).
Remington's Pharmaceutical Sciences, Mack Publishing Co. (A. R. Gennaro edit. 1985).
Search Report for GB Application No. GB1916597.6 dated Apr. 29, 2020, 5 pages.
Serwold et al., "ERAAP customizes peptides for MHC class I molecules in the endoplasmic reticulum" *Nature* 419:480 (2002).
Sheehan, "The ramifications of HLA-B27", *Journal of the Royal Society of Medicine* 97(1):10-14 (Jan. 2004).
Smith, "Update on ankylosing spondylitis: current concepts in pathogenesis", *Current Allergy and Asthma Reports* 15(1):489 (Jan. 2015).
Snyder et al., "Genetic Basis for Clinical Response to CTLA-4 Blockade in Melanoma", *The New England Journal of Medicine* 371:2189 (2014).
Steinbach et al., "ERAP1 overexpression in HPV-induced malignancies: A possible novel immune evasion mechanism", *Oncoimmunology* 6:e1336594 (2017).
Strange et al., "Genome-wide association study identifies new psoriasis susceptibility loci and an interaction between HLA-C and ERAP1", *Nature Genetics* 42(11):985-990 (2010).
Tenzer et al., "Antigen processing influences HIV-specific cytotoxic T lymphocyte immunodominance", *Nature Immunology* 10:636 (2009).

(56) References Cited

OTHER PUBLICATIONS

Van Allen et al., "Genomic correlates of response to CTLA-4 blockade in metastatic melanoma", *Science* 348:124 (2015).

* cited by examiner

ERAP1 MODULATORS

RELATED APPLICATIONS

This application is a 35 U.S.C. § 371 filing of International Application No. PCT/GB2020/052886, filed Nov. 12, 2020, which application claims priority to Great Britain Patent Application No. 2007717.8, filed May 22, 2020, and Great Britain Patent Application No. 1916597.6, filed Nov. 14, 2019.

SEQUENCE LISTING

The present application is being filed along with a Sequence Listing in computer readable format. The Sequence Listing is provided as a file entitled 728498-DYT-035US-SEQUENCE-LISTING.txt created Apr. 29, 2022 and is 1.41 bytes in size. The information in the computer readable format of the sequence listing is incorporated herein by reference in its entirety.

The present invention relates to compounds that are capable of modulating ERAP1. The compounds have potential therapeutic applications in the treatment of a variety of disorders, including proliferative, viral, immune and inflammatory disorders.

BACKGROUND TO THE INVENTION

ERAP1 (Endoplasmic Reticulum Aminopeptidase 1; also referred to as APPILS or ARTS1) is an aminopeptidase important in the generation of a proportion of antigens and neoantigens as part of the antigen presentation pathway[1]. The antigen presentation pathway starts with the breakdown of proteins by the proteasome into peptides. These peptides are transported into the endoplasmic reticulum where a proportion are processed by ERAP1 before binding to the Major Histocompatibility Complex Class I (MHC Class I)[1]. Antigens bound to MHC Class I are then transported to the surface of a cell and presented to CD8+ T-cells and recognised as either self or non-self. Neoantigens are antigens that are specific to cancer and can be recognised as foreign by the immune system leading to destruction of cancer cells. Neoantigens are created either as a direct result of somatic mutations in the DNA of cancer cells, leading to the generation of mutated proteins, or through the indirect consequences of somatic mutations on protein processing and expression. Those cancers with higher rates of mutation and correspondingly higher levels of neoantigens have much greater response rates to the checkpoint inhibitor immunotherapies anti-PD-1 (e.g. pembrolizumab, nivolumab), anti-PD-L1 (e.g. atezolizumab, avelumab, durvalumab) and anti-CTLA4 antibodies (e.g. ipilimumab, tremelimumab) compared with cancers harbouring lower numbers of neoantigens[2,3].

The role of ERAP1 in the antigen presentation pathway is to trim a proportion of peptides, via its aminopeptidase activity, to create antigens and neoantigens of the optimal length for binding to MHC Class I. ERAP1 also over-trims some neoantigens, preventing their binding to MHC Class I and presentation at the cell surface[4]. Ablation of ERAP1 activity has been shown to change the antigen and neoantigen repertoire, leading to an increase in presentation of certain antigens/neoantigens and the presentation of entirely novel antigens/neoantigens[5]. In addition, ERAP1 ablation causes CD8+ T cell dependent tumour rejection in mouse cancer models[4]. Accordingly, modulators of ERAP1 activity may be useful for cancer treatment, either used alone or in combination with current cancer immunotherapy agents, including checkpoint inhibitors, because they change the antigens and neoantigens presented on the surface of cancer cells and make them more visible to the immune system, leading to tumour attack and destruction.

Knockdown of ERAP1 is also shown to reduce the levels of regulatory-like T cells and enhance the killing of cancer cells by natural killer cells[6,7]. This suggests that modulators of ERAP1 activity might be effective cancer treatments by both modulating cancer cell visibility and creating a more anti-tumourogenic immune response. ERAP1's peptide processing role in antigen presentation is also applicable in infectious viral disease.

The present invention seeks to provide compounds that are capable of modulating ERAP1. Such compounds have potential therapeutic applications in the treatment of a variety of disorders, including proliferative disorders, immune disorders and inflammatory disorders.

Statement of Invention

A first aspect of the invention relates to a compound of formula (I), or a pharmaceutically acceptable salt or hydrate thereof,

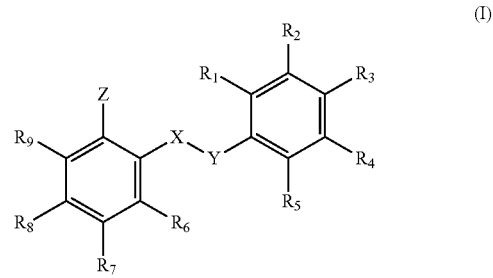

(I)

wherein:

Z is a group of formula:

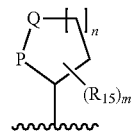

wherein P and Q are each independently $CR_{12}R_{13}$; or one of P and Q is $NR_{14}$ and the other is $CR_{12}R_{13}$;

the group X—Y is —NHSO$_2$— or —SO$_2$NH—;

$R_1$ is H, CN or alkyl;

$R_2$ is selected from COOH and a tetrazolyl group;

$R_3$ is selected from H, Cl and alkyl;

$R_4$ is selected from H and halo;

$R_5$ is selected from H, alkyl, haloalkyl, SO$_2$-alkyl, Cl, alkoxy, OH, CN, hydroxyalkyl, alkylthio, heteroaryl, cycloalkyl, heterocycloalkyl and haloalkoxy;

$R_6$ is H;

$R_7$ is selected from H, CN, haloalkyl, halo, SO$_2$-alkyl, heteroaryl, SO$_2$NR$_{16}$R$_{17}$, CONR$_{10}$R$_{11}$ and alkyl, wherein said heteroaryl group is optionally substituted by one or more substituents selected from alkyl, halo, alkoxy, CN, haloalkyl and OH;

R$_8$ is selected from H, alkyl, haloalkyl and halo;

R$_9$ is H or halo; and

R$_{10}$, R$_{11}$, R$_{12}$, R$_{13}$, R$_{14}$, R$_{16}$ and R$_{17}$ are each independently H or alkyl;

R$_{15}$ is selected from alkyl, halo, alkoxy, CN, haloalkyl and OH; and m and n are each independently 0, 1, 2 or 3.

The invention also encompasses enantiomers of compounds of formula (I), and mixtures of enantiomers, including racemic mixtures.

Advantageously, the presently claimed compounds are capable of modulating ERAP 1, thereby rendering the compounds of therapeutic interest in the treatment of various disorders, for example, in the field of oncology and immuno-oncology.

A second aspect of the invention relates to a pharmaceutical composition comprising at least one compound as described above and a pharmaceutically acceptable carrier, diluent or excipient.

A third aspect of the invention relates to a compound as described above for use in medicine.

A fourth aspect of the invention relates to a compound as described above for use in treating or preventing a disorder selected from a proliferative disorder, an immune disorder, a viral disorder and an inflammatory disorder.

A fifth aspect of the invention relates to the use of a compound as described above in the preparation of a medicament for treating or preventing a disorder selected from a proliferative disorder, an immune disorder, a viral disorder and an inflammatory disorder.

A sixth aspect of the invention relates to a compound as described above for use in the prevention or treatment of a disorder caused by, associated with or accompanied by any abnormal ERAP1 activity.

A seventh aspect of the invention relates to the use of a compound as described above in the preparation of a medicament for the prevention or treatment of a disorder caused by, associated with or accompanied by abnormal ERAP1 activity.

An eighth aspect of the invention relates to a method of treating a mammal having a disease state alleviated by modulation of ERAP1, wherein the method comprises administering to a mammal a therapeutically effective amount of a compound as described above.

A ninth aspect of the invention relates to a compound as described above for use in treating or preventing a disease state alleviated by modulation of ERAP1.

A tenth aspect of the invention relates to the use of a compound as described above in the preparation of a medicament for treating or preventing a disease state alleviated by modulation of ERAP1.

An eleventh aspect of the invention relates to a method of treating or preventing a disorder selected from a proliferative disorder, an immune disorder, a viral disorder and an inflammatory disorder in a subject, wherein the method comprises administering to the subject a therapeutically effective amount of a compound as described above.

DETAILED DESCRIPTION

The present invention relates to bis-aryl sulfonamide compounds that are capable of modulating ERAP1.

The compounds of formula (I) contain a chiral centre, denoted * in the structure below:

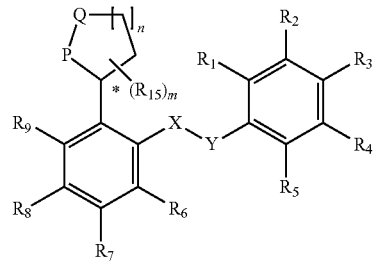

Thus, the compounds of formula (I) can exist as two different enantiomers:

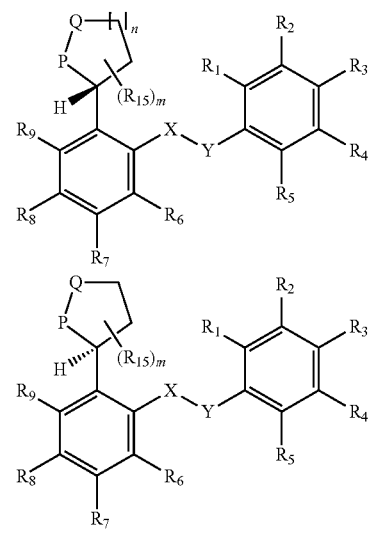

For the avoidance of doubt, the invention encompasses the compounds in either of the above configurations, as well as mixtures thereof, including racemic mixtures. The skilled person will understand that the absolute stereochemistry (R- and S-) at the chiral centre denoted * will depend on the nature of group P, and the nature and position of any substituent(s) R$^{15}$.

In one preferred embodiment, the compound is in the form of a mixture of the R- and S-enantiomers. In one preferred embodiment, the mixture is a racemic mixture, i.e. a 50:50 mixture of a compound of the R- and S-enantiomers.

Racemic mixtures can be used to prepare enantiomerically pure R- and S-forms by separating the enantiomers using standard methods, for example by chemical resolution using optically active acid or by the use of column chromatography or reverse-phase column chromatography using a substantially optically active (or "chiral") stationary phase as known to those skilled in the art. Racemic mixtures can also be used to prepare enantiomerically enriched mixtures of the S- and R-forms. Mixtures enriched with either the R- or S-enantiomer can also be obtained from the appropriate enantiomerically enriched precursors.

In one preferred embodiment of the invention, the compound is in the form of a mixture comprising enantiomers wherein the weight:weight ratio is at least approximately 2:1 or greater, preferably at least approximately 5:1 or greater, most preferably at least approximately 10:1 or greater in favour of the enantiomer that displays significant in vitro and/or in vivo activity (the eutomer).

In one embodiment, the compound is in the form of a mixture comprising the S-enantiomer and the R-enantiomer, wherein the weight:weight ratio of R-enantiomer to S-enantiomer is greater than 1.05:1, more preferably, greater than 2:1, even more preferably greater than 5:1, even more preferably greater than 10:1.

In one embodiment, the compound is in the form of a mixture comprising the S-enantiomer and the R-enantiomer, which is substantially enriched with the R-enantiomer.

In one embodiment, the compound is in the form of a mixture comprising the S-enantiomer and the R-enantiomer, wherein the weight:weight ratio of S-enantiomer to R-enantiomer is greater than 1.05:1, more preferably, greater than 2:1, even more preferably greater than 5:1, even more preferably greater than 10:1.

In one embodiment, the compound is in the form of a mixture comprising the S-enantiomer and the R-enantiomer, which is substantially enriched with the S-enantiomer.

"Alkyl" is defined herein as a straight-chain or branched alkyl radical, preferably $C_{1-20}$ alkyl, more preferably $C_{1-12}$ alkyl, even more preferably $C_{1-10}$ alkyl or $C_{1-6}$ alkyl, for example, methyl, ethyl, propyl, isopropyl, butyl, isobutyl, tert-butyl, pentyl, hexyl.

"Cycloalkyl" is defined herein as a monocyclic alkyl ring, preferably, $C_{3-7}$-cycloalkyl, more preferably $C_{3-6}$-cycloalkyl. Preferred examples include cyclopropyl, cyclobutyl, cyclopentyl, cyclohexyl or cycloheptyl, or a fused bicyclic ring system such as norbornane.

"Halogen" is defined herein as chloro, fluoro, bromo or iodo.

As used herein, the term "aryl" refers to a $C_{6-12}$ aromatic group, which may be benzocondensed, for example, phenyl or naphthyl.

"Heteroaryl" is defined herein as a monocyclic or bicyclic $C_{2-12}$ aromatic ring comprising one or more heteroatoms (that may be the same or different), such as oxygen, nitrogen or sulphur. Examples of suitable heteroaryl groups include thienyl, furanyl, pyrrolyl, pyridinyl, oxazolyl, thiazolyl, imidazolyl, pyrazolyl, isoxazolyl, isothiazolyl, oxadiazolyl, triazolyl, thiadiazolyl etc and benzo derivatives thereof, such as benzofuranyl, benzothienyl, benzimidazolyl, indolyl, isoindolyl, indazolyl etc.; or pyridyl, pyrazinyl, pyrimidinyl, pyridazinyl, triazinyl, tetrazolyl, etc. and benzo derivatives thereof, such as quinolinyl, isoquinolinyl, cinnolinyl, phthalazinyl, quinazolinyl, quinoxalinyl, naphthyridinyl etc. Particularly preferred heteroaryl groups include 1H-imidazol-5-yl, 1H-imidazol-4-yl, 1H-imidazol-2-yl, 1H-pyrrol-1-yl, 1H-pyrrol-2-yl, 1H-pyrrol-3-yl, 1H-pyrrol-4-yl, 1H-pyrrol-5-yl, 1H-pyrazol-1-yl, 1H-pyrazol-5-yl, 1H-pyrazol-3-yl, 1H-pyrazol-4-yl, oxazol-2-yl, oxazol-4-yl, oxazol-5-yl, 1H-1,2,4-triazol-3-yl, 1H-1,2,4-triazol-5-yl, 1H-1,2,4-triazol-1-yl, 1H-1,2,3-triazol-4-yl, 1H-1,2,3-triazol-5-yl, 1H-1,2,3-triazol-1-yl, thiazol-5-yl, thiazol-4-yl, 1H-1,2,3,4-tetrazol-4-yl, 2H-1,2,3,4-tetrazol-5-yl, oxazol-5-yl, oxazol-4-yl, oxazol-2-yl, isoxazol-3-yl, isoxazol-4-yl, isoxazol-5-yl, isothiazol-3-yl, isothiazol-4-yl, isothiazol-5-yl, pyridazin-3-yl, pyridazin-4-yl, pyrazinyl, 1,3,4-oxadiazol-2-yl, 1,3,4-oxadiazol-5-yl, 1,2,5-oxadiazol-3-yl, 1,2,5-oxadiazol-4-yl, 1,2,3-oxadiazol-4-yl, 1,2,3-oxadiazol-5-yl, 1,2,4-oxadiazol-3-yl, 1,2,4-oxadiazol-5-yl, isoxazol-5-yl, isoxazol-4-yl and isoxazol-3-yl.

"Heterocycloalkyl" refers to a cyclic aliphatic group containing one or more heteroatoms selected from nitrogen, oxygen and sulphur, which is optionally interrupted by one or more —(CO)— groups in the ring and/or which optionally contains one or more double bonds in the ring. Preferably, the heterocycloalkyl group is monocyclic or bicyclic. Preferably, the heterocycloalkyl group is a $C_{3-7}$-heterocycloalkyl, more preferably a $C_{3-6}$-heterocycloalkyl. Alternatively, the heterocycloalkyl group is a $C_{4-7}$-heterocycloalkyl, more preferably a $C_{4-6}$-heterocycloalkyl. Preferred heterocycloalkyl groups include, but are not limited to, piperazinyl, piperidinyl, morpholinyl, thiomorpholinyl, pyrrolidinyl, tetrahydrofuranyl and tetrahydropyranyl.

Compounds of Formula (I)

One aspect of the invention relates to compounds of formula (I) as described above.

In one preferred embodiment, P is $NR_{14}$ and Q is $CR_{12}R_{13}$.

In one preferred embodiment, Q is $NR_{14}$ and P is $CR_{12}R_{13}$.

In one preferred embodiment, P and Q are each independently $CR_{12}R_{13}$.

In one highly preferred embodiment, n is 1, 2 or 3, more preferably 1 or 2, even more preferably 2.

In one preferred embodiment, n is 0, i.e. Z is a 4-membered ring.

In one preferred embodiment, the compound is of formula (Ia-1), or a pharmaceutically acceptable salt or hydrate thereof:

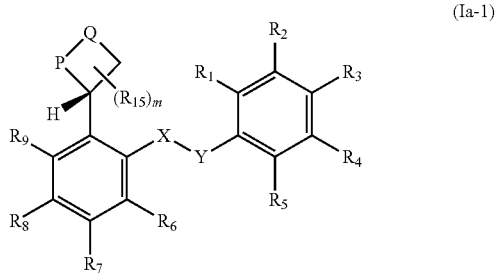

(Ia-1)

wherein P, Q, X, Y, $R^{1-9}$, $R^{15}$ and m are as defined above.

In one preferred embodiment, the compound is in enantiomerically pure form.

In one preferred embodiment, the compound is of formula (Ia-2), or a pharmaceutically acceptable salt or hydrate thereof:

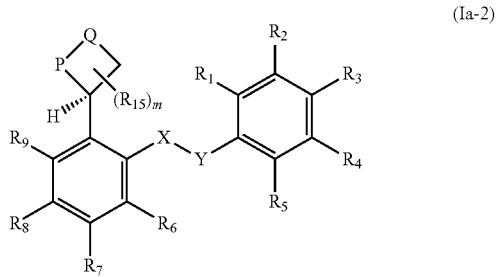

(Ia-2)

wherein P, Q, X, Y, $R^{1-9}$, $R^{15}$ and m are as defined above.

In one preferred embodiment, the compound is in enantiomerically pure form.

In one preferred embodiment, n is 1, i.e. Z is a 5-membered ring.

In one preferred embodiment, the compound is of formula (Ib-1), or a pharmaceutically acceptable salt or hydrate thereof:

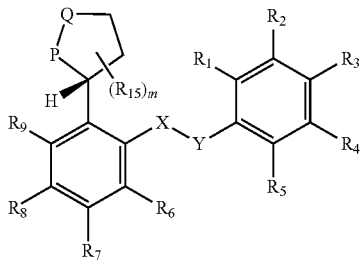

(Ib-1)

wherein P, Q, X, Y, $R^{1-9}$, $R^{15}$ and m are as defined above.

In one preferred embodiment, the compound is in enantiomerically pure form.

In another preferred embodiment, the compound is of formula (Ib-2), or a pharmaceutically acceptable salt or hydrate thereof:

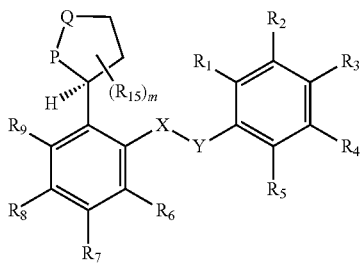

(Ib-2)

wherein P, Q, X, Y, $R^{1-9}$, $R^{15}$ and m are as defined above.

In one preferred embodiment, the compound is in enantiomerically pure form.

In one preferred embodiment, n is 2, i.e. Z is a 6-membered ring.

In one preferred embodiment, the compound is of formula (Ic-1), or a pharmaceutically acceptable salt or hydrate thereof:

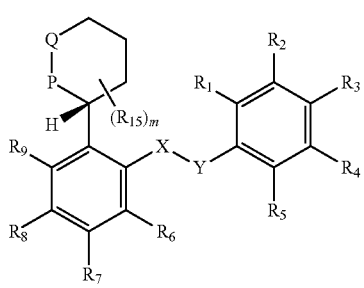

(Ic-1)

wherein P, Q, X, Y, $R^{1-9}$, $R^{15}$ and m are as defined above.

In one preferred embodiment, the compound is in enantiomerically pure form.

In one preferred embodiment, the compound is of formula (Ic-2), or a pharmaceutically acceptable salt or hydrate thereof:

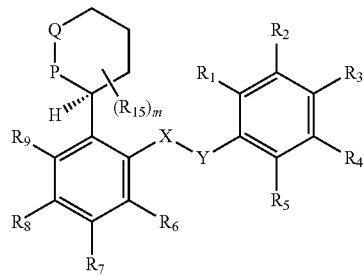

(Ic-2)

wherein P, Q, X, Y, $R^{1-9}$, $R^{15}$ and m are as defined above.

In one preferred embodiment, the compound is in enantiomerically pure form.

In one preferred embodiment, n is 3, i.e. Z is a 7-membered ring.

In one preferred embodiment, the compound is of formula (Id-1), or a pharmaceutically acceptable salt or hydrate thereof:

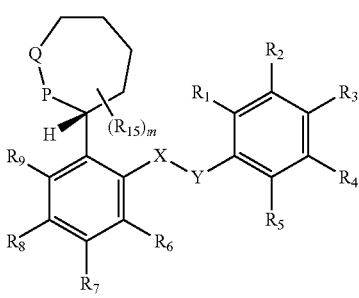

(Id-1)

wherein P, Q, X, Y, $R^{1-9}$, $R^{15}$ and m are as defined above.

In one preferred embodiment, the compound is in enantiomerically pure form.

In one preferred embodiment, the compound is of formula (Id-2), or a pharmaceutically acceptable salt or hydrate thereof:

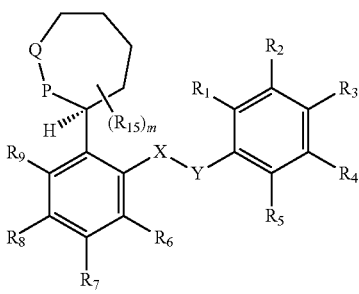

(Id-2)

wherein P, Q, X, Y, $R^{1-9}$, $R^{15}$ and m are as defined above.

In one preferred embodiment, the compound is in enantiomerically pure form.

In one preferred embodiment, m is 0, 1 or 2, more preferably 0 or 1, even more preferably 0.

In one preferred embodiment, $R_{14}$ is selected from H and Me, and is more preferably H.

In one preferred embodiment, $R_{15}$ is selected from Me, Et, Pr, Cl, F, Br, MeO, CN, $CF_3$ and OH. More preferably, $R_{15}$ is Me.

In one preferred embodiment, P is $NR_{14}$, Q is $CR_{12}R_{13}$ and n is 1 or 2.

In one preferred embodiment, Q is $NR_{14}$, P is $CR_{12}R_{13}$ and n is 1 or 2 In one preferred embodiment, P and Q are each independently $CR_{12}R_{13}$ and n is 1 or 2.

In one preferred embodiment, Z is a cyclohexyl group optionally substituted by one or more substituents selected from alkyl, halo, alkoxy, CN, haloalkyl and OH.

In one preferred embodiment, Z is a piperidin-3-yl group optionally substituted by one or more substituents selected from alkyl, halo, alkoxy, CN, haloalkyl and OH.

In one preferred embodiment, Z is a piperidin-2-yl group optionally substituted by one or more substituents selected from alkyl, halo, alkoxy, CN, haloalkyl and OH.

In one preferred embodiment, Z is a pyrrolidin-2-yl group optionally substituted by one or more substituents selected from alkyl, CN, halo, alkoxy, haloalkyl and OH.

In one preferred embodiment, Z is a pyrrolidin-3-yl group optionally substituted by one or more substituents selected from alkyl, CN, halo, alkoxy, haloalkyl and OH.

In one preferred embodiment, Z is selected from the following:

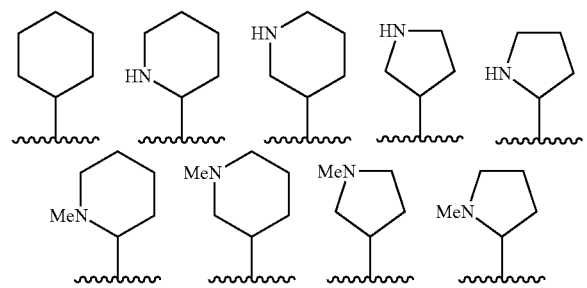

In one particularly preferred embodiment, Z is selected from the following:

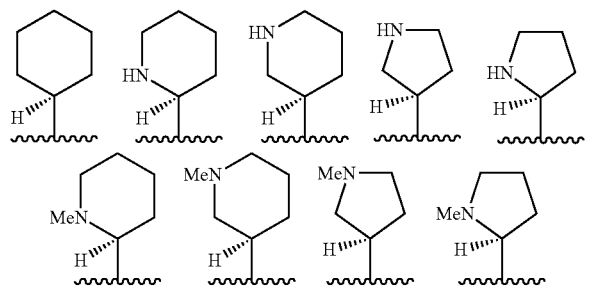

In another particularly preferred embodiment, Z is selected from the following:

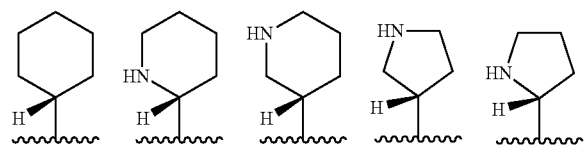

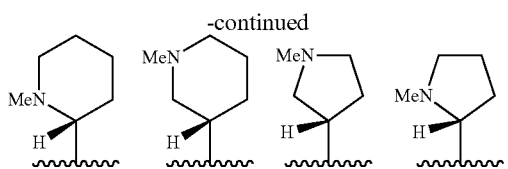

In one particularly preferred embodiment, Z is selected from the following:

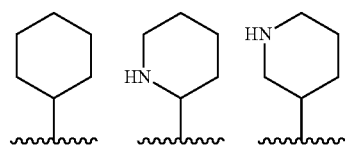

In one particularly preferred embodiment, Z is selected from the following:

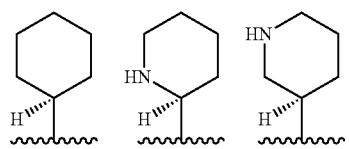

In one particularly preferred embodiment, Z is selected from the following:

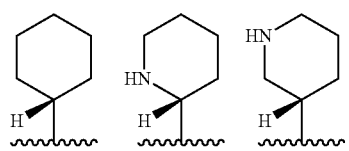

In one preferred embodiment, $R_1$ is H, CN or Me, more preferably H.

In one preferred embodiment, $R_2$ is COOH.

In one particularly preferred embodiment, X—Y is NH—$SO_2$.

In another preferred embodiment, X—Y is $SO_2$—NH.

In one preferred embodiment, $R_4$ is selected from H, Cl and F.

In one preferred embodiment, $R_5$ is selected from alkyl, haloalkyl, $SO_2$-alkyl, Cl, alkoxy, OH, CN, hydroxyalkyl, alkylthio, heteroaryl, cycloalkyl, heterocycloalkyl and haloalkoxy.

In one preferred embodiment, $R_5$ is selected from alkyl, alkoxy and cycloalkyl. More preferably, $R_5$ is cycloalkyl.

In one particularly preferred embodiment, $R_5$ is selected from OMe, OEt, Me, Et, and cyclopropyl.

In another preferred embodiment, $R_5$ is selected from H, Me, $CF_3$, $CHF_2$, $SO_2$-Me, Cl, MeO, OH, $CH_2OH$, SMe, cyclopropyl, triazolyl, oxetanyl and CN. More preferably, $R_5$ is selected from H, CN, Me, $SO_2$-Me, $CF_3$ and $CHF_2$, $CH_2OH$, SMe, cyclopropyl, 3,4-triazol-1-yl, oxetan-3-yl. More preferably, $R_5$ is selected from H, CN, Me, $SO_2$-Me, $CF_3$ and $CHF_2$.

In another preferred embodiment, $R_5$ is selected from OMe, Me, Et, Pr and Cl, and is more preferably OMe or Et.

In one particularly preferred embodiment, $R_5$ is selected from OMe, Et, and cyclopropyl.

In one particularly preferred embodiment, $R_5$ is cyclopropyl.

In one particularly preferred embodiment, $R_5$ is OMe.

In one particularly preferred embodiment, $R_5$ is Et.

In one preferred embodiment, $R_7$ is selected from H, CN, haloalkyl, Cl, F, $SO_2$-alkyl, $CONR_{10}R_{11}$, $SO_2NR_{16}R_{17}$, heteroaryl and alkyl, wherein said heteroaryl group is optionally substituted by one or more substituents selected from alkyl, halo, alkoxy, CN, haloalkyl and OH.

In one preferred embodiment, $R_7$ is a heteroaryl group optionally substituted by one or more substituents selected from alkyl, halo, alkoxy, CN, haloalkyl and OH.

In one preferred embodiment, $R^7$ is a heteroaryl group selected from pyridinyl, thienyl, imidazolyl, pyrimidinyl, pyrazolyl, pyrazinyl, pyridizinyl, thiazolyl, isothiazolyl, triazinyl, pyrrolyl, furanyl, oxazolyl, isoxazolyl, oxadiazolyl, tetrazolyl and triazolyl, each of which is optionally substituted by one or more substituents selected from alkyl, halo, alkoxy, CN, haloalkyl and OH.

In one preferred embodiment, $R^7$ is a heteroaryl group selected from imidazolyl, pyrazolyl, pyrazinyl, pyridizinyl, thiazolyl, isothiazolyl, oxazolyl, isoxazolyl, oxadiazolyl, tetrazolyl and triazolyl, each of which is optionally substituted by one or more substituents selected from alkyl, halo, alkoxy, CN, haloalkyl and OH.

In one preferred embodiment, $R^7$ is a heteroaryl group selected from 1H-imidazol-5-yl, 1H-imidazol-4-yl, 1H-imidazol-2-yl, 1H-pyrrol-1-yl, 1H-pyrrol-2-yl, 1H-pyrrol-3-yl, 1H-pyrrol-4-yl, 1H-pyrrol-5-yl, 1H-pyrazol-1-yl, 1H-pyrazol-5-yl, 1H-pyrazol-3-yl, 1H-pyrazol-4-yl, oxazol-2-yl, oxazol-4-yl, oxazol-5-yl, 1H-1,2,4-triazol-3-yl, 1H-1,2,4-triazol-5-yl, 1H-1,2,4-triazol-1-yl, 1H-1,2,3-triazol-4-yl, 1H-1,2,3-triazol-5-yl, 1H-1,2,3-triazol-1-yl, thiazol-5-yl, thiazol-4-yl, 1H-1,2,3,4-tetrazol-4-yl, 2H-1,2,3,4-tetrazol-5-yl, oxazol-5-yl, oxazol-4-yl, oxazol-2-yl, isoxazol-3-yl, isoxazol-4-yl, isoxazol-5-yl, isothiazol-3-yl, isothiazol-4-yl, isothiazol-5-yl, pyradizin-3-yl, pyradizin-4-yl, pyrazinyl, 1,3,4-oxadizol-2-yl, 1,3,4-oxadizol-5-yl, 1,2,5-oxadiazol-3-yl, 1,2,5-oxadiazol-4-yl, 1,2,3-oxadiazol-4-yl, 1,2,3-oxadiazol-5-yl, 1,2,4-oxadiazol-3-yl, 1,2,4-oxadiazol-5-yl, isoxazol-5-yl, isoxazol-4-yl and isoxazol-3-yl, each of which is optionally substituted by one or more substituents selected from alkyl, halo, CN, alkoxy, haloalkyl and OH.

In one highly preferred embodiment, $R^7$ is a heteroaryl group selected from 1H-pyrazol-5-yl, 1H-pyrazol-3-yl, 1H-pyrazol-4-yl, oxazol-2-yl, 1H-1,2,3-triazol-4-yl, 1H-1,2,3-triazol-5-yl, thiazol-5-yl, 1H-1,2,3,4-tetrazol-4-yl, 2H-1,2,3,4-tetrazol-5-yl, isoxazol-4-yl, isoxazol-5-yl, isothiazol-5-yl, pyradizin-3-yl, pyradizin-4-yl, pyrazinyl and 1,3,4-oxadizol-2-yl, each of which is optionally substituted by one or more substituents selected from Me, F, Cl, CN and MeO.

In one highly preferred embodiment, $R^7$ is a heteroaryl group selected from 1H-1,2,3,4-tetrazol-4-yl and 2H-1,2,3,4-tetrazol-5-yl, each of which is optionally substituted by one or more substituents selected from Me, F, Cl, CN and MeO.

In one preferred embodiment, $R_7$ is selected from CN, haloalkyl, $SO_2$-alkyl, $SO_2NR_{16}R_{17}$, $CONR_{10}R_{11}$ and tetrazolyl.

In one preferred embodiment, $R_7$ is selected from $CF_3$, CN, $CONH_2$, 1H-1,2,3,4-tetrazol-1-yl, $SO_2NH_2$ and $SO_2Me$.

In one preferred embodiment, $R_7$ is selected from H, CN, $CF_3$, $CHF_2$, Cl, F, $SO_2$-Me, $CONH_2$, $SO_2NH_2$, heteroaryl and Me. More preferably, $R_7$ is selected from H, CN, Me, $SO_2$-Me, $CONH_2$, $SO_2NH_2$, tetrazolyl, $CF_3$ and $CHF_2$.

In another preferred embodiment, $R_7$ is selected from CN, haloalkyl, $SO_2$-alkyl, $SO_2NH_2$, $CONR_{10}R_{11}$ and tetrazolyl. More preferably for this embodiment, $R_7$ is selected from $CF_3$, CN, $SO_2NH_2$, 1H-1,2,3,4-tetrazol-1-yl, $CONH_2$ and $SO_2Me$, more preferably from $CF_3$, CN, 1H-1,2,3,4-tetrazol-1-yl and $SO_2Me$.

In one preferred embodiment, $R_7$ is haloalkyl or heteroaryl, more preferably tetrazolyl.

In one preferred embodiment, $R_7$ is haloalkyl, more preferably, $CF_3$.

In one preferred embodiment, $R_7$ is CN.

In one preferred embodiment, $R_7$ is $SO_2$-alkyl, more preferably $SO_2Me$.

In one preferred embodiment, $R_7$ is $SO_2NR_{16}R_{17}$, more preferably $SO_2NH_2$.

In one preferred embodiment, $R_8$ is selected from H, alkyl, haloalkyl and Cl.

In one preferred embodiment, $R_8$ is selected from H, Cl, F and Me. More preferably, Ra is selected from H, Cl and F.

In one preferred embodiment, $R_8$ is selected from H, alkyl and halo.

In another preferred embodiment, $R_8$ is selected from alkyl and halo. More preferably, $R_8$ is selected from Me, Cl and F.

In one preferred embodiment, $R_8$ is H or haloalkyl, more preferably H or $CF_3$, even more preferably H.

In one preferred embodiment, $R_8$ is H or F, more preferably, H.

In one preferred embodiment, $R_1$, $R_3$, $R_4$, $R_6$, $R_8$ and $R_9$ are all H.

In One Preferred Embodiment:

$R_2$ is COOH;

X—Y is NH—$SO_2$;

$R_5$ is selected from OMe, OEt, Me, Et, and cyclopropyl, and is more preferably OMe, cyclopropyl or Et;

$R_1$, $R_3$, $R_4$, $R_6$, $R_8$ and $R_9$ are all H; and $R_7$ is selected from CN, haloalkyl, $SO_2$-alkyl and tetrazolyl, and is more preferably, haloalkyl, $SO_2$ Me or CN.

In One Preferred Embodiment:

$R_2$ is COOH;

X—Y is NH—$SO_2$;

$R_5$ is selected from cyclopropyl, OMe and Et;

$R_1$, $R_3$, $R_4$, $R_6$, $R_8$ and $R_9$ are all H; and $R_7$ is selected from CN, haloalkyl, heteroaryl and $SO_2$-alkyl; and Z is selected from the following:

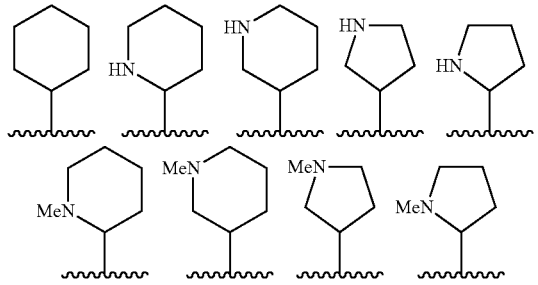

For this embodiment, preferably the group Z has a configuration corresponding to that of formula (Ib-1) or (Ic-1) as described hereinabove. Alternatively, for this embodiment, preferably the group Z has a configuration corresponding to that of formula (Ib-2) or (Ic-2) as described hereinabove.

In One Preferred Embodiment:
R₂ is COOH;
X—Y is NH—SO₂;
R₅ is selected from cyclopropyl, OMe and Et;
R₁, R₃, R₄, R₆ and R₉ are all H; and
R₇ is selected from CN, haloalkyl, heteroaryl and SO₂-alkyl;
R₈ is selected from H, Cl and F; and
Z is selected from the following:

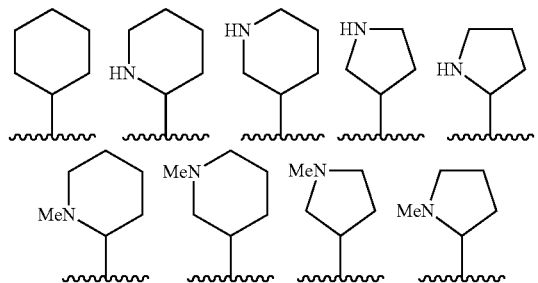

For this embodiment, preferably the group Z has a configuration corresponding to that of formula (Ib-1) or (Ic-1) as described hereinabove. Alternatively, for this embodiment, preferably the group Z has a configuration corresponding to that of formula (Ib-2) or (Ic-2) as described hereinabove.

In One Preferred Embodiment:
R₂ is COOH;
X—Y is NH—SO₂;
R₅ is selected from cyclopropyl, OMe and Et;
R₁, R₃, R₄, R₆, R₈ and R₉ are all H; and
R₇ is selected from CN, haloalkyl, heteroaryl and SO₂-alkyl; and
Z is selected from the following:

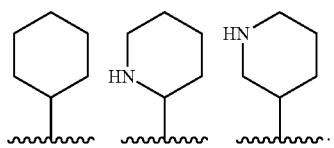

For this embodiment, preferably the group Z has a configuration corresponding to that of formula (Ib-1) or (Ic-1) as described hereinabove. Alternatively, for this embodiment, preferably the group Z has a configuration corresponding to that of formula (Ib-2) or (Ic-2) as described hereinabove.

In One Preferred Embodiment:
R₂ is COOH;
X—Y is NH—SO₂;
R₅ is selected from cyclopropyl, OMe and Et;
R₁, R₃, R₄, R₆ and R₉ are all H;
R₇ is selected from CN, haloalkyl, heteroaryl and SO₂-alkyl, more preferably CF₃, SO₂Me, CN and tetrazolyl;
R₈ is selected from H, Cl and F; and
Z is selected from the following:

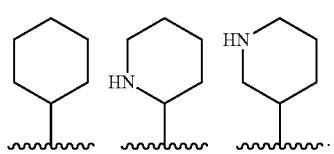

For this embodiment, preferably the group Z has a configuration corresponding to that of formula (Ib-1) or (Ic-1) as described hereinabove. Alternatively, for this embodiment, preferably the group Z has a configuration corresponding to that of formula (Ib-2) or (Ic-2) as described hereinabove.

In One Preferred Embodiment:
R₂ is COOH;
X—Y is NH—SO₂;
R₅ is selected from cyclopropyl, OMe and Et;
R₁, R₃, R₄, R₆ and R₉ are all H; and
R₇ is selected from CN, haloalkyl, heteroaryl and SO₂-alkyl, more preferably CF₃, SO₂Me, CN and tetrazolyl;
R₈ is selected from H, Cl and F; and
Z is:

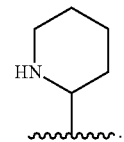

For this embodiment, preferably the group Z has a configuration corresponding to that of formula (Ib-1) or (Ic-1) as described hereinabove. Alternatively, for this embodiment, preferably the group Z has a configuration corresponding to that of formula (Ib-2) or (Ic-2) as described hereinabove.

In One Preferred Embodiment:
R₂ is COOH;
X—Y is NH—SO₂;
R₅ is cyclopropyl;
R₁, R₃, R₄, R₆, R₈ and R₉ are all H; and
R₇ is selected from CN, haloalkyl and SO₂-alkyl, and is more preferably, SO₂ Me, CN or CF₃; and
Z is selected from the following:

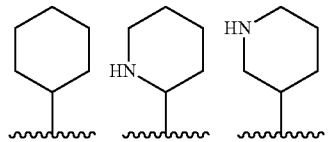

For this embodiment, preferably the group Z has a configuration corresponding to that of formula (Ib-1) or (Ic-1) as described hereinabove. Alternatively, for this embodiment, preferably the group Z has a configuration corresponding to that of formula (Ib-2) or (Ic-2) as described hereinabove.

In One Preferred Embodiment:
R₂ is COOH;
X—Y is NH—SO₂;
R₅ is Et;
R₁, R₃, R₄, R₆, R₈ and R₉ are all H; and
R₇ is selected from CN, haloalkyl, heteroaryl, SO₂-alkyl; and
Z is selected from the following:

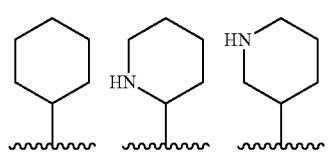

For this embodiment, preferably the group Z has a configuration corresponding to that of formula (Ib-1) or (Ic-1) as described hereinabove. Alternatively, for this embodiment, preferably the group Z has a configuration corresponding to that of formula (Ib-2) or (Ic-2) as described hereinabove.

In One Preferred Embodiment:
$R_2$ is COOH;
X—Y is NH—$SO_2$;
$R_5$ is Et;
$R_1$, $R_3$, $R_4$, $R_6$, $R_8$ and $R_9$ are all H; and
$R_7$ is selected from CN, $SO_2$Me and $CF_3$; and
Z is selected from the following:

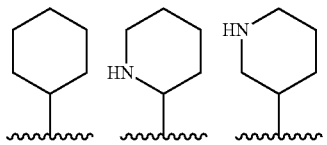

For this embodiment, preferably the group Z has a configuration corresponding to that of formula (Ib-1) or (Ic-1) as described hereinabove. Alternatively, for this embodiment, preferably the group Z has a configuration corresponding to that of formula (Ib-2) or (Ic-2) as described hereinabove.

In One Preferred Embodiment:
$R_2$ is COOH;
X—Y is NH—$SO_2$;
$R_5$ is Et;
$R_1$, $R_3$, $R_4$, $R_6$, $R_8$ and $R_9$ are all H; and
$R_7$ is selected from CN and $CF_3$; and
Z is selected from the following:

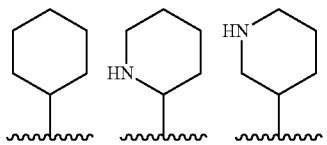

For this embodiment, preferably the group Z has a configuration corresponding to that of formula (Ib-1) or (Ic-1) as described hereinabove. Alternatively, for this embodiment, preferably the group Z has a configuration corresponding to that of formula (Ib-2) or (Ic-2) as described hereinabove.

In One Preferred Embodiment:
$R_2$ is COOH;
X—Y is NH—$SO_2$;
$R_5$ is MeO;
$R_1$, $R_3$, $R_4$, $R_6$, $R_8$ and $R_9$ are all H; and
$R_7$ is selected from CN, haloalkyl and $SO_2$-alkyl; and
Z is selected from the following:

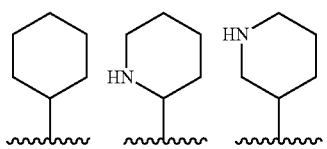

For this embodiment, preferably the group Z has a configuration corresponding to that of formula (Ib-1) or (Ic-1) as described hereinabove. Alternatively, for this embodiment, preferably the group Z has a configuration corresponding to that of formula (Ib-2) or (Ic-2) as described hereinabove.

In one preferred embodiment, the compound of formula (I) is selected from the following:

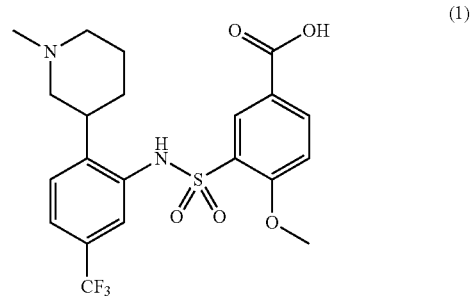

(1)

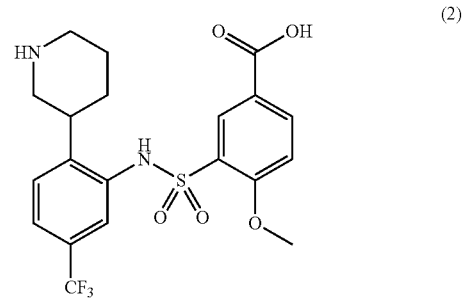

(2)

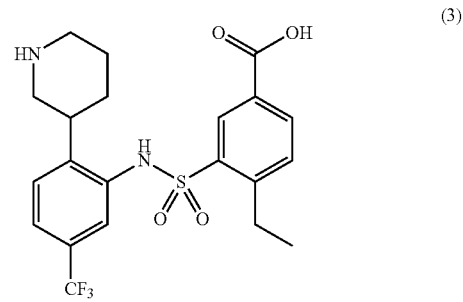

(3)

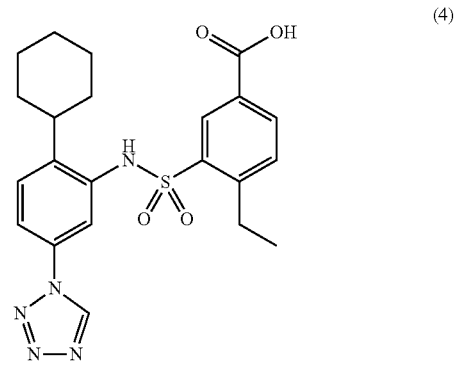

(4)

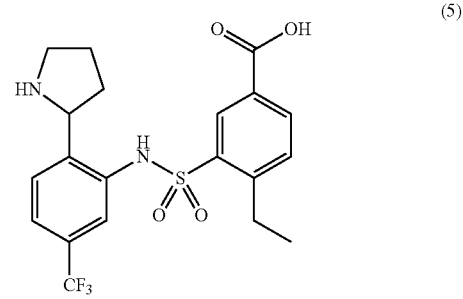

(5)

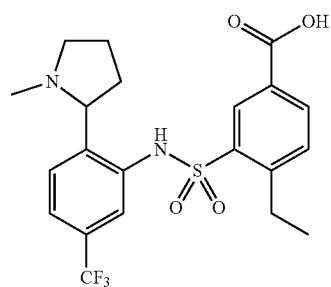
(6)
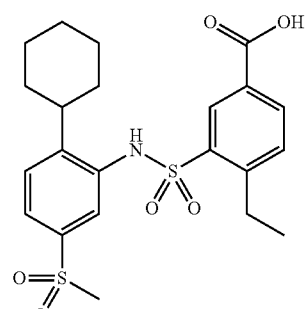
(11)
(7)
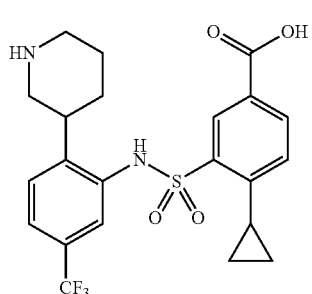
(12)
(8)
(13)
(9)
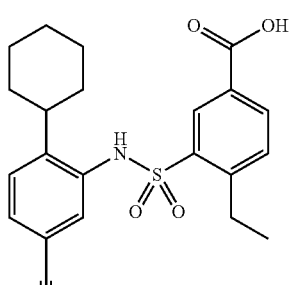
(14)
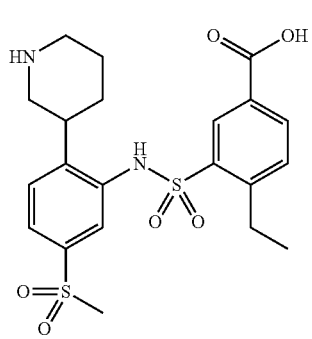
(10)
(15)
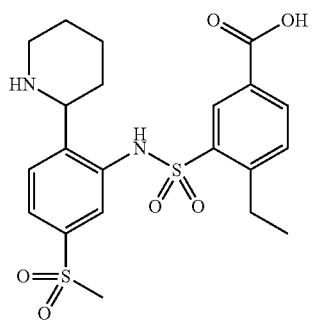

-continued
(16)
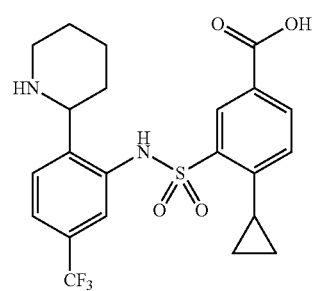
(17)
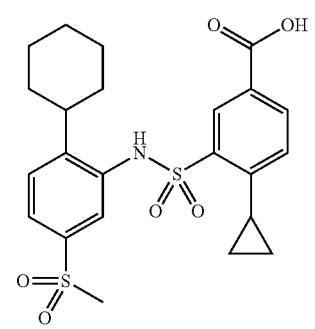
(18)
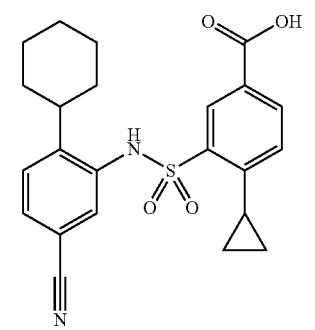
(19)
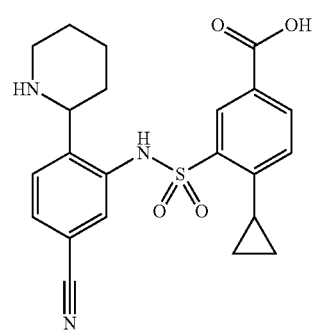
(20)
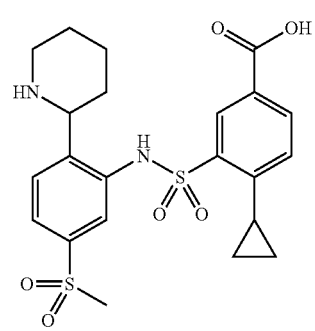
-continued
(21)
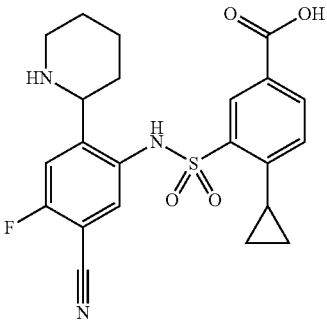
(22)
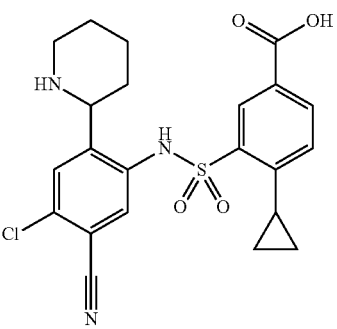
(23)
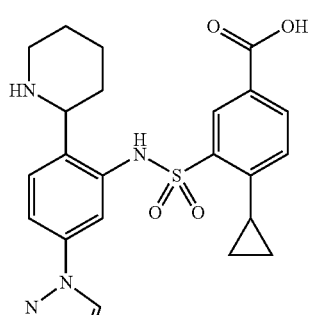
(24)
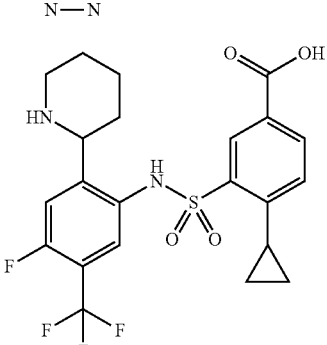
(25)
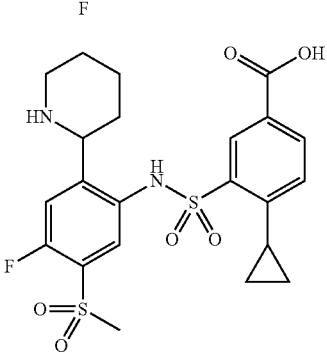

(26) 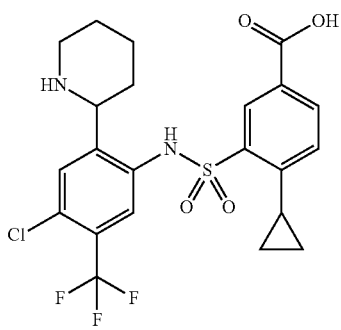

(27) 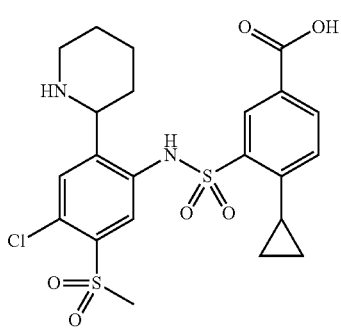

(28) 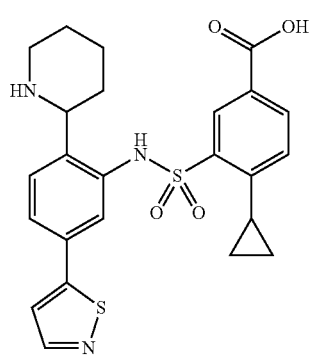

(29)E1 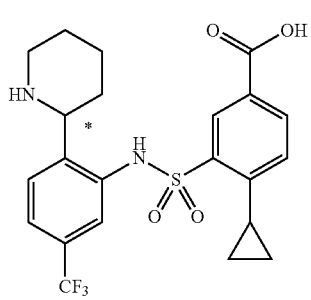

(30)E2 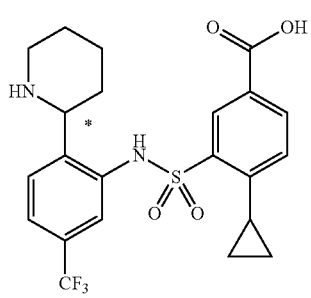

(31) 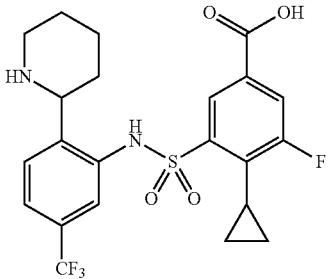

and pharmaceutically acceptable salts and hydrates thereof. Examples are racemic at the single chiral centre, otherwise, E1 and E2 refer to separated enantiomers 1 and 2 of undefined absolute configuration.

In one preferred embodiment, the compound of the invention exhibits an $IC_{50}$ against Decapeptide WRVYEKC(Dnp) ALK-acid (where Dnp is Dinitrophenyl maleimide) (10-mer) of 100 nM to 500 nM, more preferably, less than 100 nM. Further details of this assay are detailed in the accompanying examples.

In one preferred embodiment, the compound of the invention is selected from compounds (2)-(31). In an even more preferred embodiment, the compound of the invention is selected from the following compounds (3), (4) and (7)-(31).

Therapeutic Applications

A further aspect of the invention relates to compounds as described herein for use in medicine. The compounds have particular use in the field of oncology and immunoncology, as described in more detail below.

Yet another aspect of the invention relates to compounds as described herein for use in treating or preventing a disorder selected from a proliferative disorder, an immune disorder, an inflammatory disorder and a viral disorder.

In a preferred embodiment, the compound of the invention modulates ERAP1.

In one embodiment the compound inhibits the activity of ERAP1.

In an alternative embodiment the compound increases the activity of ERAP1.

In one embodiment the compound of the invention may change the repertoire of presented antigens.

One aspect of the invention relates to a compound as described herein for use in treating a proliferative disorder. Preferably, the proliferative disorder is a cancer or leukemia.

A cancer may be selected from: basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

Without wishing to be bound by theory, it is understood that ERAP1 modulators are capable of changing at least 10% of the antigen and neoantigen repertoire of cancer cells, as measured using immunopeptidomics and mass spectrometry analysis. Approximately 50% of this change is an upregulation in the presentation of certain antigens and neoantigens, whilst the other 50% is the presentation of entirely novel antigens and neoantigens. Both changes lead to an increase in the visibility of the tumour to the immune system, leading to measurable changes in the $CD8^+$ T cell repertoire and $CD8^+$ T cell activation status. This change in $CD8^+$ T cell response leads to immune-mediated tumour clearance, and can be potentially enhanced by combining with cancer therapeutics such as antibody checkpoint inhibitors (e.g. anti-PD-1).

Without wishing to be bound by theory, it is understood that modulators of ERAP1 cause killing of cancer cells by natural killer (NK) cells due to disruption of the interaction between killer cell Ig-like receptors (KIR) or lectin-like receptor CD94-NKG2A on NK cells with classical or non-classical MHC-I-peptide (pMHC-I) complexes on cancer cells.

In one preferred embodiment, the disorder is cancer, and the compound increases the visibility of cancer cells to the immune system by altering the repertoire of antigens and neoantigens presented to the immune system.

A further aspect of the invention relates to a method of increasing the visibility of cancer cells to the immune system in a subject by altering the repertoire of antigens and neoantigens presented to the immune system, said method comprising administering to the subject a compound of formula (I).

In one preferred embodiment, the compound increases the $CD8^+$ T cell response to the cancer cell.

In one preferred embodiment, the compound of the invention is for use in the treatment of a disease of uncontrolled cell growth, proliferation and/or survival, an inappropriate cellular immune response, or an inappropriate cellular inflammatory response, particularly in which the uncontrolled cell growth, proliferation and/or survival, inappropriate cellular immune response, or inappropriate cellular inflammatory response is modulated by the ERAP1 pathway.

In one preferred embodiment, the disease of uncontrolled cell growth, proliferation and/or survival, inappropriate cellular immune response, or inappropriate cellular inflammatory response is selected from a haematological tumour, a solid tumour and/or metastases thereof.

More preferably, the compound is for use in treating a disorder selected from leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The compound may kill cancer cells, reduce the number of proliferating cells in the cancer and/or reduce the volume or size of a tumour comprising the cancer cells. The compound may reduce the number of metastasising cancer cells.

In one embodiment the compound may be used (or is for use) in treating cancer in a subject who has previously had cancer. The compound may be used to reduce the likelihood of the cancer recurring, or the likelihood of further cancer developing. The compound may induce a neoantigen in the recurring or further cancer to which the subject already possesses an existing immune response. As such, the compound may increase or boost an immune response against the cancer.

In one embodiment the compound is for use in preventing cancer. The compound may be used for prophylaxis against the development of cancer. That is to say, the compound may stimulate an immune response, such as a vaccine response, against a future cancer. The compound may stimulate in a subject an immune response directed to a neoantigen. Once a cancer develops in the subject, they may be treated again with the compound (or a different compound) to stimulate development of the same neoantigen, thereby eliciting the subject's pre-existing immune response to said neoantigen to treat or prevent the cancer.

The same or a different compound may be used before and after the cancer develops in a subject.

In one embodiment the compound may be used for the prevention of cancer.

In one embodiment the subject may previously have had cancer, may have a familial history of cancer, may have a high risk for developing cancer, may have a genetic predisposition to developing cancer, or may have been exposed to a carcinogenic agent. In one embodiment the subject may be in remission from cancer.

One embodiment provides ex vivo generated antigen-presenting cells, such as dendritic cells (DCs). The antigen-presenting cells may be produced ex vivo to present neoantigens, such as those generated by a compound according to the present invention. The compound may be used in a method for producing ex vivo an antigen-presenting cell which presents a neo-antigen, and wherein the cell may be used as a vaccine against cancer.

The antigen presenting cell such as a dendritic cell may be pulsed or loaded with the neo-antigen or genetically modified (via DNA or RNA transfer) to express one, two or more neo-antigens. Methods of preparing dendritic cell vaccines are known in the art. The neo-antigen may be generated from the subject's normal tissue in which ERAP1 is modulated with a compound according to the invention. Sources of normal tissue may be fibroblasts or B cells, for example, that can be readily expanded in vitro.

Alternatively, RNA from the cancer, total or mRNA enriched poly A+ RNA may be used. Poly A+ RNA can be also amplified to generate sufficient antigen for DC loading and thereby limit the ex vivo culture step.

In one embodiment a dendritic cell which has been treated with the compound as described above may be used to treat a subject. The dendritic cell may be contacted with the compound ex vivo, and then the dendritic cell may be administered to the subject. The compound may therefore be used in vitro or in vivo, for example either for in situ treatment or for ex vivo treatment followed by the administration of the treated cells to the subject.

Another aspect of the invention relates to a compound as described above for use in treating an immune disorder. In one preferred embodiment, the immune disorder is an autoimmune disorder.

Examples of the autoimmune disorders include, but are not limited to: rheumatoid arthritis (RA), myasthenia gravis (MG), multiple sclerosis (MS), systemic lupus erythematosus (SLE), autoimmune thyroiditis (Hashimoto's thyroiditis), Graves' disease, inflammatory bowel disease, autoimmune uveoretinitis, polymyositis and certain types of diabetes, systemic vasculitis, polymyositis-dermatomyositis, systemic sclerosis (scleroderma), Sjogren's Syndrome, ankylosing spondylitis and related spondyloarthropathies, rheumatic fever, hypersensitivity pneumonitis, allergic bronchopulmonary aspergillosis, inorganic dust pneumoconiosis, sarcoidosis, autoimmune hemolytic anemia, immunological platelet disorders, cryopathies such as cryofibrinogenemia, psoriasis, Behçet's disease, birdshot chorioretinopathy and autoimmune polyendocrinopathies.

Polymorphisms in the ERAP1 gene that impact ERAP1 enzymatic activity are strongly associated with an increased risk of autoimmunity, including the diseases ankylosing spondylitis, psoriasis, Behçet's disease and birdshot chorioretinopathy[11]. Variants of ERAP1 that reduce ERAP1 enzymatic activity are protective against disease, whilst those that reportedly elevate activity are associated with increased disease risk[12]. This suggests that modulation of ERAP1 activity could be an effective treatment for autoimmune diseases.

Thus, in one preferred embodiment, the immune disorder is selected from ankylosing spondylitis, psoriasis, Behçet's disease and birdshot chorioretinopathy.

In one preferred embodiment, the immune disorder is ankylosing spondylitis. Ankylosing spondylitis (AS) is a type of arthritis in which there is long term inflammation of the joints of the spine. Typically, the joints where the spine joins the pelvis are also affected. Occasionally other joints such as the shoulders or hips are involved. Between 0.1% and 1.8% of people are affected and onset is typically in young adults. Although the cause of ankylosing spondylitis is unknown, it involves a combination of genetic and environmental factors. More than 90% of those affected have a specific human leukocyte antigen known as the HLA-B27 antigen[13]. In addition, certain variants of ERAP1, in conjunction with HLA-B27, are clearly associated with either an elevated or reduced risk of disease, providing evidence of a clear role for modulated antigen presentation in disease[18]. There is no cure for ankylosing spondylitis and current treatments serve only to improve symptoms and prevent worsening. Medications used to date include NSAIDs, steroids, DMARDs such as sulfasalazine, and biologic agents such as infliximab.

In one preferred embodiment, the immune disorder is Behçet's disease (BD). Behçet's disease (BD) is a type of inflammatory disorder which affects multiple parts of the body. The most common symptoms include painful mouth sores, genital sores, inflammation of parts of the eye, and arthritis. The cause is not well-defined, and whilst environmental factors play a role, genetic studies have shown an increased risk of disease in patients carrying HLA-B51 in conjunction with specific variants of ERAP1.[19] The disease is primarily characterized by auto-inflammation of the blood vessels, hence it is sometimes characterised as an auto-inflammatory disease. There is currently no cure for Behçet's disease, but the symptoms can be controlled with medicines that reduce inflammation in the affected parts of the body, for example, with corticosteroids, immunosuppressants or biological therapies that target the biological processes involved in the process of inflammation. In one preferred embodiment, the immune disorder is birdshot chorioretinopathy. Birdshot chorioretinopathy, also known as Birdshot Uveitis or HLA-A29 Uveitis, is a rare form of bilateral posterior uveitis affecting the eye. It causes severe, progressive inflammation of both the choroid and retina. Symptoms include floaters, blurred vision, photopsia (flashing lights in eyes), loss of color vision and nyctalopia. Birdshot chorioretinopathy is thought to be an autoimmune disease. The disease has strong association with the Human leukocyte antigen haplotype (HLA)-A29. This indicates a role for T-lymphocytes in the pathogenesis. Birdshot chorioretinopathy is associated with IL-17, a hallmark cytokine of TH17 cells that play an important role in autoimmunity.[15, 16] A genome-wide association study has ascertained HLA-A29:02 as the primary risk factor and identified that both ERAP1 and ERAP2 are associated with birdshot chorioretinopathy.[17, 20] Genetic variants within the ERAP1 and ERAP2 loci modulate enzyme activity and also mRNA and protein expression. ERAP2 is an aminopeptidase that, together with ERAP1, trims peptides in the endoplasmic reticulum and loads these peptides on HLA molecules for presentation to T cells of the immune system.

In one preferred embodiment, the immune disorder is psoriasis. Psoriasis is a chronic skin disease in which skin cells rapidly build up on the surface of the skin forming scales and red patches that are itchy and sometimes painful. The cause is not well-defined but includes both environmental and genetic factors. HLA-C06 strongly associates with risk of disease and variants in ERAP1, possibly in conjunction with HLA-C06, are also strongly associated with disease.[21] There is no cure for psoriasis and current treatments serve only to improve symptoms and prevent worsening. Medications used in therapy include steroids, methotrexate, sulfasalazine, and biologic agents such as etanercept.

Another aspect of the invention relates to a compound as described above for use in treating or preventing a viral disorder. Modulators of ERAP1 such as the compounds described herein are capable of changing the antigen repertoire of multiple viruses, which leads to the recognition and destruction of viral infected cells. Accordingly, ERAP1 modulators have potential therapeutic applications in the treatment of viral infection and diseases. ERAP1 modulates certain viral antigens, including those from human papilloma virus (HPV), human cytomegalovirus (CMV) hepatitis C (HCV) and human immunodeficiency virus (HIV)[8, 9, 10]. In addition, knockdown of ERAP1 in HPV infected cells changes the repertoire of presented HPV antigens leading to greater recognition by CD8$^+$ T cells[8].

In one preferred embodiment, the viral disorder is a viral disease or viral infection selected from HIV, HPV, CMV and HCV.

In one preferred embodiment, the viral disorder is HIV.
In one preferred embodiment, the viral disorder is HPV.
In one preferred embodiment, the viral disorder is CMV.
In one preferred embodiment, the viral disorder is HCV.

Another aspect relates to a compound as described herein for use in the prevention or treatment of a disorder caused by, associated with or accompanied by abnormal activity against ERAP1.

Another aspect relates to a compound as described herein for use in the prevention or treatment of an ERAP1-associated disease or disorder.

Yet another aspect relates to the use of a compound as described herein in the preparation of a medicament for the prevention or treatment of a disorder caused by, associated with or accompanied by any abnormal activity against ERAP1.

As used herein the phrase "preparation of a medicament" includes the use of the components of the invention directly as the medicament in addition to their use in any stage of the preparation of such a medicament.

Another aspect relates to the use of a compound as described above in the preparation of a medicament for treating or preventing a disorder selected from a proliferative disorder, an immune disorder, a viral disorder and an inflammatory disorder.

Yet another aspect relates to the use of a compound as described herein in the preparation of a medicament for the prevention or treatment of an ERAP1-associated disease or disorder.

Another aspect of the invention relates to a method of treating an ERAP1-associated disease or disorder in a subject. The method according to this aspect of the present invention is effected by administering to a subject in need thereof a therapeutically effective amount of a compound of the present invention, as described hereinabove, either per se, or, more preferably, as a part of a pharmaceutical composition, mixed with, for example, a pharmaceutically acceptable carrier, as is detailed hereinafter.

Yet another aspect of the invention relates to a method of treating a subject having a disease state alleviated by modulation of ERAP1 wherein the method comprises administering to the subject a therapeutically effective amount of a compound according to the invention.

Another aspect relates to a method of treating a disease state alleviated by modulation of ERAP1, wherein the method comprises administering to a subject a therapeutically effective amount of a compound according to the invention.

Preferably, the subject is a mammal, more preferably a human.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Herein, the term "treating" includes abrogating, substantially inhibiting, slowing or reversing the progression of a disease or disorder, substantially ameliorating clinical symptoms of a disease or disorder or substantially preventing the appearance of clinical symptoms of a disease or disorder.

Herein, the term "preventing" refers to a method for barring an organism from acquiring a disorder or disease in the first place.

The term "therapeutically effective amount" refers to that amount of the compound being administered which will relieve to some extent one or more of the symptoms of the disease or disorder being treated.

For any compound used in this invention, a therapeutically effective amount, also referred to herein as a therapeutically effective dose, can be estimated initially from cell culture assays. For example, a dose can be formulated in animal models to achieve a circulating concentration range that includes the $IC_{50}$ or the $IC_{100}$ as determined in cell culture. Such information can be used to more accurately determine useful doses in humans. Initial dosages can also be estimated from in vivo data. Using these initial guidelines one of ordinary skill in the art could determine an effective dosage in humans.

Moreover, toxicity and therapeutic efficacy of the compounds described herein can be determined by standard pharmaceutical procedures in cell cultures or experimental animals, e.g., by determining the $LD_{50}$ and the $ED_{50}$. The dose ratio between toxic and therapeutic effect is the therapeutic index and can be expressed as the ratio between $LD_{50}$ and $ED_{50}$. Compounds which exhibit high therapeutic indices are preferred. The data obtained from these cell cultures assays and animal studies can be used in formulating a dosage range that is not toxic for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (see, e.g., Fingl et al, 1975, The Pharmacological Basis of Therapeutics, chapter 1, page 1).

Dosage amount and interval may be adjusted individually to provide plasma levels of the active compound which are sufficient to maintain therapeutic effect. Usual patient dosages for oral administration range from about 50-2000 mg/kg/day, commonly from about 100-1000 mg/kg/day, preferably from about 150-700 mg/kg/day and most preferably from about 250-500 mg/kg/day. Preferably, therapeutically effective serum levels will be achieved by administering multiple doses each day. In cases of local administration or selective uptake, the effective local concentration of the drug may not be related to plasma concentration. One skilled in the art will be able to optimize therapeutically effective local dosages without undue experimentation.

As used herein, "ERAP1-related disease or disorder" refers to a disease or disorder characterized by inappropriate ERAP1 activity. Inappropriate activity refers to either an increase or decrease in ERAP1 activity relative to wildtype ERAP1 (Uniprot ID Q9NZ08), caused by variation in the ERAP1 protein sequence, as measured by enzyme or cellular assays. Inappropriate activity could also be due to overexpression of ERAP1 in diseased tissue compared with healthy adjacent tissue.

Preferred diseases or disorders that the compounds described herein may be useful in preventing include proliferative disorders, viral disorders, immune disorders and inflammatory disorders as described hereinbefore.

Thus, the present invention further provides use of compounds as defined herein for the manufacture of medicaments for the treatment of diseases where it is desirable to modulate ERAP1. Such diseases include proliferative disorders, viral disorders, immune disorders and inflammatory disorders as described hereinbefore.

In one preferred embodiment, the compound activates ERAP1's conversion of (L)-leucine-7-amido-4-methylcoumarin (L-AMC) to (L)-leucine and the fluorescent molecule 7-amino-4-methylcoumarin. While the same assay can also identify inhibitors of ERAP1's cleavage of the amide bond in L-AMC, for the purposes of this application this assay is referred to as the "L-AMC activator assay". The potency of any activator is calculated and expressed as the concentration of the activator required to increase the enzyme activity of ERAP1 by 50% over its baseline level (i.e. an $EC_{50}$).

In one preferred embodiment, the compound exhibits an $EC_{50}$ value in an L-AMC activator assay of less than about 25 µM. More preferably, the compound exhibits an $EC_{50}$ value in the L-AMC activator assay of less than about 10 µM, more preferably, less than about 5 µM, even more preferably, less than about 1 µM, even more preferably, less than about 0.1 µM, even more preferably, less than about 0.01 µM. In one preferred embodiment, the compound inhibits ERAP1's ability to hydrolyse the decapeptide substrate WRVYEKCdnpALK. This peptide has minimal fluorescence as the N-terminal tryptophan residue's fluorescence is quenched by the dinitrophenol (DNP) residue within the peptide. However, as ERAP1 hydrolyses the N-terminal amide bond and tryptophan is released this internal quenching is lost and the reaction is monitored by the increase in tryptophan fluorescence over the course of the assay. For the purposes of this application this assay is referred to as the "10 mer inhibition assay" and compound potencies are calculated and expressed as $IC_{50}$ as would be familiar to a person skilled in the art.

In one preferred embodiment, the compound exhibits an $IC_{50}$ value in the 10 mer assay of less than about 25 µM. More preferably, the compound exhibits an $IC_{50}$ value in the 10 mer assay of less than about 10 µM, more preferably, less than about 5 µM, even more preferably, less than about 1 µM, even more preferably, less than about 0.1 µM, even more preferably, less than about 0.01 µM. In one preferred embodiment, the compound exhibits an $IC_{50}$ value in the 10 mer assay of from about 100 nM to about 500 nM, more preferably, less than 100 nM.

Pharmaceutical Compostions

For use according to the present invention, the compounds or physiologically acceptable salt, ester or other physiologically functional derivative thereof, described herein, may be presented as a pharmaceutical formulation, comprising the compounds or physiologically acceptable salt, ester or other physiologically functional derivative thereof, together with one or more pharmaceutically acceptable carriers therefore and optionally other therapeutic and/or prophylactic ingredients. The carrier(s) must be acceptable in the sense of being compatible with the other ingredients of the formulation and not deleterious to the recipient thereof. The pharmaceutical compositions may be for human or animal usage in human and veterinary medicine.

Examples of such suitable excipients for the various different forms of pharmaceutical compositions described herein may be found in the "Handbook of Pharmaceutical Excipients, 2$^{nd}$ Edition, (1994), Edited by A Wade and P J Weller. The carrier, or, if more than one be present, each of the carriers, must be acceptable in the sense of being compatible with the other ingredients of the formulation and not deleterious to the recipient.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant (s), suspending agent(s), coating agent(s), solubilising agent (s), buffer(s), flavouring agent(s), surface active agent(s), thickener(s), preservative(s) (including anti-oxidants) and the like, and substances included for the purpose of rendering the formulation isotonic with the blood of the intended recipient.

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like. Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Pharmaceutical formulations include those suitable for oral, topical (including dermal, buccal and sublingual), rectal or parenteral (including subcutaneous, intradermal, intramuscular and intravenous), nasal and pulmonary administration e.g., by inhalation. The formulation may, where appropriate, be conveniently presented in discrete dosage units and may be prepared by any of the methods well known in the art of pharmacy. All methods include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersible granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active compound is formulated in an appropriate release-controlling matrix or is coated with a suitable release-controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active compound with the softened or melted carrier(s) followed by chilling and shaping in moulds. Pharmaceutical formulations suitable for parenteral administration include sterile solutions or suspensions of an active compound in aqueous or oleaginous vehicles.

Injectable preparations may be adapted for bolus injection or continuous infusion. Such preparations are conveniently presented in unit dose or multi-dose containers which are sealed after introduction of the formulation until required for use. Alternatively, an active compound may be in powder form which is constituted with a suitable vehicle, such as sterile, pyrogen-free water, before use. An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient.

As one possibility such formulations are in the form of finely comminuted powders which may conveniently be presented either in a pierceable capsule, suitably of, for example, gelatin, for use in an inhalation device, or alternatively as a self-propelling formulation comprising an active compound, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active compound is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microlitres, upon each operation thereof.

As a further possibility an active compound may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

Pharmaceutically acceptable carriers are well known to those skilled in the art and include, but are not limited to, 0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Formulations suitable for topical formulation may be provided for example as gels, creams or ointments. Such preparations may be applied e.g. to a wound or ulcer either directly spread upon the surface of the wound or ulcer or carried on a suitable support such as a bandage, gauze, mesh or the like which may be applied to and over the area to be treated.

Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkle with the formulation and then applied to the site to be treated.

According to a further aspect of the invention, there is provided a process for the preparation of a pharmaceutical or veterinary composition as described above, the process comprising bringing the active compound(s) into association with the carrier, for example by admixture.

In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound as described herein into conjunction or association with a pharmaceutically or veterinarily acceptable carrier or vehicle.

Salts/Esters

The compounds of the invention can be present as salts or esters, in particular pharmaceutically and veterinarily acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. hydrohalic acids such as hydrochloride, hydrobromide and hydroiodide, sulphuric acid, phosphoric acid sulphate, bisulphate, hemisulphate, thiocyanate, persulphate and sulphonic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Salts which are not pharmaceutically or veterinarily acceptable may still be valuable as intermediates.

Preferred salts include, for example, acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-naphthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids. More preferably, the salt is a hydrochloride salt.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkane alcohols of 1-12 carbon atoms which may be unsubstituted or substituted, e.g. by a halogen).

Enantiomers/Tautomers

In all aspects of the present invention previously discussed, the invention includes, where appropriate all enantiomers, diastereoisomers and tautomers of the compounds of the invention. The person skilled in the art will recognise compounds that possess optical properties (one or more chiral carbon atoms) or tautomeric characteristics. The corresponding enantiomers and/or tautomers may be isolated/prepared by methods known in the art.

Enantiomers are characterised by the absolute configuration of their chiral centres and described by the R- and S-sequencing rules of Cahn, Ingold and Prelog. Such conventions are well known in the art (e.g. see 'Advanced Organic Chemistry', 3rd edition, ed. March, J., John Wiley and Sons, New York, 1985).

Compounds of the invention containing a chiral centre may be used as a racemic mixture, an enantiomerically enriched mixture, or the racemic mixture may be separated using well-known techniques and an individual enantiomer may be used alone.

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those compounds, and mixtures thereof. The terms used in the claims encompass these forms, provided said forms retain the appropriate functional activity (though not necessarily to the same degree).

The present invention also includes all suitable isotopic variations of the compound or a pharmaceutically acceptable salt thereof. An isotopic variation of a compound of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2$H, $^3$H, $^{13}$C, $^{14}$C, $^{15}$N, $^{17}$O, $^{18}$O, $^{31}$P, $^{32}$P, $^{35}$S, $^{18}$F and $^{36}$Cl, respectively. Certain isotopic variations of the agent and pharmaceutically acceptable salts thereof, for example, those in which a radioactive isotope such as $^3$H or $^{14}$C is incorporated, are useful in drug and/or substrate tissue distribution studies. Tritiated, i.e., $^3$H, and carbon-14, i.e., $^{14}$C, isotopes are particularly preferred for their ease of preparation and detectability. Further, substitution with isotopes such as deuterium, i.e., $^2$H, may afford certain therapeutic advantages resulting from greater metabolic stability, for example, increased in vivo half-life or reduced dosage requirements and hence may be preferred in some circumstances. For example, the invention includes compounds of general formula (I) where any hydrogen atom has been replaced by a deuterium atom. Isotopic variations of the agent of the present invention and pharmaceutically acceptable salts thereof of this invention can generally be prepared by conventional procedures using appropriate isotopic variations of suitable reagents.

Atropisomers

Some of the compounds of the invention may exist as atropisomers. Atropisomers are stereoisomers arising because of hindered rotation about a single bond, where energy differences due to steric strain or other contributors create a barrier to rotation that is high enough to allow for isolation of individual conformers. The invention encompasses all such atropisomers.

Prodrugs

The invention further includes the compounds of the present invention in prodrug form, i.e. covalently bonded compounds which release the active parent drug in vivo. Such prodrugs are generally compounds of the invention wherein one or more appropriate groups have been modified such that the modification may be reversed upon administration to a human or mammalian subject. Reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Solvates

The present invention also includes solvate forms of the compounds of the present invention. The terms used in the claims encompass these forms. Preferably the solvate is a hydrate.

Polymorphs

The invention further relates to the compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Administration

The pharmaceutical compositions of the present invention may be adapted for rectal, nasal, intrabronchial, topical (including buccal and sublingual), vaginal or parenteral (including subcutaneous, intramuscular, intravenous, intraarterial and intradermal), intraperitoneal or intrathecal administration. Preferably the formulation is an orally administered formulation. The formulations may conveniently be presented in unit dosage form, i.e., in the form of discrete portions containing a unit dose, or a multiple or sub-unit of a unit dose. By way of example, the formulations may be in the form of tablets and sustained release capsules, and may be prepared by any method well known in the art of pharmacy.

Formulations for oral administration in the present invention may be presented as: discrete units such as capsules, gellules, drops, cachets, pills or tablets each containing a predetermined amount of the active agent; as a powder or granules; as a solution, emulsion or a suspension of the active agent in an aqueous liquid or a non-aqueous liquid; or as an oil-in-water liquid emulsion or a water-in-oil liquid emulsion; or as a bolus etc. Preferably, these compositions contain from 1 to 250 mg and more preferably from 10-100 mg, of active ingredient per dose.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropyl-methylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

Other forms of administration comprise solutions or emulsions which may be injected intravenously, intraarterially, intrathecally, subcutaneously, intradermally, intraperitoneally or intramuscularly, and which are prepared from sterile or sterilisable solutions. Injectable forms typically contain between 10-1000 mg, preferably between 10-250 mg, of active ingredient per dose.

The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

The dosage amount will further be modified according to the mode of administration of the compound. For example, to achieve an "effective amount" for acute therapy, parenteral administration of a compound is typically preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at a concentration effective to modulate ERAP1. The compounds may be administered one to four times daily at a level to achieve a total daily dose of about 0.4 to about 400 mg/kg/day. The precise amount of an inventive compound which is therapeutically effective, and the route by which such compound is best administered, is readily determined by one of ordinary skill in the art by comparing the blood level of the agent to the concentration required to have a therapeutic effect.

The compounds of this invention may also be administered orally to the patient, in a manner such that the concentration of drug is sufficient to achieve one or more of the therapeutic indications disclosed herein. Typically, a pharmaceutical composition containing the compound is administered at an oral dose of between about 0.1 to about 50 mg/kg in a manner consistent with the condition of the patient. Preferably the oral dose would be about 0.5 to about 20 mg/kg.

No unacceptable toxicological effects are expected when compounds of the present invention are administered in accordance with the present invention. The compounds of this invention, which may have good bioavailability, may be tested in one of several biological assays to determine the concentration of a compound which is required to have a given pharmacological effect.

Combinations

A further aspect of the invention relates to a combination comprising a compound as described herein and one or more additional active agents. In a particularly preferred embodiment, the one or more compounds of the invention are administered in combination with one or more additional active agents, for example, existing drugs available on the market. In such cases, the compounds of the invention may be administered consecutively, simultaneously or sequentially with the one or more other active agents.

Drugs in general are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining chemotherapeutic drugs are that it may promote additive or possible synergistic effects through biochemical interactions and also may decrease the emergence of resistance.

Beneficial combinations may be suggested by studying the activity of the test compounds with agents known or suspected of being valuable in the treatment of a particular disorder. This procedure can also be used to determine the order of administration of the agents, i.e. before, simultaneously, or after delivery. Such scheduling may be a feature of all the active agents identified herein.

In one preferred embodiment, the additional active agent is an immunotherapy agent, more preferably a cancer immunotherapy agent. An "immunotherapy agent" refers to a treatment that uses the subject's own immune system to fight diseases such as cancer.

In one preferred embodiment the compound of the invention inhibits the activity of ERAP1, and the compound is administered in combination with an immunotherapy. The compound may increase the sensitivity of cancer cells to an immunotherapy. The immunotherapy may be mediated by T cells. In one embodiment the compound may increase the number of $CD8^+$ T cells in a tumour.

In one embodiment the compound may be used to treat cancers which are weakly responsive or not responsive to immunotherapies.

In one preferred embodiment, the additional active agent is a molecule capable of immune checkpoint intervention, a co-stimulatory antibody, a chemotherapy agent, a radiotherapy agent, a targeted therapy agent or an antibody, particularly a monoclonal antibody.

In one preferred embodiment the additional active agent is a molecule capable of immune checkpoint intervention.

Immune checkpoint molecules include CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRP, CD47, CD48, 2B4, B7.1, B7.2, ILT-2, ILT-4, TIGIT, HHLA2, IDO, CD39, CD73, A2aR and butyrophilins.

Immune checkpoint molecules include both inhibitory and activatory molecules, and interventions may apply to either or both types of molecule.

Immune checkpoint inhibitors include, but are not limited to, PD-1 inhibitors, PD-L1 inhibitors, LAG-3 inhibitors, TIM-3 inhibitors, TIGIT inhibitors, BTLA inhibitors and CTLA-4 inhibitors, for example. Co-stimulatory antibodies deliver positive signals through immune-regulatory receptors including but not limited to ICOS, CD137, CD27 OX-40 and GITR.

In one highly preferred embodiment, the additional active agent is an antibody checkpoint inhibitor. Suitable examples of antibody checkpoint inhibitors, include, but are not limited to, anti-PD-1 antibodies, anti-PD-L1 antibodies and anti-CTLA4 antibodies.

In one preferred embodiment, the antibody checkpoint inhibitor is an anti-PD-1 antibody, more preferably selected from pembrolizumab, cemiplimab and nivolumab.

In one preferred embodiment, the antibody checkpoint inhibitor is an anti-PD-L1 antibody, more preferably selected from atezolizumab, avelumab and durvalumab.

In one preferred embodiment, the antibody checkpoint inhibitor is an anti-CTLA4 antibody, more preferably selected from ipilimumab and tremelimumab.

In one preferred embodiment the immunotherapy is an anti-cancer vaccine or virus, such as an oncolytic virus.

In one preferred embodiment the immunotherapy is a cell-based therapy. In one embodiment the cell-based therapy may be a T cell therapy, such as adoptive T cell therapy, or therapy with CAR-T cells.

Adoptive cell-based immunotherapy may include the following: Irradiated autologous or allogeneic tumor cells, tumor lysates or apoptotic tumor cells, antigen-presenting cell-based immunotherapy, dendritic cell-based immunotherapy, adoptive T cell transfer, adoptive CAR T cell therapy, autologous immune enhancement therapy (AIET), cancer vaccines, and/or antigen presenting cells. Such cell-based immunotherapies can be further modified to express one or more gene products to further modulate immune responses, for example expressing cytokines such as GM-CSF, and/or to express tumor-associated antigen (TAA) antigens, such as Mage-1, gp-100, patient-specific neoantigen vaccines, and the like.

In a further embodiment, the immunotherapy may comprise non-cell-based immunotherapies. In one embodiment, compositions comprising antigens with or without vaccine-enhancing adjuvants may be used. Such compositions exist in many well-known forms, such as peptide compositions, oncolytic viruses, and recombinant antigen comprising fusion proteins.

In an alternative embodiment, immunomodulatory interleukins, such as IL-2, IL-6, IL-7, IL-12, IL-17, IL-23, as well as modulators thereof (e.g., blocking antibodies or more potent or longer lasting forms) may be used. Immunomodulatory cytokines, such as interferons, G-CSF, imiquimod, T F alpha, and the like, as well as modulators thereof (e.g., blocking antibodies or more potent or longer lasting forms) may also be used. In another embodiment, immunomodulatory chemokines, such as CCL3, CCL26, and CXCL7, and the like, as well as modulators thereof (e.g., blocking antibodies or more potent or longer lasting forms) may be used. In a further embodiment, immunomodulatory molecules targeting immunosuppression, such as STAT3 signaling modulators, FkappaB signaling modulators, and immune checkpoint modulators, may be used.

In another embodiment, immunomodulatory drugs, such as immunocytostatic drugs, glucocorticoids, cytostatics, immunophilins and modulators thereof (e.g., rapamycin, a calcineurin inhibitor, tacrolimus, ciclosporin (cyclosporin), pimecrolimus, abetimus, gusperimus, ridaforolimus, everolimus, temsirolimus, zotarolimus, etc.), hydrocortisone (Cortisol), cortisone acetate, prednisone, prednisolone, methylprednisolone, dexamethasone, betamethasone, triamcinolone, beclometasone, fludrocortisone acetate, deoxycorticosterone acetate (doca) aldosterone, a non-glucocorticoid steroid, a pyrimidine synthesis inhibitor, leflunomide, teriflunomide, a folic acid analog, methotrexate, anti-thymocyte globulin, anti-lymphocyte globulin, thalidomide, lenalidomide, pentoxifylline, bupropion, curcumin, catechin, an opioid, an EVIPDH inhibitor, mycophenolic acid, myriocin, fingolimod, an NF-xB inhibitor, raloxifene, drotrecogin alfa, denosumab, an F-xB signaling cascade inhibitor, disulfiram, olmesartan, dithiocarbamate, a proteasome inhibitor, bortezomib, MG132, Prol, PI-0052, curcumin, genistein, resveratrol, parthenolide, thalidomide, lenalidomide, flavopiridol, non-steroidal anti-inflammatory drugs (NSAIDs), arsenic tri oxide, dehydroxymethylepoxyquinomycin (DH-MEQ), I3C (indole-3-carbinol)/DIM (di-indolmethane) (13C/DIM), Bay 1 1-7082, luteolin, cell permeable peptide SN-50, IKBa-super repressor overexpression, FKB decoy oligodeoxynucleotide (ODN), or a derivative or analog of any thereto, may be used.

In yet another embodiment, immunomodulatory antibodies or protein may be used. For example, antibodies that bind to CD40, Toll-like receptor (TLR), OX40, GITR, CD27, or to 4-IBB, T-cell bispecific antibodies, an anti-IL-2 receptor antibody, an anti-CD3 antibody, OKT3 (muromonab), otelixizumab, teplizumab, visilizumab, an anti-CD4 antibody, clenoliximab, keliximab, zanolimumab, an anti-CDIIa antibody, efalizumab, an anti-CD 18 antibody, erlizumab, rovelizumab, an anti-CD20 antibody, afutuzumab, ocrelizumab, ofatumumab, pascolizumab, rituximab, an anti-CD23 antibody, lumiliximab, an anti-CD40 antibody, teneliximab, toralizumab, an anti-CD40L antibody, ruplizumab, an anti-CD62L antibody, aselizumab, an anti-CD80 antibody, galiximab, an anti-CD147 antibody, gavilimomab, a B-Lymphocyte stimulator (BLyS) inhibiting antibody, belimumab, an CTLA4-Ig fusion protein, abatacept, belatacept, an anti-CTLA4 antibody, ipilimumab, tremelimumab, an anti-eotaxin 1 antibody, bertilimumab, an anti-a4-integrin antibody, natalizumab, an anti-IL-6R antibody, tocilizumab, an anti-LFA-1 antibody, odulimomab, an anti-CD25 antibody, basiliximab, daclizumab, inolimomab, an anti-CD5 antibody, zolimomab, an anti-CD2 antibody, siplizumab, nerelimomab, faralimomab, atlizumab, atorolimumab, cedelizumab, dorlimomab aritox, dorlixizumab, fontolizumab, gantenerumab, gomiliximab, lebrilizumab, maslimomab, morolimumab, pexelizumab, reslizumab, rovelizumab, talizumab, telimomab aritox, vapaliximab, vepalimomab, aflibercept, alefacept, rilonacept, an IL-1 receptor antagonist, anakinra, an anti-IL-5 antibody, mepolizumab, an IgE inhibitor, omalizumab, talizumab, an IL12 inhibitor, an IL23 inhibitor, ustekinumab.

In one embodiment, the subject may be undergoing or have previously undergone treatment with a chemotherapeutic agent. Examples of chemotherapeutic agents include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredepa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-a, Raf, H-Ras, EGFR (e.g., erlotinib (Tarceva)) and VEGF-A that reduce cell proliferation and pharmaceutically acceptable salts, acids or derivatives of any of the above. In addition, the methods of treatment can further include the use of radiation. In addition, the methods of treatment can further include the use of photodynamic therapy.

Process

Another aspect of the invention relates to processes for preparing compounds of formula (I) as described herein.

In one aspect, the invention relates to a process for preparing a compound of formula (I) wherein Z is a piperidin-2-yl group, $R_2$ is $CO_2H$, X is NH, Y is $SO_2$ and $R_1$, $R_3$, $R_4$, $R_6$-$R_9$ are as defined hereinabove, said process comprising the steps of:

(a) reacting a compound of formula I-15 with a boronic acid or boronate ester of formula (i) to form an intermediate of formula I-16;

(b) reacting said intermediate of formula I-16 with a sulfonyl chloride of formula (ii) to form an intermediate of formula I-17;

(c) removing the Boc protecting group from said intermediate of formula I-17 and hydrogenating to form an intermediate of formula I-18; and (d) hydrolysing the ester group in said intermediate of formula I-18 to form a compound of formula I-19:

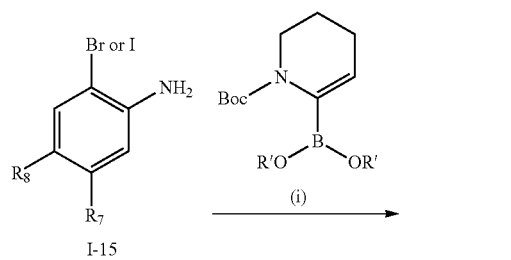

I-15

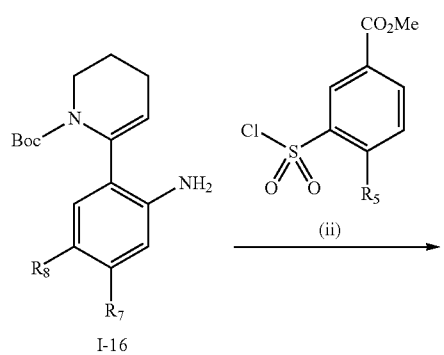

I-16

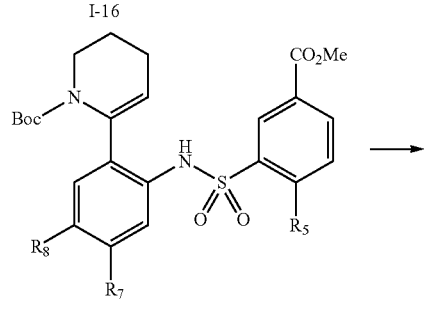

I-17

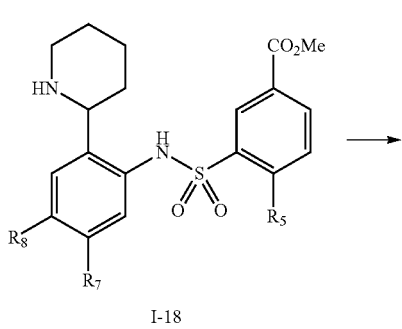

I-18

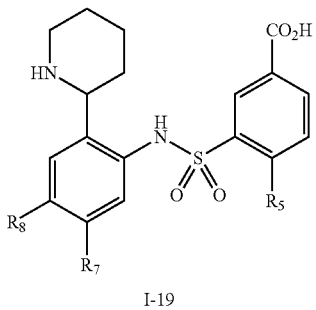

I-19

For ease of reference in the above scheme, the substituents $R_1$, $R_3$, $R_4$, $R_6$ and $R_9$ are omitted. Preferred reagents for each step are set out hereinafter in Scheme 4.

In another aspect, the invention relates to a process for preparing a compound of formula (I) wherein Z is piperidin-3-yl, pyrrolidin-2-yl, cyclopentyl or cyclohexyl, $R_2$ is $CO_2H$, X is NH, Y is $SO_2$ and $R_1$, $R_3$, $R_4$, $R_6$-$R_9$ are as defined hereinabove, said process comprising the steps of:

(a) reacting a bromoaniline compound of formula (iii) with a sulfonyl chloride of formula (ii) to form an intermediate of formula I-1;

(b) reacting said intermediate of formula I-1 with a boronic acid or boronate ester of formula (iv) to form an intermediate of formula I-2;

(c) hydrogenating the intermediate of formula I-2 to form an intermediate of formula I-3; and (d) hydrolysing the ester group in said intermediate of formula I-3 to form a compound of formula I-4:

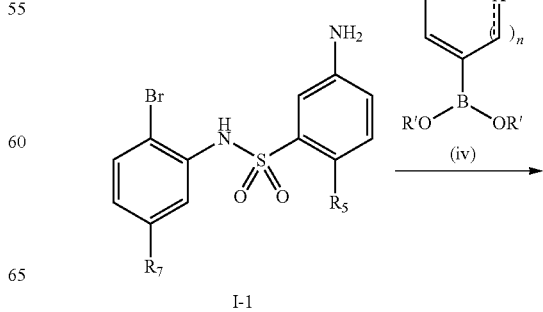

I-1

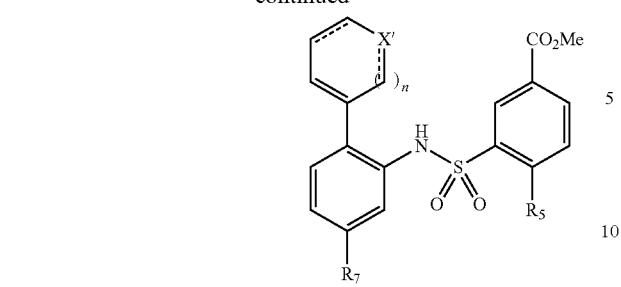

I-2

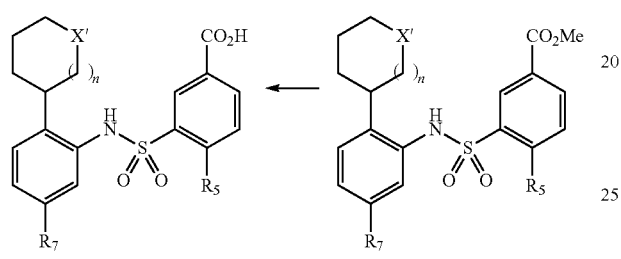

I-4  I-3
X' = N(R₁₄) or C(H)
n = 0 or 1

For ease of reference in the above scheme, the substituents $R_1$, $R_3$, $R_4$, $R_6$, $R_8$ and $R_9$ are omitted. Preferred reagents for each step are set out hereinafter in Scheme 1.

In another aspect, the invention relates to a process for preparing a compound of formula (I) wherein Z is piperidyn-2-yl, $R_2$ is $CO_2H$, X is NH, Y is $SO_2$ and $R_1$, $R_3$, $R_4$, $R_6$-$R_9$ are as defined hereinabove, said process comprising the steps of:

(a) reacting an aryl bromide or iodide of formula I-10 with 2-pyridylzinc(II) bromide to form an intermediate of formula I-11;

(b) reacting said intermediate of formula I-11 with a sulfonyl chloride of formula (ii) as shown above to form an intermediate of formula I-12;

(c) hydrolysing said intermediate of formula I-12 to form an intermediate of formula I-13; and (d) hydrogenating said intermediate of formula I-13 to form a compound of formula I-14:

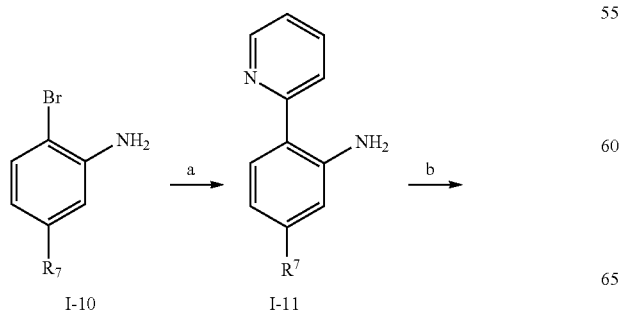

I-10  I-11

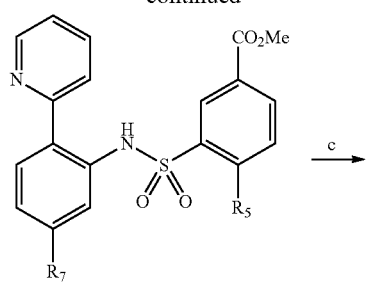

I-12

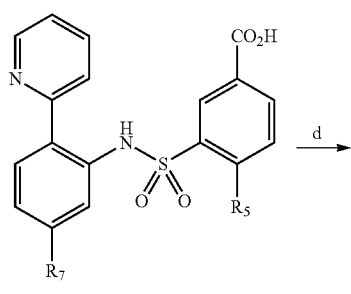

I-13

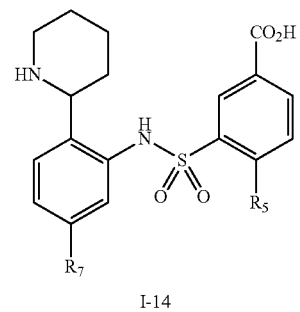

I-14

For ease of reference in the above scheme, the substituents $R_1$, $R_3$, $R_4$, $R_6$, $R_8$ and $R_9$ are omitted. Preferred reagents for each step are set out hereinafter in Scheme 3.

In another aspect, the invention relates to a process for preparing a compound of formula (I) wherein Z is piperidin-2-yl, piperidin-3-yl, pyrrolidin-2-yl, or cyclohexyl, $R_2$ is $CO_2H$, X is NH, Y is $SO_2$ and $R_1$, $R_3$, $R_4$, $R_6$-$R_9$ are as defined hereinabove, said process comprising the steps of:

(a) reacting a compound of formula I-5 with a boronic acid or boronate ester of formula (v) to form an intermediate of formula I-6;

(b) hydrogenating said intermediate of formula I-6 to form an intermediate of formula I-7;

(c) reacting said intermediate of formula I-7 with a sulfonyl chloride of formula (ii) to form an intermediate of formula I-8; and
(d) hydrolysing said intermediate of formula I-8 to form a compound of formula I-9:

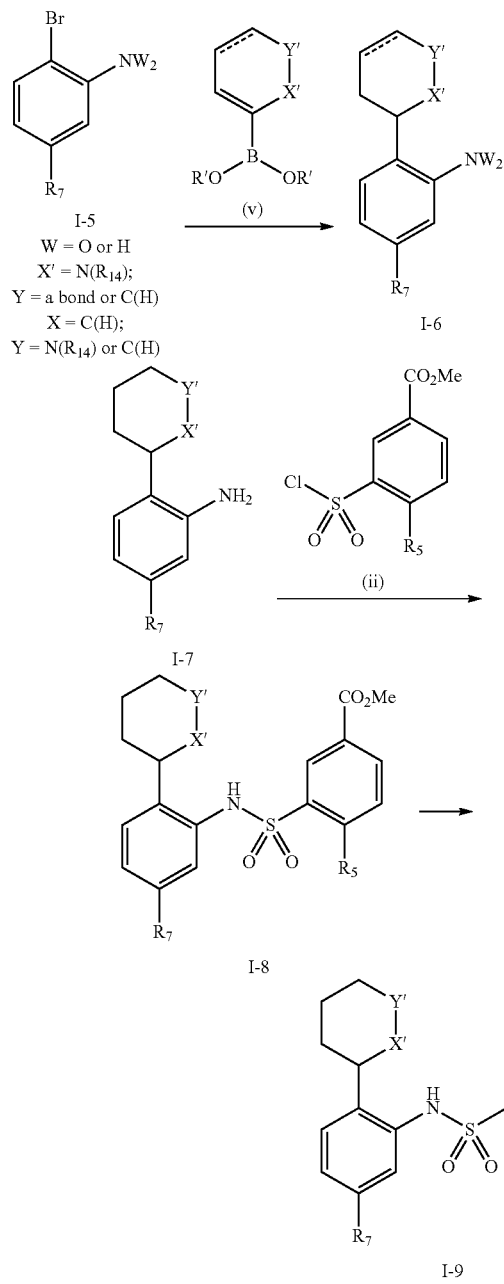

For ease of reference in the above scheme, the substituents $R_1$, $R_3$, $R_4$, $R_6$, $R_8$ and $R_9$ are omitted. Preferred reagents for each step are set out hereinafter in Scheme 2.

The present invention is further described by way of the following non-limiting examples.

EXAMPLES

Where the preparation of starting materials is not described, these are commercially available, known in the literature, or readily obtainable by those skilled in the art using standard procedures. Where it is indicated that compounds were prepared analogously to earlier examples or intermediates, it will be appreciated by the skilled person that the reaction time, number of equivalents of reagents, solvent, concentration and temperature can be modified for each specific reaction and that it may be necessary or desirable to employ different work-up or purification techniques.

General Schemes

ABBREVIATIONS aq: aqueous; br: broad; ca.: circa; d: doublet; DCM: dichloromethane; dioxane: 1,4-dioxane; DMF: dimethylformamide; EtOAc: ethyl acetate; h: hours; HPLC: high performance liquid chromatography; IPA, isopropanol; LC: liquid chromatography; m: multiplet; M: molar, molecular ion; MeCN: acetonitrile; MeOH: methanol; min: minutes; MS: mass spectrometry; NMR: nuclear magnetic resonance; Pd-174: allyl(2-di-tert-butylphosphino-2',4',6'-triisopropyl-1,1'-biphenyl)palladium(II) triflate (CAS: 1798782-25-8); PDA: photodiode array; q: quartet; RT: room temperature (ca. 20° C.); s: singlet, solid; t: triplet; TBME: tert-butyl methyl ether; TFA: trifluoroacetic acid; THF: tetrahydrofuran; UPLC: ultra-performance liquid chromatography; UV: ultraviolet; XPhos Pd G3: (2-Dicyclohexylphosphino-2,4,6-triisopropyl-1,1-biphenyl)[2-(2-amino-1,1-biphenyl)]palladium(II) methanesulfonate (CAS: 1445085-55-1). AcOH: acetic acid; Et$_3$N: triethylamine; PdCl$_2$(AmPhos)$_2$: bis(di-tert-butyl(4-dimethylaminophenyl)phosphine)dichloropalladium(II) (CAS: 887919-35-9); dppf: 1,1-ferrocenediyl-bis(diphenylphosphine)

Other abbreviations are intended to convey their generally accepted meaning.

Scheme 1

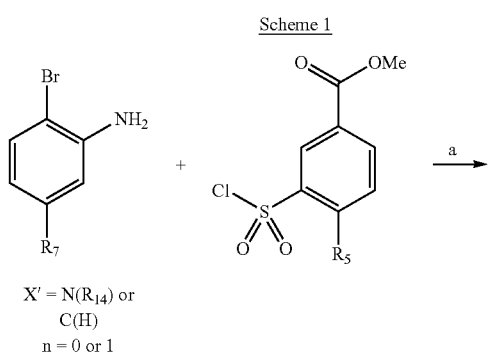

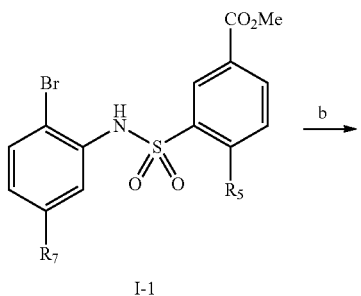

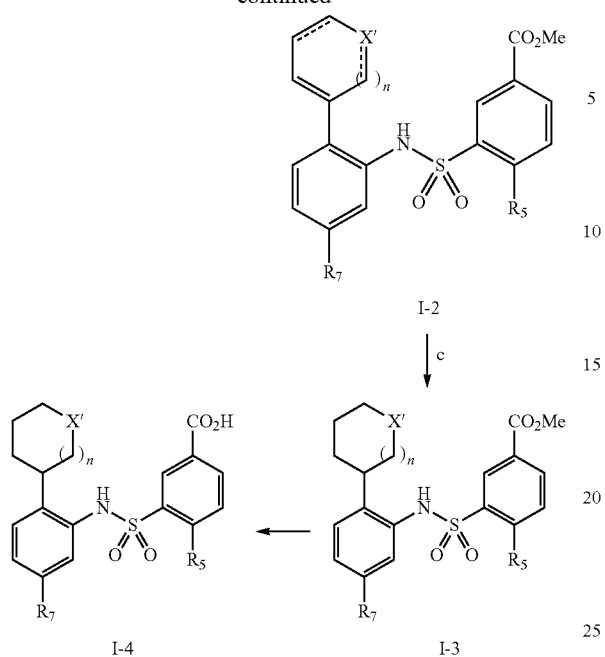

I-2

↓ c

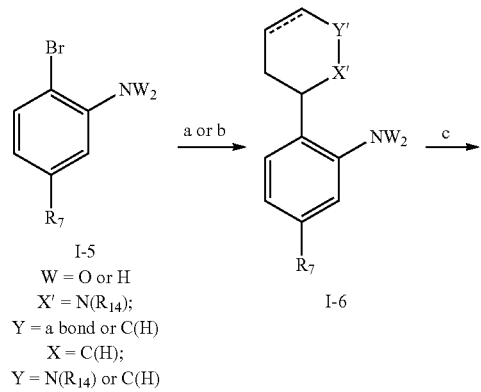

I-4     I-3

Reagents: (a) Pyridine, DCM; (b) Boronic acid/ester, XPhos-Pd-G3, K₃PO₄, dioxane, 80° C.; (c) H₂, Pd/C, EtOH; (d) LiOH, THF, H₂O.

The appropriate aniline and sulfonyl chloride were reacted together to afford sulfonamide I-1. Reaction with the appropriate boronic acid or boronic ester in a Suzuki coupling provided I-2. Catalytic hydrogenation, followed by ester hydrolysis, afforded the corresponding carboxylic acid I-4.

Scheme 2

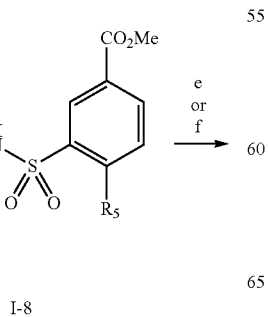

I-5
W = O or H
X′ = N(R₁₄);
Y = a bond or C(H)
X = C(H);
Y = N(R₁₄) or C(H)

I-6

I-7 → I-8

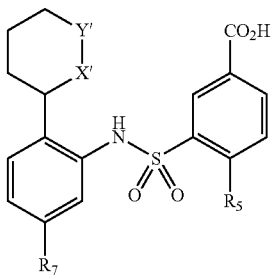

I-9

Reagents: (a) Boronic acid/ester, XPhos-Pd-G3, K₃PO₄, dioxane, water, 80° C.; (b) Organozin(II) bromide, Pd(PPh₃)₄, THF 80° C.; (c) H₂, 10% Pd/C, MeOH; (d) sulfonyl chloride, pyridine, DCM; (e) c. HCl(aq), dioxane, 70° C. (f) LiOH, THF, H₂O, MeOH.

The appropriate aryl bromide (I-5) was reacted with the appropriate boronic acid, boronic ester or organozinc reagent in a Suzuki or Negishi reaction, followed by reduction of the heterocyclic ring and nitro groups in I-6 to afford aniline I-7. This was reacted with the appropriate sulfonyl chloride to afford sulfonamide I-8. Ester hydrolysis provided the corresponding carboxylic acid I-9. Alternatively Scheme 3

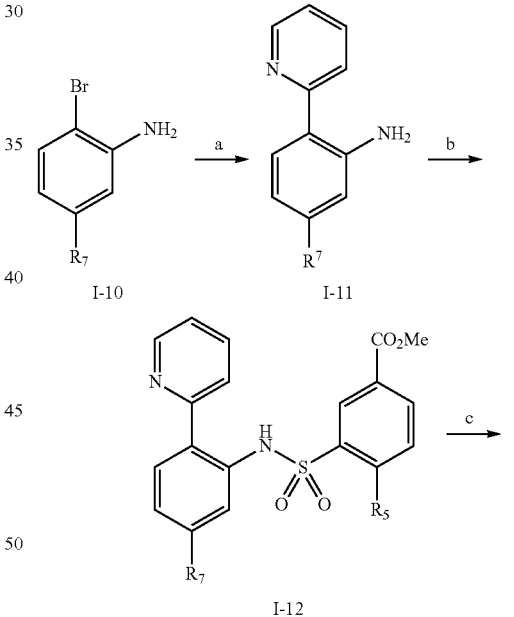

I-10 → I-11 → I-12 → I-13

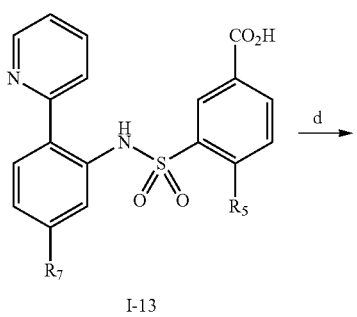

49

-continued

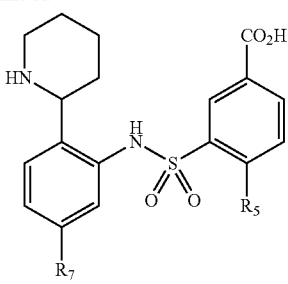

I-14

Reagents: (a) Organozin(II) bromide, Pd(PPh₃)₄, THF, 80° C.; (b) sulfonyl chloride, pyridine, DCM; (c) HCl(aq), dioxane, 70° C.; (d) H₂ 5% Rh/C or 10% PtO₂/C, AcOH, 50° C.

The appropriate aryl bromide or iodide (I-10) was reacted with the appropriate 2-pyridylzinc(II) bromide in a Negishi reaction to afford aniline I-11. This was reacted with the appropriate sulfonyl chloride to afford sulfonamide I-12. Ester hydrolysis provided the corresponding carboxylic acid I-13. The heterocyclic ring was then reduced by catalytic hydrogenation to afford piperidine I-14.

Scheme 4

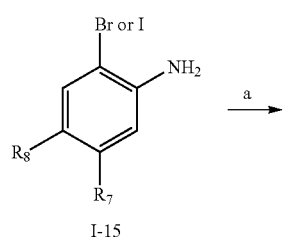

I-15

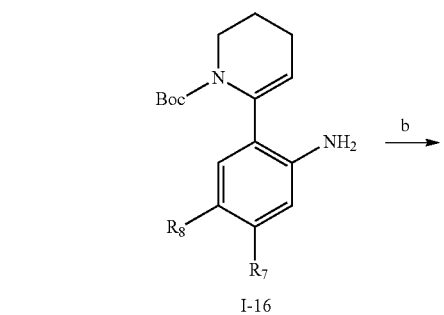

I-16

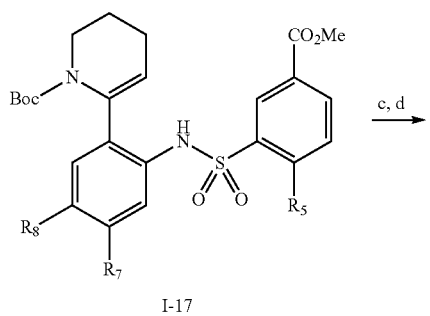

I-17

50

-continued

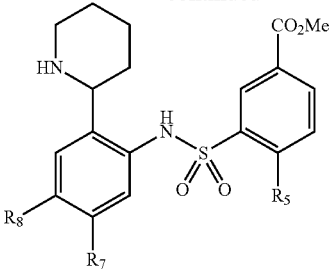

I-18

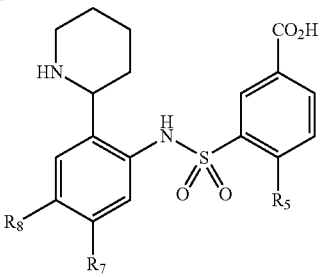

I-19

Reagents: (a) Boronic acid/ester, PdCl₂(AmPhos)₂, K₃PO₄, dioxane, water, 80° C.; (b) sulfonyl chloride, pyridine, DCM; (c) TFA in DCM, RT; (d) Et₃N, NaBH(OAc)₃, THF, RT; (e) LiOH, THF, H₂O, MeOH.

The appropriate aryl bromide or iodide (I-15) was reacted with the appropriate boronic acid, boronic ester reagent in a Suzuki reaction. The aniline product (I-16) was reacted with the appropriate sulfonyl chloride to afford sulfonamide I-17. Removal of the Boc protecting group and reduction of the double bond provided 2-piperidine intermediate (I-18). Ester hydrolysis provided the corresponding carboxylic acid I-19.

EXAMPLES

General Experimental Conditions

All starting materials and solvents were obtained either from commercial sources or prepared according to the literature citation. Reaction mixtures were magnetically stirred and reactions performed at room temperature (ca. 20° C.) unless otherwise indicated.

Column chromatography was performed on an automated flash chromatography system, such as a CombiFlash Rf system, using pre-packed silica (40 μm) cartridges, unless otherwise indicated.

¹H NMR spectra were recorded using a Bruker Avance III HD spectrometer at 500 MHz, equipped with a Bruker 5 mm SmartProbe™. Chemical shifts are expressed in parts per million using either the central peaks of the residual protic solvent or an internal standard of tetramethylsilane as references. The spectra were recorded at 298 K unless otherwise indicated.

Analytical UPLC-MS experiments to determine retention times and associated mass ions were performed using a Waters ACQUITY UPLC® H-Class system, equipped with ACQUITY PDA Detector and ACQUITY QDa Mass Detector, running one of the analytical methods described below.

Analytical LC-MS experiments to determine retention times and associated mass ions were performed using an Agilent 1200 series HPLC system coupled to an Agilent 1956, 6100 or 6120 series single quadrupole mass spectrometer running one of the analytical methods described below.

Preparative HPLC purifications were performed either using a Waters X-Select CSH C18, 5 µm, 19×50 mm column using a gradient of MeCN and water, both modified with 0.1% v/v formic acid, or on a Waters X-Bridge BEH C18, 5 µm, 19×50 mm column using a gradient of MeCN and 10 mM ammonium bicarbonate(aq). Fractions were collected following detection by UV at a single wavelength measured by a variable wavelength detector.

Nomenclature of structures was generated using 'Structure to Name' conversion from ChemDraw® Professional 17 (PerkinElmer).

Separation of Enantiomers by Chiral Chromatography

It will be appreciated that the enantiomers of the compounds described above can be isolated using techniques well known in the art, including, but not limited to, chiral chromatography.

Analytical Methods

Method 1—Acidic 3 Min Method

Column: Waters ACQUITY UPLC® CSH C18, 1.7 µm, 2.1×30 mm at 40° C.

Detection: UV at 254 nm unless otherwise indicated, MS by electrospray ionisation Solvents: A: 0.1% v/v Formic acid in water, B: 0.1% v/v Formic acid in MeCN Gradient:

| Time | % A | % B | Flow rate (ml/min) |
|------|-----|-----|--------------------|
| 0.00 | 95 | 5 | 0.77 |
| 0.11 | 95 | 5 | 0.77 |
| 2.15 | 5 | 95 | 0.77 |
| 2.56 | 5 | 95 | 0.77 |
| 2.83 | 95 | 5 | 0.77 |
| 3.00 | 95 | 5 | 0.77 |

Method 2—Basic 3 Min Method

Column: Waters ACQUITY UPLC® BEH C18, 1.7 µm, 2.1×30 mm at 40° C.

Solvents: A: 10 mM ammonium bicarbonate(aq), B: MeCN (other parameters the same as Method 1)

Method 3—Acidic 4 Min Method

Column: Waters X-Select CSH C18, 2.5 µm, 4.6×30 mm at 40° C.

Detection: UV at 254 nm unless otherwise indicated, MS by electrospray ionisation Solvents: A: 0.1% v/v Formic acid in water, B: 0.1% v/v Formic acid in MeCN Gradient:

| Time | % A | % B | Flow rate (ml/min) |
|------|-----|-----|--------------------|
| 0.0 | 95.0 | 5.0 | 2.5 |
| 3.0 | 5.0 | 95.0 | 2.5 |
| 3.01 | 5.0 | 95.0 | 4.5 |
| 3.6 | 5.0 | 95.0 | 4.5 |
| 3.7 | 95.0 | 5.0 | 2.5 |
| 4.0 | 95.0 | 5.0 | 2.5 |

Method 4—Basic 4 Min Method

Column: Waters X-Bridge BEH C18, 2.5 µm, 4.6×30 mm at 40° C.

Solvents: A: 10 mM ammonium bicarbonate(aq), B: MeCN (other parameters the same as Method 3)

Method 5—Acidic 1 Min Method

Column: Waters ACQUITY UPLC® CSH C18, 1.7 µm, 2.1×30 mm at 40° C.

Detection: UV at 254 nm unless otherwise indicated, MS by electrospray ionisation Solvents: A: 0.1% v/v Formic acid in water, B: 0.1% v/v Formic acid in MeCN Gradient:

| Time | % A | % B | Flow rate (ml/min) |
|------|-----|-----|--------------------|
| 0.00 | 95 | 5 | 1.00 |
| 0.08 | 95 | 5 | 1.00 |
| 0.70 | 5 | 95 | 1.00 |
| 0.80 | 5 | 95 | 1.00 |
| 0.90 | 95 | 5 | 1.00 |
| 1.00 | 95 | 5 | 1.00 |

Method 6—Basic 1 Min Method

Column: Waters ACQUITY UPLC® BEH C18, 1.7 µm, 2.1×30 mm at 40° C.

Solvents: A: 10 mM ammonium bicarbonate(aq), B: MeCN (other parameters the same as Method 5)

In the following section, the Examples are racemic at the single chiral centre, otherwise, E1 and E2 refer to separated enantiomers 1 and 2 of undefined absolute configuration.

Example 1: 4-methoxy-3-(N-(2-(1-methylpiperidin-3-yl)-5-(trifluoromethyl)phenyl)sulfamoyl)benzoic Acid

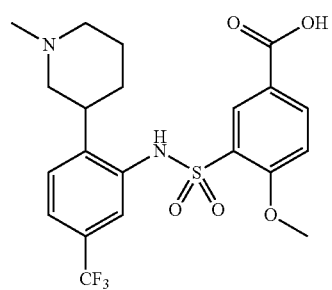

Step 1: 1-methyl-5-(2-nitro-4-(trifluoromethyl)phenyl)-1,2,3,6-tetrahydropyridine: A mixture of 1-bromo-2-nitro-4-(trifluoromethyl)benzene (0.172 ml, 1.12 mmol), 1-methyl-5-(4,4,5,5-tetramethyl-1,3,2-dioxaborolan-2-yl)-1,2,3,6-tetrahydropyridine (250 mg, 1.12 mmol) and $K_3PO_4$(s) (714 mg, 3.36 mmol) in dioxane (4 ml) and water (1 ml) was sparged with $N_2$ for 15 min. XPhos Pd G3 (44.1 mg, 0.056 mmol) was added and the mixture was sparged with $N_2$ for 5 min and then heated to 80° C. and stirred for 2 h. The mixture was diluted with water (10 ml) and extracted with EtOAc (3×20 ml). The organic extracts were combined and washed with brine (2×20 ml), dried by passage through a phase separator, and the solvent was removed in vacuo. The residue was loaded onto silica and purified by chromatography on silica gel (12 g cartridge, 0-10% MeOH/DCM) to afford the title compound (0.141 g, 0.483 mmol, 43% yield, 98% purity) as a dark brown oil. UPLC-MS (Method 1): m/z 287.2 (M+H)$^+$ at 0.68 min.

Step 2: 2-(1-methylpiperidin-3-yl)-5-(trifluoromethyl) aniline: The product from Step 1 above (0.141 g, 0.483 mmol, 98% purity) was dissolved in MeOH (12 ml) and 4% Pd/C (Type 39) (0.125 g, 0.049 mmol) was added and the reaction mixture was stirred at RT under $H_2$ (3 bar pressure) for 3 h. The mixture was filtered through Celite® and the solvent removed in vacuo. The residue was purified by chromatography on silica gel (12 g cartridge, 0-10% MeOH/DCM) to afford the title compound (91 mg, 0.352 mmol, 73% yield) as a yellow solid. UPLC-MS (Method 1): m/z 259.2 (M+H)$^+$ at 0.65 min.

Step 3: methyl 4-methoxy-3-(N-(2-(1-methylpiperidin-3-yl)-5-(trifluoromethyl)phenyl)sulfamoyl)benzoate: Pyridine (85 µl, 1.05 mmol) was added to a solution of the product from Step 2 above (90 mg, 0.348 mmol) and methyl 3-(chlorosulfonyl)-4-methoxybenzoate (0.111 g, 0.418 mmol) in DCM (8 ml) and the resultant solution was stirred at RT for 18 h. The solution was concentrated in vacuo and the residue purified by chromatography on silica gel (24 g cartridge, 0-100% EtOAc/isohexane) to afford the title compound (0.157 g, 0.278 mmol, 80% yield, 86% purity) as a white solid. UPLC-MS (Method 1): m/z 487.3 (M+H)$^+$, 485.2 (M−H)$^-$, at 0.92 min.

Step 4: 4-methoxy-3-(N-(2-(1-methylpiperidin-3-yl)-5-(trifluoromethyl)phenyl)sulfamoyl)benzoic acid: conc. HCl (aq) (3 ml, 99 mmol) was added to a mixture of the product from Step 3 above (0.157 g, 0.278 mmol) in dioxane (8 ml) and water (1 ml) and the resultant mixture was heated at 70° C. for 72 h. The solution was concentrated in vacuo and the residue was purified by chromatography on silica gel (12 g cartridge, 0-10% MeOH/DCM) to afford the title compound (18 mg, 0.038 mmol, 14% yield, 99% purity) as an off white solid. UPLC-MS (Method 1): m/z 473.2 (M+H)$^+$, 471.2 (M−H)$^-$ at 0.78 min. $^1$H NMR (500 MHz, DMSO-d$_6$) δ 13.07 (br s, 1H), 9.95 (br s, 1H), 8.17 (dd, J=8.7, 2.2 Hz, 1H), 8.14 (d, J=2.2 Hz, 1H), 7.63 (s, 2H), 7.38 (d, J=8.8 Hz, 1H), 7.05 (s, 1H), 3.91 (s, 3H), 3.71-3.58 (m, 1H), 3.49-3.36 (m, 1H), 3.29-3.20 (m, 1H), 3.20-3.03 (m, 1H), 3.03-2.87 (m, 1H), 2.74 (s, 3H), 1.99-1.85 (m, 1H), 1.83-1.69 (m, 1H), 1.69-1.50 (m, 2H).

Example 2: 4-methoxy-3-(N-(2-(piperidin-3-yl)-5-(trifluoromethyl)phenyl)sulfamoyl)benzoic Acid Hydrochloride

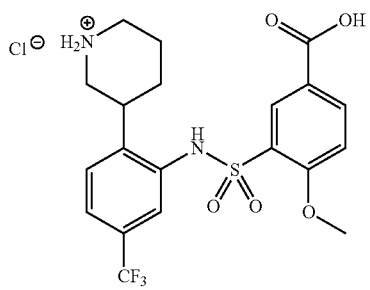 [SMILES: [Cl-] ; COc1ccc(C(=O)O)cc1S(=O)(=O)Nc1cc(C(F)(F)F)ccc1C1CCC[NH2+]C1]

Step 1: tert-butyl 3-(2-nitro-4-(trifluoromethyl)phenyl)-5,6-dihydropyridine-1(2H)-carboxylate: A mixture of 1-bromo-2-nitro-4-(trifluoromethyl)benzene (0.396 ml, 2.59 mmol), tert-butyl 3-(4,4,5,5-tetramethyl-1,3,2-dioxaborolan-2-yl)-5,6-dihydropyridine-1(2H)-carboxylate (0.800 g, 2.59 mmol) and K$_3$PO$_4$(s) (1.65 g, 7.76 mmol) in dioxane (4 ml) and water (1 ml) was sparged with N$_2$ for 15 min. XPhos Pd G3 (0.102 g, 0.129 mmol) was added and the mixture was sparged with N$_2$ for 5 min and then heated at 80° C. for 2 h. The mixture was cooled and diluted with water (10 ml), then extracted with EtOAc (3×20 ml). The organic extracts were combined and washed with brine (2×20 ml), dried by passage through a phase separator and the solvent was removed in vacuo. The residue was loaded onto silica and purified by chromatography on silica gel (12 g cartridge, 0-50% EtOAc/isohexane) to afford the title compound (0.837 g, 2.23 mmol, 86% yield, 99% purity) as a dark brown oil. UPLC-MS (Method 1): m/z 272.9 (M+H−Boc)$^+$ at 1.83 min.

Step 2: tert-butyl 3-(2-amino-4-(trifluoromethyl)phenyl)piperidine-1-carboxylate: The product from Step 1 above (0.837 g, 2.23 mmol, 99% purity) was dissolved in MeOH (22.5 ml) and 10% Pd/C (Type 39) (0.570 g, 0.268 mmol) was added. The reaction mixture was stirred at RT under H$_2$ (3 bar) for 4 h. The mixture was filtered through Celite®, washing with MeOH (20 ml), and the solvent was removed in vacuo. The residue was purified by chromatography on silica gel (12 g cartridge, 0-50% EtOAc/isohexane) to afford the title compound (0.569 g, 1.47 mmol, 66% yield, 89% purity) as a white solid. UPLC-MS (Method 1): m/z 245.2 (M+H−Boc)$^+$ at 1.77 min.

Step 3: tert-butyl 3-(2-(2-methoxy-5-(methoxycarbonyl)phenylsulfonamido)-4-(trifluoromethyl)phenyl)piperidine-1-carboxylate: Pyridine (0.141 ml, 1.74 mmol) was added to a solution of the product from Step 2 above (0.2 g, 0.517 mmol, 89% purity) and methyl 3-(chlorosulfonyl)-4-methoxybenzoate (0.184 g, 0.697 mmol) in DCM (8 ml) and the resultant solution was stirred at RT for 18 h. The solution was concentrated in vacuo and the residue was purified by chromatography on silica gel (24 g cartridge, 0-100% EtOAc/isohexane) to afford the title compound (0.301 g, 0.505 mmol, 98% yield, 96% purity) as a white solid. UPLC-MS (Method 1): m/z 473.3 (M+H−Boc)$^+$, 571.2 (M−H)$^-$ at 1.78 min.

Step 4: 4-methoxy-3-(N-(2-(piperidin-3-yl)-5-(trifluoromethyl)phenyl)sulfamoyl)benzoic acid hydrochloride: conc. HCl(aq) (3 ml, 99 mmol) was added to the product from Step 3 above (0.301 g, 0.505 mmol, 96% purity) in dioxane (8 ml) and water (1 ml) and the resultant mixture was heated at 70° C. for 72 h. The solution was concentrated in vacuo and the residue azeotroped with toluene (2×40 ml). The residue was triturated with MeCN and filtered to afford the title compound (0.156 g, 0.312 mmol, 62% yield, 99% purity) as an off white solid. UPLC-MS (Method 1): m/z 459.2 (M+H)$^+$, 457.2 (M−H)$^-$ at 0.78 min. $^1$H NMR (500 MHz, DMSO-d$_6$) δ 13.12 (s, 1H), 9.88 (s, 1H), 9.28 (s, 1H), 8.59 (s, 1H), 8.18 (dd, J=8.7, 2.2 Hz, 1H), 8.12 (d, J=2.2 Hz, 1H), 7.71 (d, J=8.2 Hz, 1H), 7.65-7.60 (m, 1H), 7.39 (d, J=8.8 Hz, 1H), 6.96 (d, J=2.0 Hz, 1H), 3.91 (s, 3H), 3.68-3.56 (m, 1H), 3.30-3.23 (m, 1H), 3.22-3.14 (m, 1H), 3.11-3.00 (m, 1H), 3.00-2.88 (m, 1H), 1.94-1.83 (m, 1H), 1.78-1.60 (m, 3H).

Example 3: 4-ethyl-3-(N-(2-(piperidin-3-yl)-5-(trifluoromethyl)phenyl)sulfamoyl)benzoic Acid Hydrochloride

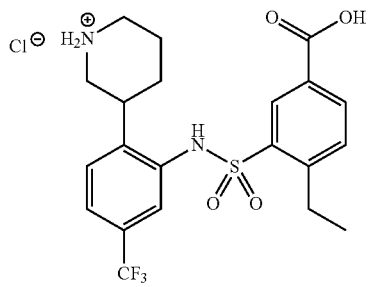 [SMILES: [Cl-] ; CCc1ccc(C(=O)O)cc1S(=O)(=O)Nc1cc(C(F)(F)F)ccc1C1CCC[NH2+]C1]

Step 1: 3-(chlorosulfonyl)-4-ethylbenzoic acid: 4-ethylbenzoic acid (7 g, 46.6 mmol) in chlorosulfonic acid (20 ml, 299 mmol) was heated to 100° C. for 5 h. The mixture was cooled and carefully added to stirred ice-water (200 ml). The resultant precipitate was collected by filtration, washed with water (100 ml) and dried in vacuo to give the title compound (10.9 g, 41.5 mmol, 89% yield, 95% purity) as a white solid. $^1$H NMR (500 MHz, DMSO-$d_6$) δ 13.65 (br s, 1H), 8.34 (d, J=1.9 Hz, 1H), 7.82 (dd, J=7.9, 2.0 Hz, 1H), 7.32 (d, J=7.9 Hz, 1H), 3.08 (q, J=7.5 Hz, 2H), 1.18 (t, J=7.5 Hz, 3H).

Step 2: methyl 3-(chlorosulfonyl)-4-ethylbenzoate: Thionyl chloride (10 ml, 137 mmol) was added portionwise to the product from step 1 above (4 g, 16.1 mmol, 95% purity) at RT. The mixture was heated to 75° C. for 2 h, cooled to RT, concentrated in vacuo and azeotroped with toluene. The solid was dissolved in DCM (10 ml) and treated with MeOH (0.716 ml, 17.7 mmol) followed by Et$_3$N (2.41 ml, 17.7 mmol) and stirred at RT overnight. The mixture was diluted with DCM (50 ml), washed with water (50 ml), dried (MgSO$_4$) and concentrated in vacuo. The crude product was purified by chromatography on silica gel (40 g cartridge, 0-50% EtOAc/isohexane) to afford the title compound (3.60 g, 13.0 mmol, 81% yield, 95% purity) as a white solid. $^1$H NMR (500 MHz, DMSO-$d_6$) δ 8.74 (d, J=1.8 Hz, 1H), 8.32 (dd, J=8.0, 1.8 Hz, 1H), 7.61 (d, J=8.0 Hz, 1H), 3.99 (s, 3H), 3.28 (q, J=7.5 Hz, 2H), 1.41 (t, J=7.5 Hz, 3H).

Step 3: tert-butyl 3-(2-(2-ethyl-5-(methoxycarbonyl)phenylsulfonamido)-4-(trifluoromethyl)phenyl)piperidine-1-carboxylate: Pyridine (0.141 ml, 1.74 mmol) was added to a solution of the product from Example 2 Step 2 (0.2 g, 0.517 mmol, 89% purity) and the product from Step 2 above (0.183 g, 0.662 mmol, 95% purity) in DCM (8 ml) and the resultant solution was stirred at RT for 18 h. The solution was concentrated in vacuo and the residue was purified by chromatography on silica gel (24 g cartridge, 0-100% EtOAc/isohexane) to afford the title compound (0.196 g, 0.302 mmol, 58% yield, 88% purity) as a white solid. UPLC-MS (Method 1): m/z 471.3 (M+H–Boc)$^+$, 569.3 (M–H)$^-$ at 1.93 min.

Step 4: 4-ethyl-3-(N-(2-(piperidin-3-yl)-5-(trifluoromethyl)phenyl)sulfamoyl)benzoic acid hydrochloride: conc. HCl(aq) (3 ml, 99 mmol) was added to the product from Step 3 above (0.196 g, 0.302 mmol, 88% purity) in dioxane (8 ml) and water (1 ml) and the mixture was heated at 70° C. for 72 h. The solution was concentrated in vacuo and the residue azeotroped with toluene (2×40 ml). The residue was triturated with MeCN and filtered to afford the title compound (94 mg, 0.187 mmol, 62% yield, 98% purity) as an off white solid. UPLC-MS (Method 1): m/z 457.3 (M+H)$^+$, 455.3 (M–H)$^-$ at 0.95 min.

$^1$H NMR (500 MHz, DMSO-$d_6$) δ 13.30 (s, 1H), 10.26 (s, 1H), 9.38-9.20 (m, 1H), 8.71-8.52 (m, 1H), 8.18 (d, J=1.8 Hz, 1H), 8.11 (dd, J=8.0, 1.9 Hz, 1H), 7.72 (d, J=8.2 Hz, 1H), 7.66 (d, J=7.9 Hz, 1H), 7.63 (d, J=8.1 Hz, 1H), 6.78 (d, J=2.0 Hz, 1H), 3.56-3.45 (m, 1H), 3.30-3.21 (m, 1H), 3.21-3.12 (m, 1H), 3.11-2.99 (m, 1H), 2.99-2.83 (m, 3H), 1.91-1.79 (m, 1H), 1.74-1.59 (m, 2H), 1.54-1.42 (m, 1H), 1.16 (t, J=7.4 Hz, 3H).

Example 4: 3-(N-(2-cyclohexyl-5-(tetrazol-1-yl)phenyl)sulfamoyl)-4-ethylbenzoic Acid

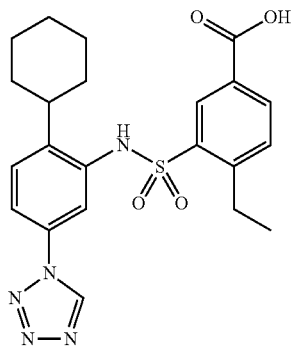 [SMILES: CCc1ccc(C(=O)O)cc1S(=O)(=O)Nc1cc(-n2cnnn2)ccc1C1CCCCC1]

Step 1: 1-(4-bromo-3-nitrophenyl)tetrazole: A mixture of 4-bromo-3-nitroaniline (3 g, 13.8 mmol) and triethyl orthoformate (11.5 ml, 69.1 mmol) in acetic acid (54 ml) was stirred at 80° C. for 1 h. Trimethylsilyl azide (2.40 ml, 18.1 mmol) was added dropwise and the resultant mixture was stirred at 80° C. for 3.5 h. Additional trimethylsilyl azide (0.367 ml, 2.76 mmol) was added and the mixture was stirred at 80° C. for 1 h. The mixture was allowed to cool to RT, concentrated in vacuo, and the residue was azeotroped with toluene (100 ml) to afford the crude product as a dark yellow solid. The crude product was purified by chromatography on silica gel (40 g cartridge, 0-2.5% MeOH/DCM) to afford the title compound (3.3 g, 12.0 mmol, 87% yield, 98% purity) as a yellow solid. UPLC-MS (Method 1): m/z no ionisation at 1.12 min. $^1$H NMR (500 MHz, DMSO-$d_6$) δ 10.20 (s, 1H), 8.70 (d, J=2.5 Hz, 1H), 8.24 (d, J=8.7 Hz, 1H), 8.19 (dd, J=8.7, 2.5 Hz, 1H).

Step 2: 2-bromo-5-(tetrazol-1-yl)aniline: Zinc dust (2.72 g, 41.7 mmol) and NH$_4$Cl(s) (2.23 g, 41.7 mmol) were added to the product from Step 1 above (1.5 g, 5.44 mmol, 98% purity) in THF (45 ml) and water (15 ml) and the resultant mixture was stirred at RT for 4 h. The reaction mixture was filtered through Celite®, washing with THF (50 ml). The filtrate was concentrated in vacuo and slurried in DCM (30 ml). MeOH (40 ml) was added and the resultant cloudy solution was dried by passage through a phase separator and concentrated in vacuo to afford the title compound (1.63 g) as a light brown solid. UPLC-MS (Method 1): m/z 240.1 (M+H)$^+$, 238.1 (M–H)$^-$, at 0.98 min. $^1$H NMR (500 MHz, DMSO-$d_6$) δ 10.02 (s, 1H), 7.60 (d, J=8.5 Hz, 1H), 7.30 (d, J=2.6 Hz, 1H), 6.97 (dd, J=8.5, 2.6 Hz, 1H), 5.86 (s, 2H).

Step 3: methyl 3-(N-(2-bromo-5-(tetrazol-1-yl)phenyl)sulfamoyl)-4-ethylbenzoate: A solution of the product from Step 2 above (500 mg) and the product from Example 3 Step 2 (494 mg, 1.79 mmol, 95% purity) in pyridine (3 ml) was stirred at RT for 17 h. The reaction mixture was concentrated in vacuo, azeotroped with toluene (2×50 ml) and then the residue was dry loaded onto Celite®. The crude product was partially purified by chromatography on silica gel (24 g cartridge, 50% EtOAc/isohexane), then partially purified by chromatography on silica gel (24 g cartridge, 0-1.5% MeOH/DCM), then purified by chromatography (24 g reverse phase C18 cartridge, 15-65% MeCN/0.1% formic acid(aq)) to afford the title compound (348 mg, 0.724 mmol, 43% yield over 2 steps, 97% purity) as a pale orange solid. UPLC-MS (Method 1): m/z 466.1 (M+H)$^+$, 464.1 (M–H)$^-$, at 0.64 min. $^1$H NMR (500 MHz, DMSO-$d_6$) δ 10.65 (br s, 1H), 10.11 (s, 1H), 8.28 (d, J=1.9 Hz, 1H), 8.12 (dd, J=8.0, 1.9 Hz, 1H), 7.88 (d, J=8.7 Hz, 1H), 7.85 (d, J=2.6 Hz, 1H), 7.77-7.69 (m, 1H), 7.65 (d, J=8.1 Hz, 1H), 3.82 (s, 3H), 3.08 (q, J=7.4 Hz, 2H), 1.23 (t, J=7.4 Hz, 3H).

Step 4: methyl 3-(N-(4-(tetrazol-1-yl)-2',3',4',5'-tetrahydro-[1,1'-biphenyl]-2-yl)sulfamoyl)-4-ethylbenzoate: A mixture of the product from Step 3 above (100 mg, 0.208 mmol, 97% purity), 2-(cyclohex-1-en-1-yl)-4,4,5,5-tetramethyl-1,3,2-dioxaborolane (60 μl, 0.279 mmol), 1 M $K_3PO_4$ (aq) (0.358 ml, 0.358 mmol) and dioxane (2.1 ml) was treated with XPhos Pd G3 (10 mg, 0.012 mmol). The resultant mixture was degassed with $N_2$ for 15 min and then heated at 80° C. for 17 h. Additional XPhos Pd G3 (20 mg, 0.024 mmol) and 2-(cyclohex-1-en-1-yl)-4,4,5,5-tetramethyl-1,3,2-dioxaborolane (0.09 ml, 0.419 mmol) were added, the mixture was degassed with $N_2$ for 10 min and then heated at 80° C. for 3 h. The mixture was allowed to cool to RT and was filtered through Celite®, washing with MeOH (10 ml), and the filtrate concentrated in vacuo. The residue was purified by chromatography on silica gel (12 g cartridge, 0-50% EtOAc/isohexane) to afford the title compound (78 mg, 0.132 mmol, 63% yield, 79% purity) as a yellow oil. UPLC-MS (Method 1): m/z 468.4 (M+H)$^+$, 466.3 (M−H)$^−$, at 1.70 min. $^1$H NMR (500 MHz, DMSO-$d_6$) δ 10.07 (s, 1H), 10.00 (s, 1H), 8.26 (d, J=1.9 Hz, 1H), 8.11 (dd, J=8.0, 1.9 Hz, 1H), 7.75-7.69 (m, 2H), 7.65 (d, J=8.1 Hz, 1H), 7.33 (d, J=8.2 Hz, 1H), 5.40-5.16 (m, 1H), 3.82 (s, 3H), 3.04 (q, J=7.4 Hz, 2H), 1.95-1.86 (m, 4H), 1.56-1.40 (m, 4H), 1.21 (t, J=7.4 Hz, 3H).

Step 5: methyl 3-(N-(2-cyclohexyl-5-(tetrazol-1-yl)phenyl)sulfamoyl)-4-ethylbenzoate: 5% Pd/C (Type 87L) (70.1 mg, 0.013 mmol) was added to a solution of the product from Step 4 above (78 mg, 0.132 mmol, 79% purity) in EtOH (3 ml). The reaction mixture was stirred at RT under $H_2$ (3 bar) for 18 h. The reaction mixture was filtered through Celite®, washing with MeOH (25 ml) and the filtrate was concentrated in vacuo to afford the title compound (37 mg, 0.077 mmol, 59% yield, 98% purity) as an off-white solid. UPLC-MS (Method 1): m/z 470.4 (M+H)$^+$, 468.3 (M−H)$^−$, at 1.67 min.

Step 6: 3-(N-(2-cyclohexyl-5-(tetrazol-1-yl)phenyl)sulfamoyl)-4-ethylbenzoic acid: 1 M LiOH(aq) (0.315 ml, 0.315 mmol) was added to a solution of the product from Step 5 above (37 mg, 0.077 mmol, 98% purity) in THF (0.63 ml) at RT. The resultant mixture was stirred at RT for 20 h. The mixture was concentrated in vacuo and the residue dissolved in water (2 ml) and washed with EtOAc (2 ml). The aqueous phase was acidified using 1 M HCl(aq) to pH 4-5 and then extracted with EtOAc (3×2 ml). The organic phases were combined and dried over $MgSO_4$, filtered, and then concentrated in vacuo to afford the title compound (17.1 mg, 0.034 mmol, 44% yield, 90% purity) as an off-white solid. UPLC-MS (Method 1): m/z 456.3 (M+H)$^+$, 454.3 (M−H)$^−$, at 1.51 min.

$^1$H NMR (500 MHz, DMSO-$d_6$) δ 13.24 (br s, 1H), 10.33 (br s, 1H), 10.05 (s, 1H), 8.21 (d, J=1.8 Hz, 1H), 8.06 (dd, J=8.0, 1.9 Hz, 1H), 7.77-7.67 (m, 2H), 7.62 (d, J=8.0 Hz, 1H), 7.46 (d, J=8.4 Hz, 1H), 3.07 (q, J=7.4 Hz, 2H), 1.64-1.54 (m, 3H), 1.30-0.91 (m, 11H).

Example 5: 4-ethyl-3-(N-(2-(pyrrolidin-2-yl)-5-(trifluoromethyl)phenyl)sulfamoyl)benzoic Acid

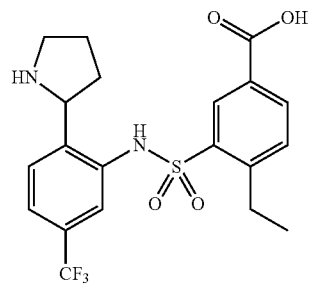 [SMILES: CCc1ccc(C(=O)O)cc1S(=O)(=O)Nc1cc(C(F)(F)F)ccc1C1CCCN1]

Step 1: methyl 3-(N-(2-bromo-5-(trifluoromethyl)phenyl)sulfamoyl)-4-ethylbenzoate: A solution of 2-bromo-5-(trifluoromethyl)aniline (2 g, 8.33 mmol) in DCM (10 ml) and pyridine (4.04 ml, 50.0 mmol) was added to a solution of the product from Example 3 Step 2 (2.19 g, 7.92 mmol, 95% purity) in DCM (10 ml) and the resultant solution was stirred at RT for 3 days.

In a separate vessel, a solution of 2-bromo-5-(trifluoromethyl)aniline (4 g, 16.7 mmol) in DCM (10 ml) and pyridine (8.09 ml, 100 mmol) was added to a solution of the product from Example 3 Step 2 (4.38 g, 15.8 mmol, 95% purity) in DCM (10 ml). The resultant solution was stirred at RT for 3 days.

The two reaction mixtures were combined and concentrated in vacuo. The residue was partially purified by chromatography on silica gel (120 g cartridge, 0-50% EtOAc/isohexane), then purified by chromatography on silica gel (120 g cartridge, 0-50% DCM/isohexane) to afford the title compound (4.3 g, 8.76 mmol, 37% yield, 95% purity) as a colourless oil which solidified upon standing. UPLC-MS (Method 1): m/z 464.1 (M−H)$^−$ at 1.76 min. $^1$H NMR (500 MHz, DMSO-$d_6$) δ 10.64 (br s, 1H), 8.23 (d, J=1.9 Hz, 1H), 8.13 (dd, J=8.0, 1.9 Hz, 1H), 7.84 (d, J=8.4 Hz, 1H), 7.65 (d, J=8.1 Hz, 1H), 7.53 (dd, J=8.4, 2.2 Hz, 1H), 7.44 (d, J=2.2 Hz, 1H), 3.84 (s, 3H), 3.05 (q, J=7.4 Hz, 2H), 1.20 (t, J=7.3 Hz, 3H).

Step 2: tert-butyl 2-(2-(2-ethyl-5-(methoxycarbonyl)phenylsulfonamido)-4-(trifluoromethyl)phenyl)pyrrole-1-carboxylate: A mixture of the product from Step 1 above (0.210 g, 0.428 mmol, 95% purity), (1-(tert-butoxycarbonyl)pyrrol-2-yl)boronic acid (0.124 g, 0.585 mmol), $K_3PO_4$(s) (0.287 g, 1.35 mmol) in dioxane (4 ml) and water (1 ml) was treated with XPhos Pd G3 (0.018 g, 0.023 mmol). The resultant mixture was degassed with $N_2$ for 10 min and then heated to 80° C. for 17 h. The reaction mixture was concentrated in vacuo and the residue dissolved in DCM (2 ml) and dried by passage through a phase separator. The filtrate was directly purified by chromatography on silica gel (24 g cartridge, 0-50% EtOAc/isohexane) to afford the title compound (0.200 g, 0.344 mmol, 80% yield, 95% purity) as a pale brown solid. UPLC-MS (Method 1): m/z 453.3 (M+H−Boc)$^+$, 551.2 (M−H)$^−$, at 1.99 min.

Step 3: tert-butyl 2-(2-(2-ethyl-5-(methoxycarbonyl)phenylsulfonamido)-4-(trifluoromethyl)phenyl)pyrrolidine-1-carboxylate: The product from Step 2 above (0.20 g, 0.344 mmol, 95% purity) was dissolved in MeOH (12 ml) and 10% Pd/C (Type 39) (8.78 mg, 4.13 μmol) was added. The reaction mixture was stirred at RT under $H_2$ (3 bar) for 20 h. The mixture was filtered through Celite®, washing with MeOH (20 ml) and concentrated in vacuo. The residue was purified by chromatography on silica gel (12 g cartridge, 0-50% EtOAc/isohexane) to afford the title compound (0.178 g, 0.313 mmol, 91% yield, 98% purity) as a white solid. UPLC-MS (Method 1): m/z 457.3 (M+H−Boc)$^+$ at 1.88 min.

Step 4: 2-(2-((2-ethyl-5-(methoxycarbonyl)phenyl)sulfonamido)-4-(trifluoromethyl)phenyl)pyrrolidin-1-ium 2,2,2-trifluoroacetate: The product from Step 3 above (0.178 g, 0.313 mmol, 98% purity) was dissolved in DCM (5 ml) and TFA (5 ml) was added. The mixture was stirred at RT overnight. The mixture was concentrated in vacuo and the residue purified by chromatography on silica gel (24 g cartridge, 0-50% EtOAc/isohexane) to afford the title compound (0.140 g, 0.243 mmol, 78% yield, 99% purity) as a white solid. UPLC-MS (Method 1): m/z 457.3 (M+H)$^+$, 455.5 (M−H)$^-$ at 0.99 min. $^1$H NMR (500 MHz, DMSO-d$_6$) δ 8.36 (s, 1H), 8.09 (dd, J=7.8, 1.9 Hz, 1H), 7.69 (d, J=7.6 Hz, 1H), 7.61 (d, J=8.0 Hz, 1H), 7.47 (s, 1H), 7.06 (s, 1H), 4.95-4.87 (br m, 1H), 3.88 (s, 3H), 3.50-3.34 (m, 2H), 3.02 (q, J=7.4 Hz, 2H), 2.40-2.29 (m, 1H), 2.23-2.13 (m, 1H), 2.12-1.99 (m, 2H), 1.21 (t, J=7.4 Hz, 3H). Two exchangeable protons not observed.

Step 5: 4-ethyl-3-(N-(2-(pyrrolidin-2-yl)-5-(trifluoromethyl)phenyl)sulfamoyl)benzoic acid: 1 M LiOH(aq) (0.260 ml, 0.260 mmol) was added to a solution of the product from Step 4 above (50 mg, 0.087 mmol, 99% purity) in THF (5 ml) and the resultant mixture was stirred at RT over the weekend. The mixture was acidified to pH 7 using 10% w/v citric acid(aq) and the resultant precipitate was collected by filtration, washing with water (10 ml), and dried in vacuo to afford the title compound (16.1 mg, 0.036 mmol, 41% yield, 98% purity) as a white solid. UPLC-MS (Method 1): m/z 443.3 (M+H)$^+$, 441.2 (M−H)$^-$ at 0.89 min. $^1$H NMR (500 MHz, DMSO-d$_6$) δ 13.0 (br s, 1H), 9.70 (br s, 1H), 8.52 (d, J=1.9 Hz, 1H), 7.91 (dd, J=7.9, 1.9 Hz, 1H), 7.42 (d, J=8.0 Hz, 1H), 7.33 (d, J=1.8 Hz, 1H), 7.23 (d, J=7.9 Hz, 1H), 6.83 (d, J=7.8 Hz, 1H), 4.58 (t, J=8.4 Hz, 1H), 3.33 (q, J=7.5 Hz, 2H), 3.19 (dq, J=14.8, 7.4 Hz, 1H), 3.08 (dq, J=14.9, 7.5 Hz, 1H), 2.27-2.14 (m, 1H), 2.14-1.90 (m, 3H), 1.18 (t, J=7.5 Hz, 3H). One exchangeable proton not observed.

Example 6: 4-ethyl-3-(N-(2-(1-methylpyrrolidin-2-yl)-5-(trifluoromethyl)phenyl)sulfamoyl)benzoic

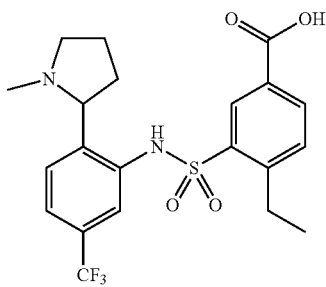 [SMILES: CCc1ccc(C(=O)O)cc1S(=O)(=O)Nc1cc(C(F)(F)F)ccc1C1CCCN1C]

Step 1: methyl 4-ethyl-3-(N-(2-(1-methylpyrrolidin-2-yl)-5-(trifluoromethyl)phenyl)sulfamoyl)benzoate: The product from Example 5 Step 4 (90 mg, 0.156 mmol, 99% purity) in DCM (4 ml) was treated with paraformaldehyde (14 mg, 0.473 mmol) and AcOH (27 µl, 0.473 mmol), followed by sodium triacetoxyhydroborate (100 mg, 0.473 mmol). The resultant mixture was stirred at RT for 16 h. The reaction mixture was diluted with DCM (20 ml) and washed with saturated NaHCO$_3$ (aq) (5 ml). The organic phase was dried over MgSO$_4$, filtered and concentrated in vacuo to afford the title compound (70 mg, 0.137 mmol, 88% yield, 92% purity) as a colourless oil. UPLC-MS (Method 1): m/z 471.3 (M+H)$^+$, 469.2 (M−H)$^-$, at 1.13 min.

Step 2: 4-ethyl-3-(N-(2-(1-methylpyrrolidin-2-yl)-5-(trifluoromethyl)phenyl)sulfamoyl)benzoic acid: 1 M LiOH(aq) (0.411 ml, 0.411 mmol) was added to a solution of the product from Step 1 above (70 mg, 0.137 mmol, 92% purity) in THF (5 ml) and the resultant mixture was stirred at RT for 2 h. The mixture was concentrated in vacuo. The residue was purified by chromatography (12 g reverse phase cartridge, 5-50% MeCN/Water 0.1% Formic Acid) to afford the title compound (31.7 mg, 0.067 mmol, 49% yield, 97% purity) as a white solid. UPLC-MS (Method 1): m/z 457.3 (M+H)$^+$, 455.2 (M−H)$^-$, at 0.97 min. $^1$H NMR (500 MHz, DMSO-d$_6$) δ 12.92 (br s, 2H), 8.49 (d, J=1.9 Hz, 1H), 7.99 (dd, J=7.9, 1.9 Hz, 1H), 7.51 (d, J=8.0 Hz, 1H), 7.36-7.26 (m, 2H), 7.05 (d, J=8.0 Hz, 1H), 4.10 (t, J=9.0 Hz, 1H), 3.63-3.55 (m, 1H), 3.19-3.01 (m, 2H), 2.93-2.83 (m, 1H), 2.49 (s, 3H), 2.31-2.20 (m, 1H), 2.11-1.93 (m, 2H), 1.89-1.79 (m, 1H), 1.22 (t, J=7.4 Hz, 3H).

Example 7: 4-ethyl-3-(N-(2-(pyrrolidin-3-yl)-5-(trifluoromethyl)phenyl)sulfamoyl)benzoic Acid

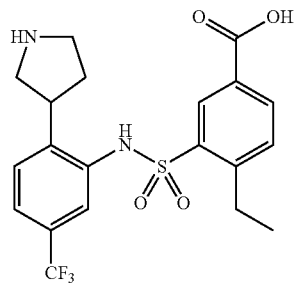 [SMILES: CCc1ccc(C(=O)O)cc1S(=O)(=O)Nc1cc(C(F)(F)F)ccc1C1CCNC1]

Step 1: tert-butyl 4-(2-nitro-4-(trifluoromethyl)phenyl)-2,3-dihydropyrrole-1-carboxylate: A mixture of 1-bromo-2-nitro-4-(trifluoromethyl)benzene (0.156 ml, 1.02 mmol), tert-butyl 4-(4,4,5,5-tetramethyl-1,3,2-dioxaborolan-2-yl)-2,3-dihydropyrrole-1-carboxylate (300 mg, 1.02 mmol), K$_3$PO$_4$(s) (647 mg, 3.05 mmol) in dioxane (4 ml) and water (1 ml) was degassed with N$_2$ for 10 min. XPhos Pd G3 (40 mg, 0.051 mmol) was added and the mixture was degassed with N$_2$ for 5 min, then heated at 80° C. for 2 h. The mixture was cooled, diluted with water (50 ml) and extracted with EtOAc (2×50 ml). The organic phases were combined and dried over MgSO$_4$, filtered and concentrated in vacuo. The residue was purified by chromatography on silica gel (40 g cartridge, 0-50% EtOAc/isohexane) to afford the title compound (0.230 g, 0.546 mmol, 54% yield, 85% purity) as a brown oil. UPLC-MS (Method 1): m/z 259 (M+H−Boc)$^+$ at 1.86 min.

Step 2: tert-butyl 3-(2-amino-4-(trifluoromethyl)phenyl)pyrrolidine-1-carboxylate: The product from Step 1 above (0.230 g, 0.546 mmol, 85% purity) was dissolved in MeOH (12 ml) and 10% Pd/C (Type 39) (14 mg, 6.55 µmol) was added and the reaction mixture was stirred at RT under H$_2$ (3 bar) for 20 h. The mixture was filtered through Celite®, washing with MeOH (20 ml) and the filtrate concentrated in vacuo. The residue was purified by chromatography on silica gel (12 g cartridge, 0-50% EtOAc/isohexane) to afford the title compound (0.148 g, 0.305 mmol, 56% yield, 68% purity) as a colourless oil. UPLC-MS (Method 1): m/z 231 (M+H−Boc)⁺ at 1.65 min.

Step 3: tert-butyl 3-(2-(2-ethyl-5-(methoxycarbonyl)phenylsulfonamido)-4-(trifluoromethyl)phenyl)pyrrolidine-1-carboxylate: A solution of the product from Step 2 above (0.148 g, 0.305 mmol, 68% purity) in DCM (10 ml) and pyridine (0.148 ml, 1.83 mmol) was added to a solution of the product from Example 3 Step 2 (0.080 g, 0.305 mmol) in DCM (10 ml) and the solution was stirred at RT for 48 h. The mixture was concentrated in vacuo and the residue was purified by chromatography on silica gel (40 g cartridge, 0-50% EtOAc/isohexane) to afford the title compound (0.135 g, 0.206 mmol, 68% yield, 85% purity) as a brown oil. UPLC-MS (Method 1): m/z 457.4 (M+H−Boc)⁺, 555.2 (M−H)⁻, at 1.85 min.

Step 4: 3-(2-((2-ethyl-5-(methoxycarbonyl)phenyl)sulfonamido)-4-(trifluoromethyl)phenyl)pyrrolidin-1-ium 2,2,2-trifluoroacetate: The product from Step 3 above (0.135 g, 0.206 mmol, 85% purity) was dissolved in DCM (5 ml) and treated with TFA (5 ml). The resultant mixture was stirred at RT overnight. The mixture was concentrated in vacuo to afford the title compound (0.120 g, 0.189 mmol, 92% yield, 90% purity) as a brown oil. UPLC-MS (Method 1): m/z 457.3 (M+H)⁺, 455.5 (M−H)⁻, at 1.01 min.

Step 5: 4-ethyl-3-(N-(2-(pyrrolidin-3-yl)-5-(trifluoromethyl)phenyl)sulfamoyl)benzoic acid: 1 M LiOH(aq) (0.710 ml, 0.710 mmol) was added to a solution of the product from Step 4 above (0.120 g, 0.189 mmol, 90% purity) in THF (5 ml) and the resultant mixture was stirred at RT for 2 h. The mixture was concentrated in vacuo and the residue was purified by chromatography (12 g reverse phase cartridge, 5-50% MeCN/Water 0.1% Formic Acid) (54.5 mg, 0.121 mmol, 64% yield, 98% purity) as a white solid. UPLC-MS (Method 1): m/z 443.3 (M+H)⁺, 441.2 (M−H)⁻, at 0.89 min. ¹H NMR (500 MHz, DMSO-d₆) δ 8.52 (d, J=1.9 Hz, 1H), 7.88 (dd, J=7.9, 1.9 Hz, 1H), 7.39 (d, J=7.9 Hz, 1H), 7.18-7.10 (m, 2H), 6.77-6.69 (m, 1H), 3.79-3.65 (m, 1H), 3.56-3.42 (m, 2H), 3.20-3.10 (m, 4H), 2.33-2.21 (m, 1H), 2.06-1.93 (m, 1H), 1.18 (t, J=7.5 Hz, 3H). Three exchangeable protons not observed.

Example 8: 4-ethyl-3-(N-(2-(piperidin-2-yl)-5-(trifluoromethyl)phenyl)sulfamoyl)benzoic Acid

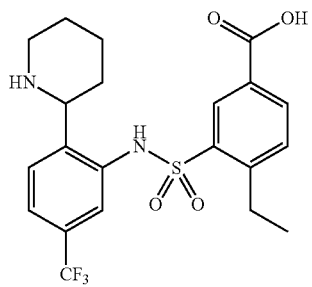 [SMILES: CCc1ccc(C(=O)O)cc1S(=O)(=O)Nc1cc(C(F)(F)F)ccc1C1CCCCN1]

Step 1: methyl 4-ethyl-3-(N-(2-(pyridin-2-yl)-5-(trifluoromethyl)phenyl)sulfamoyl)benzoate: 0.5 M pyridin-2-ylzinc(II) bromide in THF (5.15 ml, 2.57 mmol) was added to a solution of the product from Example 5 Step 1 (0.30 g, 0.643 mmol) in THF (5 ml) and the resultant mixture treated with Pd(PPh₃)₄ (74 mg, 0.064 mmol). The mixture was degassed with N₂ and then heated at 80° C. for 16 h. The mixture was cooled, diluted with water (50 ml), and extracted with EtOAc (2×50 ml). The organic phases were combined, dried over MgSO₄, filtered and concentrated in vacuo. The residue was purified by chromatography on silica gel (24 g cartridge, 0-80% EtOAc/isohexane) to afford the title compound (0.230 g, 0.461 mmol, 72% yield, 93% purity) as a yellow solid. UPLC-MS (Method 1): m/z 465.3 (M+H)⁺, 464.2 (M−H)⁻, at 1.88 min.

Step 2: methyl 4-ethyl-3-(N-(2-(piperidin-2-yl)-5-(trifluoromethyl)phenyl)sulfamoyl)benzoate: The product from Step 1 above (0.230 g, 0.461 mmol, 93% purity) was dissolved in AcOH (5 ml) and 5% Rh/C (0.05 g, 24.3 µmol) was added and the reaction mixture was stirred at RT under H₂ (5 bar) for 98 h, then at 45° C. for 24 h. The mixture was filtered through Celite®, washing with MeOH (20 ml), and the filtrate was concentrated in vacuo. The residue was purified by chromatography on silica gel (24 g cartridge, 0-10% MeOH/DCM) to afford the title compound (0.120 g, 0.245 mmol, 53% yield, 96% purity) as a white solid. UPLC-MS (Method 1): m/z 471.3 (M+H)⁺ at 1.02 min.

Step 3: 4-ethyl-3-(N-(2-(piperidin-2-yl)-5-(trifluoromethyl)phenyl)sulfamoyl)benzoic acid: 1 M LiOH(aq) (0.383 ml, 0.383 mmol) was added to a solution of the product from Step 2 above (60 mg, 0.123 mmol, 96% purity) in THF (5 ml) and the resultant mixture was stirred at RT over the weekend. The mixture was acidified to pH 7 with 10% w/v citric acid(aq) and the resultant precipitate was collected by filtration, washing with water (10 ml), and dried in vacuo to afford the title compound (16.3 mg, 0.035 mmol, 28% yield, 97% purity) as a white solid. UPLC-MS (Method 1): m/z 457.3 (M+H)⁺, 455.2 (M−H)⁻, at 0.92 min. ¹H NMR (500 MHz, DMSO-d₆) δ 8.51 (d, J=1.9 Hz, 1H), 7.90 (dd, J=7.9, 1.9 Hz, 1H), 7.47-7.38 (m, 2H), 7.23 (d, J=7.9 Hz, 1H), 6.87 (dd, J=8.0, 1.9 Hz, 1H), 4.30-4.27 (m, 1H), 3.45-3.37 (m, 1H), 3.17 (q, J=7.4 Hz, 2H), 3.02-2.92 (m, 1H), 2.01-1.77 (m, 4H), 1.66-1.51 (m, 2H), 1.20 (t, J=7.5 Hz, 3H). Three exchangeable protons not observed.

Example 9: 3-(N-(2-cyclohexyl-5-(trifluoromethyl)phenyl)sulfamoyl)-4-ethylbenzoic Acid

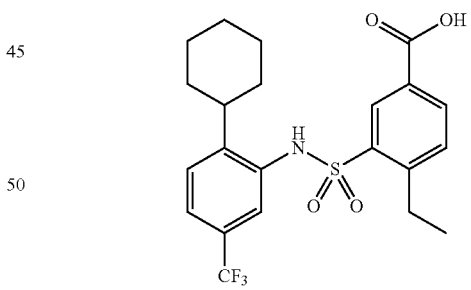

Step 1: methyl 4-ethyl-3-(N-(4-(trifluoromethyl)-2',3',4',5'-tetrahydro-[1,1'-biphenyl]-2-yl)sulfamoyl)benzoate: A mixture of the product from Example 5 Step 1 (150 mg, 0.322 mmol), 2-(cyclohex-1-en-1-yl)-4,4,5,5-tetramethyl-1,3,2-dioxaborolane (0.14 ml, 0.651 mmol), 1 M K₃PO₄ (aq) (0.540 ml, 0.540 mmol) and dioxane (3.2 ml) was treated with XPhos Pd G3 (14.5 mg, 0.017 mmol). The resultant mixture was degassed with N₂ for 15 min and then heated at 80° C. for 3.75 h. The mixture was allowed to cool to RT and then concentrated in vacuo onto Celite® and purified by chromatography on silica gel (12 g cartridge, 0-10% EtOAc/isohexane) to afford the title compound (125 mg, 0.258 mmol, 80% yield, 96% purity) as a yellow solid. UPLC-MS (Method 1): m/z 466.3 (M−H)⁻ at 2.02 min.

Step 2: methyl 3-(N-(2-cyclohexyl-5-(trifluoromethyl)phenyl)sulfamoyl)-4-ethylbenzoate: 5% Pd/C (Type 87L) (137 mg, 0.026 mmol) was added to a solution of the product from Step 1 above (125 mg, 0.258 mmol, 96% purity) in EtOH (5.5 ml). The resultant suspension was stirred at RT under H₂ (3 bar) at RT for 17 h. The reaction mixture was filtered through Celite®, and washing with MeOH (15 ml), and then dried over MgSO₄, filtered, and concentrated in vacuo to afford the title compound (134 mg) as a pale yellow oil. UPLC-MS (Method 1): m/z 468.2 (M−H)⁻ at 1.98 min.

Step 3: 3-(N-(2-cyclohexyl-5-(trifluoromethyl)phenyl)sulfamoyl)-4-ethylbenzoic acid: 1 M LiOH(aq) (1.03 ml, 1.03 mmol) was added to a solution of the product from Step 2 above (134 mg) in THF (2 ml). The resultant mixture was stirred at RT for 5 days. The reaction mixture was concentrated in vacuo, and the residue dissolved in water (5 ml) and then washed with EtOAc (5 ml). The aqueous phase was acidified using 1 M HCl(aq) until pH 4-5 and then extracted with EtOAc (3×5 ml). The extracts were combined and dried over MgSO₄, filtered, and concentrated in vacuo to afford the title compound (94.6 mg, 0.199 mmol, 78% yield, 96% purity) as an off-white solid. UPLC-MS (Method 1): m/z 454.2 (M−H)⁻ at 1.84 min. ¹H NMR (500 MHz, DMSO-d₆) δ 13.26 (br s, 1H), 10.25 (br s, 1H), 8.19 (d, J=1.8 Hz, 1H), 8.07 (dd, J=8.0, 1.9 Hz, 1H), 7.61 (d, J=8.0 Hz, 1H), 7.53 (d, J=8.0 Hz, 1H), 7.44 (d, J=8.2 Hz, 1H), 7.31 (d, J=2.0 Hz, 1H), 3.00 (q, J=7.4 Hz, 2H), 2.68-2.59 (m, 1H), 1.67-1.57 (m, 3H), 1.25-1.03 (m, 10H).

Example 10: 4-ethyl-3-(N-(2-(1-methylpiperidin-2-yl)-5-(trifluoromethyl)phenyl)sulfamoyl)benzoic Acid

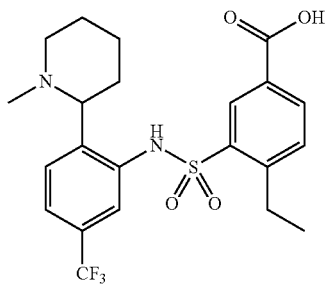 [SMILES: CCc1ccc(C(=O)O)cc1S(=O)(=O)Nc1cc(C(F)(F)F)ccc1C1CCCCN1C]

Step 1: methyl 4-ethyl-3-(N-(2-(1-methylpiperidin-2-yl)-5-(trifluoromethyl)phenyl)sulfamoyl)benzoate: The product from Example 8 Step 2 (60 mg, 0.123 mmol, 96% purity) in DCM (4 ml) was treated with paraformaldehyde (11 mg, 0.383 mmol) and AcOH (22 µl, 0.383 mmol), followed by NaBH(OAc)₃(s) (81 mg, 0.383 mmol). The resultant mixture was stirred at RT for 16 h. The mixture was diluted with DCM (20 ml) and washed with saturated NaHCO₃ (aq) (5 ml). The organic phase was dried over MgSO₄, filtered and concentrated in vacuo. The residue was purified by chromatography on silica gel (24 g cartridge, 0-10% MeOH/DCM) to afford the title compound (50 mg, 0.074 mmol, 60% yield, 72% purity) as a colourless oil. UPLC-MS (Method 1): m/z 485.4 (M+H)⁺, 483.3 (M−H)⁻, at 1.12 min.

Step 2: 4-ethyl-3-(N-(2-(1-methylpiperidin-2-yl)-5-(trifluoromethyl)phenyl)sulfamoyl)benzoic acid: 1 M LiOH(aq) (0.223 ml, 0.223 mmol) was added to a solution of the product from Step 1 above (50 mg, 0.074 mmol) in THF (5 ml) and the resultant mixture was stirred at RT over the weekend. The mixture was then acidified to pH 7 using 10% w/v citric acid(aq) and concentrated in vacuo. The residue was purified by chromatography (12 g reverse phase cartridge, 10-45% MeCN/Water 0.1% Formic Acid) to afford the title compound (6.4 mg, 0.013 mmol, 18% yield, 98% purity) as a white solid. UPLC-MS (Method 1): m/z 471.3 (M+H)⁺, 469.2 (M−H)⁻, at 0.97 min. ¹H NMR (500 MHz, DMSO-d₆) δ 8.51-8.43 (m, 1H), 7.97 (d, J=7.9 Hz, 1H), 7.48 (d, J=8.0 Hz, 1H), 7.37 (d, J=1.9 Hz, 1H), 7.30 (d, J=7.9 Hz, 1H), 7.04 (s, 1H), 3.87-3.77 (br m, 1H), 3.40-3.25 (m, 1H), 3.22-3.05 (m, 3H), 2.25 (br s, 3H), 1.85-1.52 (m, 5H), 1.42 (m, 1H), 1.22 (t, J=7.5 Hz, 3H). Two exchangeable protons not observed.

Example 11: 3-(N-(2-cyclohexyl-5-(methylsulfonyl)phenyl)sulfamoyl)-4-ethylbenzoic Acid

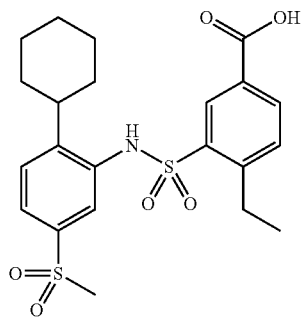 [SMILES: CCc1ccc(C(=O)O)cc1S(=O)(=O)Nc1cc(S(C)(=O)=O)ccc1C1CCCCC1]

Step 1: methyl 3-(N-(2-bromo-5-(methylsulfonyl)phenyl)sulfamoyl)-4-ethylbenzoate: 2-bromo-5-(methylsulfonyl)aniline (600 mg, 2.40 mmol) was added to a solution of the product from Example 3 Step 2 (756 mg, 2.88 mmol) and pyridine (0.78 ml, 9.64 mmol) in DCM (1.6 ml). The resultant mixture was stirred at RT for 4 days. The reaction mixture was concentrated in vacuo and azeotroped with toluene (50 ml). The residue was concentrated in vacuo onto Celite® in MeCN (50 ml) and purified by chromatography (40 g reverse phase C18 cartridge, 10-65% MeCN/0.1% formic acid(aq)) to afford the title compound (626 mg, 1.29 mmol, 54% yield, 98% purity) as an off-white solid. UPLC-MS (Method 1): m/z 476.2 (M+H)⁺, 474.0 (M−H)⁻, at 1.39 min.

Step 2: methyl 4-ethyl-3-(N-(4-(methylsulfonyl)-2',3',4',5'-tetrahydro-[1,1'-biphenyl]-2-yl)sulfamoyl)benzoate: A mixture of the product from Step 1 above (110 mg, 0.226 mmol, 98% purity), 2-(cyclohex-1-en-1-yl)-4,4,5,5-tetramethyl-1,3,2-dioxaborolane (100 µl, 0.465 mmol), 1 M K₃PO₄ (aq) (0.390 ml, 0.390 mmol) and dioxane (2.3 ml) was treated with XPhos Pd G3 (9.8 mg, 0.012 mmol). The resultant mixture was degassed with N₂ for 15 min and then heated at 80° C. for 19 h. The mixture was allowed to cool to RT and was then concentrated in vacuo onto Celite® and purified by chromatography on silica gel (12 g cartridge, 0-40% EtOAc/isohexane) to afford the title compound (94 mg, 0.193 mmol, 85% yield, 98% purity) as an off-white solid. UPLC-MS (Method 1): m/z 478.4 (M+H)⁺, 476.2 (M−H)⁻, at 1.66 min.

Step 3: methyl 3-(N-(2-cyclohexyl-5-(methylsulfonyl)phenyl)sulfamoyl)-4-ethylbenzoate: 5% Pd/C (Type 87L) (21.0 mg, 3.94 µmol) was added to a solution of the product from Step 2 above (94 mg, 0.193 mmol, 98% purity) in EtOH (4 ml). The resultant suspension was stirred at RT under $H_2$ (1 bar) for 17 h. The reaction mixture was filtered through Celite®, washing with MeOH (15 ml). The filtrate was dried by passage through a phase separator and then concentrated in vacuo to afford the title compound (82.7 mg, 0.169 mmol, 88% yield, 98% purity) as a colourless oil. UPLC-MS (Method 1): m/z 480.3 (M+H)$^+$, 478.2 (M−H)$^−$, at 1.64 min.

Step 4: 3-(N-(2-cyclohexyl-5-(methylsulfonyl)phenyl)sulfamoyl)-4-ethylbenzoic acid: 1 M LiOH(aq) (0.700 ml, 0.700 mmol) was added to a solution of the product from Step 3 above (82.7 mg, 0.169 mmol, 98% purity) in THF (2.2 ml). The resultant mixture was stirred at RT for 18 h, then concentrated in vacuo. The residue was dissolved in water (4 ml) and washed with EtOAc (4 ml). The aqueous phase was acidified using 1 M HCl(aq) until pH 4-5 and then extracted with EtOAc (3×4 ml). The extracts were combined and dried by passage through a phase separator, then concentrated in vacuo to afford the title compound (63 mg, 0.134 mmol, 79% yield, 99% purity) as a cream solid. UPLC-MS (Method 1): m/z 466.3 (M+H)$^+$, 464.3 (M−H)$^−$, at 1.49 min. $^1$H NMR (500 MHz, DMSO-$d_6$) δ 13.27 (br s, 1H), 10.30 (br s, 1H), 8.20 (d, J=1.8 Hz, 1H), 8.06 (dd, J=8.0, 1.8 Hz, 1H), 7.71 (br d, J=8.1 Hz, 1H), 7.60 (d, J=8.1 Hz, 1H), 7.57 (d, J=2.0 Hz, 1H), 7.49 (d, J=8.2 Hz, 1H), 3.11 (s, 3H), 3.00 (q, J=7.4 Hz, 2H), 2.70-2.59 (m, 1H), 1.66-1.57 (m, 3H), 1.25-1.02 (m, 10H).

Example 12: 4-cyclopropyl-3-(N-(2-(piperidin-3-yl)-5-(trifluoromethyl)phenyl)sulfamoyl)benzoic Acid

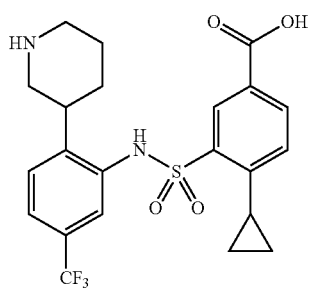 [SMILES: O=C(O)c1ccc(C2CC2)c(S(=O)(=O)Nc2cc(C(F)(F)F)ccc2C2CCCNC2)c1]

Step 1: methyl 4-bromo-3-(chlorosulfonyl)benzoate: A mixture of 4-bromo-3-(chlorosulfonyl)benzoic acid (15 g, 50.1 mmol) and thionyl chloride (100 ml) was heated under reflux for 4 h. Upon cooling to RT, the mixture was concentrated in vacuo and the residue added slowly to MeOH (300 ml) at 0° C. The resultant mixture was concentrated in vacuo and the residue was triturated with a small amount of MeOH to afford the title compound (9.87 g, 31.2 mmol, 62% yield, 99% purity) as a white solid. $^1$H NMR (500 MHz, DMSO-$d_6$) δ 8.47 (d, J=2.0 Hz, 1H), 7.78-7.70 (m, 2H), 3.86 (s, 3H).

Step 2: tert-butyl 3-(2-(2-bromo-5-(methoxycarbonyl)phenylsulfonamido)-4-(trifluoromethyl)phenyl)piperidine-1-carboxylate: A mixture of the product from Example 2 Step 2 (137 mg, 0.354 mmol, 89% purity), the product from Step 1 above (141 mg, 0.444 mmol, 99% purity) and pyridine (90 μl, 1.11 mmol) in DCM (2 ml) was stirred at 35° C. for 4 days. The mixture was concentrated in vacuo onto silica and purified by chromatography on silica gel (12 g cartridge, 0-50% EtOAc/isohexane) to afford the title compound (136 mg, 0.208 mmol, 59% yield, 95% purity) as a white solid. UPLC-MS (Method 1): m/z 643.2 (M+Na)$^+$, 619.1 (M−H)$^−$, at 1.87 min.

Step 3: tert-butyl 3-(2-(2-cyclopropyl-5-(methoxycarbonyl)phenylsulfonamido)-4-(trifluoromethyl)phenyl)piperidine-1-carboxylate: A degassed mixture of the product from Step 2 above (136 mg, 0.208 mmol, 95% purity) and Pd-174 (15 mg, 0.021 mmol) in THF (4 ml) was treated with 0.5 M cyclopropylzinc(II) bromide in THF (1.7 ml, 0.850 mmol) and the resultant mixture was stirred at RT overnight. The mixture was heated at 60° C. for 6 h. Upon cooling to RT, the mixture was concentrated in vacuo onto silica and purified by chromatography on silica gel (12 g cartridge, 0-50% EtOAc/isohexane) to afford the title compound (76 mg, 0.110 mmol, 53% yield, 84% purity) as a white solid. UPLC-MS (Method 1): m/z 605.3 (M+Na)$^+$, 581.2 (M−H)$^−$, at 1.92 min.

Step 4: 4-cyclopropyl-3-(N-(2-(piperidin-3-yl)-5-(trifluoromethyl)phenyl)sulfamoyl)benzoic acid: A mixture of the product from Step 3 above (76 mg, 0.110 mmol, 84% purity) and conc. HCl(aq) (1 ml, 12.2 mmol) in dioxane (4 ml) and water (1 ml) was heated at 90° C. overnight. The mixture was diluted with water (10 ml) and extracted with EtOAc (3×15 ml). The combined organic phases were washed with brine (10 ml), dried by passage through a phase separator and concentrated in vacuo. The crude product was purified by preparative HPLC (Waters, Acidic (0.1% Formic acid), Acidic, Waters X-Select Prep-C18, 5 μm, 19×50 mm column, 10-40% MeCN in Water) to afford the title compound (38.2 mg, 0.081 mmol, 74% yield, 99% purity) as a white solid. UPLC-MS (Method 1): m/z 469.3 (M+H)$^+$, 467.1 (M−H)$^−$ at 0.93 min. $^1$H NMR (500 MHz, DMSO-$d_6$) δ 8.72 (br s, 1H), 8.50 (d, J=1.9 Hz, 1H), 7.75 (dd, J=8.2, 2.0 Hz, 1H), 7.40 (d, J=1.9 Hz, 1H), 7.10 (d, J=7.9 Hz, 1H), 6.80 (d, J=8.2 Hz, 1H), 6.73 (d, J=7.9 Hz, 1H), 3.75-3.67 (m, 1H), 3.36 (s, 1H), 3.30-3.27 (m, 1H), 3.27-3.21 (m, 1H), 2.92-2.83 (m, 1H), 2.79 (t, J=11.9 Hz, 1H), 1.94-1.87 (m, 1H), 1.79-1.63 (m, 3H), 1.04-0.94 (m, 2H), 0.79-0.66 (m, 2H). Two exchangeable protons not observed.

Example 13: 3-(N-(5-cyano-2-cyclohexylphenyl)sulfamoyl)-4-ethylbenzoic Acid

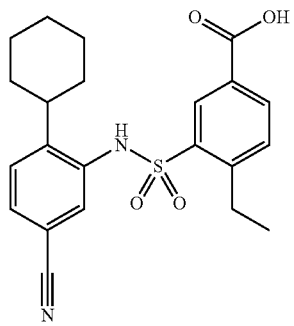

Step 1: methyl 3-(N-(2-bromo-5-cyanophenyl)sulfamoyl)-4-ethylbenzoate: A solution of 3-amino-4-bromobenzonitrile (0.7 g, 3.55 mmol), the product from Example 3 Step 2 (1.03 g, 3.91 mmol) and pyridine (0.862 ml, 10.7 mmol) in DCM (6 ml) was stirred at RT for 135 h. The reaction mixture was concentrated in vacuo and the residue was partially purified by chromatography on silica gel (40 g cartridge, 0-100% EtOAc/isohexane), then purified by chromatography (40 g reverse phase C18 cartridge, 45-75% MeCN/0.1% formic acid(aq)) to afford the title compound (570 mg, 1.34 mmol, 38% yield) as a white solid. UPLC-MS (Method 1): m/z 421.2 (M–H)⁻ at 1.52 min. ¹H NMR (500 MHz, DMSO-$d_6$) δ 10.65 (br s, 1H), 8.21 (d, J=1.9 Hz, 1H), 8.12 (dd, J=8.0, 1.9 Hz, 1H), 7.82 (d, J=8.2 Hz, 1H), 7.68-7.61 (m, 3H), 3.84 (s, 3H), 3.03 (q, J=7.4 Hz, 2H), 1.21 (t, J=7.4 Hz, 3H).

Step 2: methyl 3-(N-(4-cyano-2',3',4',5'-tetrahydro-[1,1'-biphenyl]-2-yl)sulfamoyl)-4-ethylbenzoate: A mixture of the product from Step 1 above (89 mg, 0.210 mmol), 2-(cyclohex-1-en-1-yl)-4,4,5,5-tetramethyl-1,3,2-dioxaborolane (90 μl, 0.421 mmol), 1 M $K_3PO_4$ (aq) (0.350 ml, 0.350 mmol) and dioxane (3.2 ml) was treated with XPhos Pd G3 (8.9 mg, 10.5 μmol). The resultant mixture was degassed with $N_2$ for 15 min and then heated at 80° C. for 17 h. The mixture was allowed to cool to RT, and was then concentrated in vacuo onto Celite® and purified by chromatography on silica gel (12 g cartridge, 0-20% EtOAc/isohexane) to afford the title compound (57.7 mg, 0.135 mmol, 64% yield, 99% purity) as a colourless oil. UPLC-MS (Method 1): m/z 423.3 (M–H)⁻ at 1.82 min.

Step 3: methyl 3-(N-(5-cyano-2-cyclohexylphenyl)sulfamoyl)-4-ethylbenzoate: 5% Pd/C (Type 87L) (19 mg, 3.57 μmol) was added to a solution of the product from Step 2 above (54 mg, 0.127 mmol) in EtOH (5 ml). The resultant suspension was stirred at RT under $H_2$ (1 bar) for 18 h. The reaction mixture was filtered through Celite®, washing with MeOH (15 ml). The filtrate was dried by passage through a phase separator and then concentrated in vacuo. The crude product was purified by chromatography on silica gel (12 g cartridge, 0-25% EtOAc/isohexane) to afford a 95:5 mixture of the title compound and starting material. This material was combined with 5% Pd/C (Type 87L) (10 mg, 1.88 μmol) in EtOH (2 ml) and stirred at RT under $H_2$ (1 bar) for 5.5 h. The reaction mixture was filtered through Celite®, washing with MeOH (10 ml). The filtrate was concentrated onto Celite® and then purified by chromatography on silica gel (4 g cartridge, 0-25% EtOAc/isohexane) to afford the title compound (36 mg, 0.084 mmol, 66% yield, 99% purity) as an off-white solid. UPLC-MS (Method 1): m/z 425.4 (M–H)⁻ at 1.78 min.

Step 4: 3-(N-(5-cyano-2-cyclohexylphenyl)sulfamoyl)-4-ethylbenzoic acid: 1 M LiOH(aq) (0.340 ml, 0.340 mmol) was added to a solution of the product from Step 1 above (36 mg, 0.084 mmol) in THF (0.68 ml). The resultant mixture was stirred at RT for 40 h. The mixture was concentrated in vacuo and the residue dissolved in water (4 ml) and then washed with EtOAc (4 ml). The aqueous phase was acidified using 1 M HCl(aq) until pH 4-5 and then extracted with EtOAc (3×4 ml). The extracts were combined and dried over $MgSO_4$, filtered, and then concentrated in vacuo to afford the title compound (28.0 mg, 0.066 mmol, 78% yield, 97% purity) as an off-white solid. UPLC-MS (Method 1): m/z 411.3 (M–H)⁻ at 1.64 min. ¹H NMR (500 MHz, DMSO-$d_6$) δ 13.27 (br s, 1H), 10.32 (br s, 1H), 8.17 (d, J=1.8 Hz, 1H), 8.06 (dd, J=8.0, 1.8 Hz, 1H), 7.64 (d, J=8.5 Hz, 1H), 7.61 (d, J=8.0 Hz, 1H), 7.50 (d, J=1.8 Hz, 1H), 7.40 (d, J=8.1 Hz, 1H), 3.01 (q, J=7.4 Hz, 2H), 1.64-1.51 (m, 3H), 1.25-0.96 (m, 11H).

Example 14: 4-ethyl-3-(N-(5-(methylsulfonyl)-2-(piperidin-3-yl)phenyl)sulfamoyl)benzoic Acid

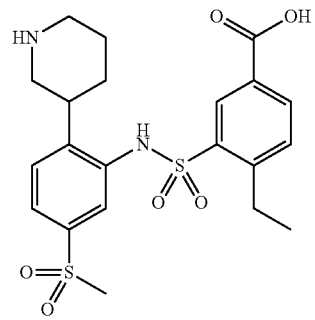 [SMILES: CCc1ccc(C(=O)O)cc1S(=O)(=O)Nc1cc(S(C)(=O)=O)ccc1C1CCCNC1]

Step 1: tert-butyl 5-(2-(2-ethyl-5-(methoxycarbonyl)phenylsulfonamido)-4-(methylsulfonyl)phenyl)-3,4-dihydropyridine-1(2H)-carboxylate: A mixture of the product from Example 11 Step 1 (150 mg, 0.315 mmol), tert-butyl 5-(4,4,5,5-tetramethyl-1,3,2-dioxaborolan-2-yl)-3,4-dihydropyridine-1(2H)-carboxylate (117 mg, 0.378 mmol), $K_3PO_4$(s) (87 mg, 0.409 mmol) in dioxane (2.5 ml) and water (0.5 ml) was treated with XPhos Pd G3 (13.3 mg, 0.016 mmol). The resultant mixture was degassed with $N_2$ for 15 min and then heated at 80° C. overnight. The reaction mixture was cooled, diluted with water (75 ml) and extracted with DCM (2×75 ml). The combined organic phases were dried by passage through a phase separator and concentrated in vacuo. The residue was purified by chromatography on silica gel (12 g cartridge, 0-100% EtOAc/isohexane) to afford the title compound (33 mg, 0.055 mmol, 18% yield, 97% purity) as a yellow oil. The aqueous phase was further extracted with DCM (2×75 ml) to afford a second batch the title compound (98 mg, 0.163 mmol, 52% yield, 96% purity) as a yellow oil. UPLC-MS (Method 2): m/z 479.3 (M+H–Boc)⁺ at 1.39 min.

Step 2: methyl 4-ethyl-3-(N-(5-(methylsulfonyl)-2-(piperidin-3-yl)phenyl)sulfamoyl)benzoate: A solution of the product from Step 1 above (131 mg, 0.220 mmol, 97% purity) in DCM (3 ml) was treated with TFA (174 μl, 2.26 mmol). The reaction mixture was stirred at RT for 30 min, then concentrated in vacuo. The residue was dissolved in MeOH (3 ml) and treated with 5% Pd/C (Type 87L) (72.8 mg, 0.014 mmol) and stirred at RT under $H_2$ (3 bar) for a total of 9 h. Additional 5% Pd/C (Type 87L) (36.4 mg, 0.07 mmol) was added and the solution was stirred at RT under $H_2$ (5 bar) overnight. The reaction mixture was concentrated in vacuo and the residue dissolved in EtOAc (50 ml) and washed with saturated $NaHCO_3$ (aq) (2×50 ml). The organic phase was dried by passage through a phase separator and concentrated in vacuo. The crude product was purified by chromatography on silica gel (12 g cartridge, 0-10% MeOH/DCM) to afford the title compound (40 mg, 0.082 mmol, 37% yield, 98% purity) as a white solid. UPLC-MS (Method 2): m/z 481.4 (M+H)⁺ at 0.92 min.

Step 3: 4-ethyl-3-(N-(5-(methylsulfonyl)-2-(piperidin-3-yl)phenyl)sulfamoyl)benzoic acid: The product from Step 2 above (40 mg, 0.082 mmol, 98% purity) was treated with 4 M HCl in dioxane (25.3 μl, 0.832 mmol) and water (0.5 ml). The resultant solution was heated at 60° C. for 6 h. conc. HCl(aq) (1 ml) and water (1 ml) was added and heating was continued for 3 days. The reaction mixture was concentrated in vacuo and purified by preparative HPLC (Waters, Acidic (0.1% Formic acid), Acidic, Waters X-Select Prep-C18, 5 μm, 19×50 mm column, 2-20% MeCN in Water) to afford the title compound (7 mg, 0.014 mmol, 17% yield, 95% purity) as a white solid. UPLC-MS (Method 1): m/z 467.3 (M+H)+, 465.2 (M−H)−, at 0.71 min. 1H NMR (500 MHz, DMSO-d6) δ 8.54 (s, 1H), 7.85 (dd, J=8.0, 1.8 Hz, 1H), 7.61 (d, J=1.9 Hz, 1H), 7.34 (d, J=7.9 Hz, 1H), 7.18 (d, J=8.0 Hz, 1H), 7.01 (dd, J=8.0, 2.0 Hz, 1H), 3.75-3.63 (m, 1H), 3.34-3.27 (m, 1H), 3.27-3.16 (m, 3H), 2.94-2.83 (m, 5H), 1.94-1.86 (m, 1H), 1.84-1.65 (m, 3H), 1.20 (t, J=7.5 Hz, 3H). Three exchangeable protons not observed.

Example 15: 4-ethyl-3-(N-(5-(methylsulfonyl)-2-(piperidin-2-yl)phenyl)sulfamoyl)benzoic Acid

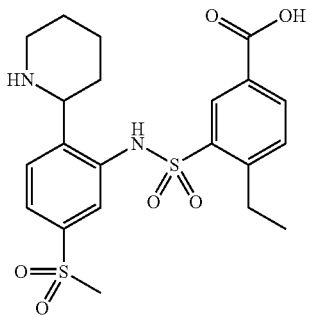 [SMILES: CCc1ccc(C(=O)O)cc1S(=O)(=O)Nc1cc(S(C)(=O)=O)ccc1C1CCCCN1]

Step 1: 5-(methylsulfonyl)-2-(pyridin-2-yl)aniline: 0.5 M pyridin-2-ylzinc(II) bromide in THF (14.4 ml, 7.20 mmol) was added to a solution of 2-bromo-5-(methylsulfonyl) aniline (0.60 g, 2.40 mmol) in dioxane (5 ml). The resultant mixture was treated with Pd(PPh3)4 (0.277 g, 0.240 mmol), degassed with N2, and then heated at 80° C. for 16 h. The mixture was cooled, concentrated in vacuo onto silica and partially purified by chromatography on silica gel (40 g cartridge, 0-100% EtOAc/isohexane). The partially purified material was triturated with TBME to afford the title compound (1.06 g, 2.35 mmol, 98% yield, 55% purity) as a yellow solid. UPLC-MS (Method 1): m/z 249.2 (M+H)+ at 0.72 min.

Step 2: methyl 4-ethyl-3-(N-(5-(methylsulfonyl)-2-(pyridin-2-yl)phenyl)sulfamoyl)benzoate: A solution of the product from Step 1 above (0.20 g, 0.443 mmol, 55% purity) in DCM (3 ml) and pyridine (0.215 ml, 2.66 mmol) was treated with the product from Example 3 Step 2 (0.116 g, 0.443 mmol). The resultant solution was stirred at RT for 48 h. The mixture was concentrated in vacuo and purified by chromatography on silica gel (24 g cartridge, 0-10% MeOH/DCM) to afford the title compound (87 mg, 0.161 mmol, 36% yield, 88% purity) as a yellow solid. UPLC-MS (Method 1): m/z 475.3 (M+H)+, 473.3 (M−H)−, at 1.50 min.

Step 3: 4-ethyl-3-(N-(5-(methylsulfonyl)-2-(pyridin-2-yl) phenyl)sulfamoyl)benzoic acid: 4 M HCl(aq) (0.202 ml, 0.807 mmol) was added to a solution of the product from Step 2 above (87 mg, 0.161 mmol, 88% purity) in dioxane (5 ml) and the resultant solution was heated at 60° C. for 24 h. The mixture was concentrated in vacuo and the residue titrated with TBME (10 ml), followed by MeOH (5 ml) to afford the title compound (70 mg, 0.149 mmol, 92% yield, 98% purity) as a yellow solid. UPLC-MS (Method 1): m/z 461.3 (M+H)+, 459.2 (M−H)−, at 1.34 min. 1H NMR (500 MHz, DMSO-d6) δ 13.31 (br s, 1H), 13.12 (br s, 1H), 8.83-8.70 (m, 1H), 8.28 (d, J=1.8 Hz, 1H), 8.13 (d, J=8.3 Hz, 1H), 8.07-7.89 (m, 4H), 7.82-7.67 (m, 1H), 7.61-7.50 (m, 1H), 7.44 (d, J=8.0 Hz, 1H), 3.18 (s, 3H), 2.75 (q, J=7.4 Hz, 2H), 0.98 (t, J=7.4 Hz, 3H).

Step 4: 4-ethyl-3-(N-(5-(methylsulfonyl)-2-(piperidin-2-yl)phenyl)sulfamoyl)benzoic acid: The product from Step 3 above (0.070 g, 0.149 mmol, 98% purity) was dissolved in AcOH (5 ml) and treated with 5% Rh/C (0.05 g, 24.3 μmol) was added and the reaction mixture was stirred at 50° C. under H2 (5 bar) for 24 h. The mixture was filtered through Celite®, washing with MeOH (20 ml), and concentrated in vacuo. The residue was purified by preparative HPLC (Waters, Acidic (0.1% Formic acid), Acidic, Waters X-Select Prep-C18, 5 μm, 19×50 mm column, 5-20% MeCN in Water) to afford the title compound (11.1 mg, 0.024 mmol, 16% yield, 99% purity) as a white solid. UPLC-MS (Method 1): m/z 467.3 (M+H)+, 465.2 (M−H)−, at 0.76 min. 1H NMR (500 MHz, DMSO-d6) δ 8.50 (d, J=1.9 Hz, 1H), 7.88 (dd, J=7.9, 1.9 Hz, 1H), 7.72 (d, J=1.9 Hz, 1H), 7.41 (d, J=7.9 Hz, 1H), 7.29 (d, J=8.0 Hz, 1H), 7.07 (dd, J=7.9, 2.0 Hz, 1H), 4.33 (dd, J=11.3, 3.5 Hz, 1H), 3.41 (d, J=12.3 Hz, 1H), 3.18 (q, J=7.3 Hz, 2H), 3.01-2.95 (m, 1H), 2.93 (s, 3H), 1.96-1.79 (m, 4H), 1.65-1.52 (m, 2H), 1.21 (t, J=7.5 Hz, 3H). Three exchangeable protons not observed.

Example 16: 4-cyclopropyl-3-(N-(2-(piperidin-2-yl)-5-(trifluoromethyl)phenyl)sulfamoyl)benzoic Acid

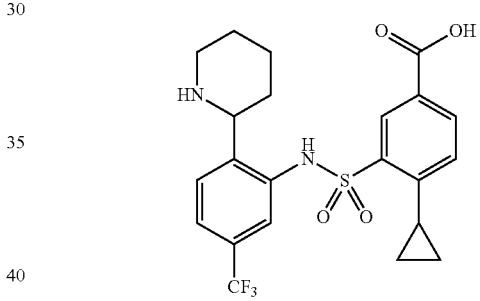

Step 1: 2-(pyridin-2-yl)-5-(trifluoromethyl)aniline: 0.5 M pyridin-2-ylzinc(II) bromide in THF (15.0 ml, 7.50 mmol) was added to a solution of 2-bromo-5-(trifluoromethyl) aniline (0.60 g, 2.50 mmol) in dioxane (5 ml). The resultant mixture was treated with Pd(PPh3)4 (0.289 g, 0.250 mmol), then degassed with N2 and heated at 80° C. for 16 h. The mixture was cooled and concentrated in vacuo onto silica and purified by chromatography on silica gel (40 g cartridge, 0-100% EtOAc/isohexane) to afford the title compound (0.364 g, 1.36 mmol, 54% yield, 89% purity) as a red solid. UPLC-MS (Method 1): m/z 239.2 (M+H)+ at 1.33 min.

Step 2: methyl 4-bromo-3-(N-(2-(pyridin-2-yl)-5-(trifluoromethyl)phenyl)sulfamoyl)benzoate: A solution of the product from Step 1 above (0.180 g, 0.673 mmol) in DCM (3 ml) and pyridine (0.326 ml, 4.04 mmol) was treated with the product from Example 12 Step 1 (0.211 g, 0.673 mmol) and the resultant solution was stirred at RT for 48 h. The mixture was concentrated in vacuo and the residue purified by chromatography on silica gel (24 g cartridge, 0-10% MeOH/DCM) to afford the title compound (0.152 g, 0.295 mmol, 44% yield) as a yellow solid. UPLC-MS (Method 1): m/z 515.2 (M+H)+, 513.0 (M−H)−, at 1.82 min.

Step 3: methyl 4-cyclopropyl-3-(N-(2-(pyridin-2-yl)-5-(trifluoromethyl)phenyl)sulfamoyl)benzoate: A degassed mixture of the product from Step 2 above (0.152 g, 0.295 mmol) and Pd-174 (0.021 g, 0.029 mmol) in THF (4.5 ml) was treated with 0.5 M cyclopropylzinc(II) bromide in THF (1.89 ml, 0.944 mmol). The resultant mixture was heated at 60° C. overnight. Additional Pd-174 (0.021 g, 0.029 mmol) and 0.5 M cyclopropylzinc(II) bromide in THF (1.89 ml, 0.944 mmol) added and heating continued for 2 h. Upon cooling to RT, the mixture was concentrated in vacuo onto silica and purified by chromatography on silica gel (24 g cartridge, 0-100% EtOAc/isohexane) to afford the title compound (0.150 g, 0.280 mmol, 95% yield, 89% purity) as a light yellow solid. UPLC-MS (Method 1): m/z 477.3 (M+H)$^+$, 475.2 (M−H)$^−$, at 1.84 min.

Step 4: 4-cyclopropyl-3-(N-(2-(pyridin-2-yl)-5-(trifluoromethyl)phenyl)sulfamoyl)benzoic acid: A solution of the product from Step 3 above (0.150 g, 0.280 mmol, 89% purity) in THF (5 ml) and water (5 ml) was treated with LiOH(s) (15 mg, 0.630 mmol). The resultant mixture was stirred at RT for 24 h. The mixture was concentrated in vacuo and the residue was acidified to pH 6 with 10% w/v citric acid(aq). The resultant precipitate was collected by filtration to afford the title compound (0.125 g, 0.262 mmol, 94% yield, 97% purity) as a yellow solid. UPLC-MS (Method 1): m/z 463.3 (M+H)$^+$, 461.2 (M−H)$^−$, at 1.67 min. $^1$H NMR (500 MHz, DMSO-d$_6$) δ 13.43 (s, 1H), 13.28 (s, 1H), 8.74 (d, J=4.9 Hz, 1H), 8.41 (d, J=1.9 Hz, 1H), 8.19-8.01 (m, 3H), 7.92 (dd, J=8.2, 1.9 Hz, 1H), 7.71 (d, J=2.0 Hz, 1H), 7.57-7.44 (m, 2H), 6.99 (d, J=8.3 Hz, 1H), 2.55-2.46 (m, 1H), 0.75-0.67 (m, 2H), 0.68-0.53 (m, 2H).

Step 5: 4-cyclopropyl-3-(N-(2-(piperidin-2-yl)-5-(trifluoromethyl)phenyl)sulfamoyl)benzoic acid: The product from Step 4 above (0.075 g, 0.157 mmol, 97% purity) was dissolved in AcOH (5 ml) and treated with 5% Rh/C (0.05 g, 24.3 μmol). The reaction mixture was stirred at 50° C. under H$_2$ (5 bar) for 24 h. The mixture was cooled, filtered through Celite®, washing with MeOH (20 ml), and the filtrate concentrated in vacuo. The residue was purified by preparative HPLC (Waters, Acidic (0.1% Formic acid), Acidic, Waters X-Select Prep-C18, 5 μm, 19×50 mm column, 10-40% MeCN in Water) to afford the title compound (7.7 mg, 0.016 mmol, 10% yield, 96% purity) as a white solid. UPLC-MS (Method 1): m/z 469.4 (M+H)$^+$, 467.2 (M−H)$^−$, at 0.90 min. $^1$H NMR (500 MHz, DMSO-d$_6$) δ 8.52 (d, J=1.9 Hz, 1H), 7.81 (dd, J=8.1, 1.9 Hz, 1H), 7.50 (d, J=1.8 Hz, 1H), 7.23 (d, J=7.9 Hz, 1H), 6.95-6.74 (m, 2H), 4.32-4.26 (m, 1H), 3.40-3.33 (m, 1H), 3.27-3.19 (m, 1H), 2.98-2.89 (m, 1H), 2.09-1.94 (m, 1H), 1.92-1.76 (m, 3H), 1.64-1.43 (m, 2H), 1.14-0.96 (m, 2H), 0.88-0.73 (m, 2H). Three exchangeable protons not observed.

Example 17: 3-(N-(2-cyclohexyl-5-(methylsulfonyl)phenyl)sulfamoyl)-4-cyclopropylbenzoic Acid

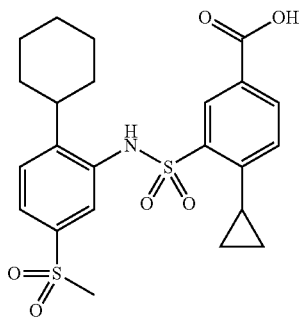 [SMILES: CS(=O)(=O)c1ccc(C2CCCCC2)c(NS(=O)(=O)c2cc(C(=O)O)ccc2C2CC2)c1]

Step 1: 4-(methylsulfonyl)-2',3',4',5'-tetrahydro-[1,1'-biphenyl]-2-amine: A mixture of 2-bromo-5-(methylsulfonyl)aniline (400 mg, 1.60 mmol), 2-(cyclohex-1-en-1-yl)-4,4,5,5-tetramethyl-1,3,2-dioxaborolane (0.45 ml, 2.09 mmol), 1 M K$_3$PO$_4$ (aq) (2.80 ml, 2.80 mmol) and dioxane (16 ml) was treated with XPhos Pd G3 (68 mg, 0.080 mmol). The resultant mixture was degassed with N$_2$ for 15 min and then heated at 80° C. for 20 h. The mixture was allowed to cool to RT, filtered through Celite®, washing with MeOH (10 ml), and then concentrated in vacuo. The residue was purified by chromatography on silica gel (12 g cartridge, 0-35% EtOAc/isohexane) to afford the title compound (311 mg, 1.24 mmol, 77% yield) as a pale yellow solid. UPLC-MS (Method 1): m/z 252.3 (M+H)$^+$ at 1.32 min.

Step 2: 2-cyclohexyl-5-(methylsulfonyl)aniline: 5% Pd/C (Type 87L) (31 mg, 5.83 μmol) was added to a solution of the product from Step 1 above (311 mg, 1.24 mmol) in EtOH (12 ml). The reaction mixture was stirred at RT under H$_2$ (1 bar) for 4 h and then at RT under H$_2$ (3 bar) for 17 h. The mixture was filtered and treated with 5% Pd/C (Type 87L) (100 mg, 18.8 μmol). The reaction mixture was stirred at RT under H$_2$ (3 bar) for 16 h. The reaction mixture was filtered through a PTFE filter and the filtrate concentrated in vacuo to afford the title compound (290 mg, 1.12 mmol, 91% yield, 98% purity) as an off-white solid. UPLC-MS (Method 1): m/z 254.3 (M+H)$^+$ at 1.33 min.

Step 3: Methyl 3-(benzylthio)-4-cyclopropylbenzoate: To a degassed mixture of methyl 3-bromo-4-cyclopropylbenzoate (850 mg, 3.33 mmol), DIPEA (1.2 ml, 6.87 mmol) and XantPhos Pd G3 (300 mg, 0.316 mmol) in dioxane (13 ml) was added phenylmethanethiol (425 μl, 3.62 mmol) and the mixture was heated to 100° C. and stirred overnight. The mixture was cooled to RT, concentrated in vacuo onto silica and purified by chromatography on silica gel (40 g cartridge, 20-70% DCM/isohexane) to afford the title compound (600 mg, 1.91 mmol, 58% yield, 95% purity) as a orange oil.

$^1$H NMR (500 MHz, DMSO-d6) δ 7.86 (d, J=1.8 Hz, 1H), 7.67 (dd, J=8.1, 1.8 Hz, 1H), 7.40-7.35 (m, 2H), 7.35-7.29 (m, 2H), 7.28-7.22 (m, 1H), 7.04 (d, J=8.1 Hz, 1H), 4.27 (s, 2H), 3.83 (s, 3H), 2.21-2.12 (m, 1H), 1.06-0.99 (m, 2H), 0.75-0.68 (m, 2H).

Step 4: Methyl 3-(chlorosulfonyl)-4-cyclopropylbenzoate: A mixture of the product from Step 3 above (600 mg, 1.91 mmol, 95% purity), AcOH (110 μl, 1.92 mmol) and water (250 μl, 13.9 mmol) in MeCN (9 ml) at −10° C. was treated with 1,3-dichloro-5,5-dimethylimidazolidine-2,4-dione (565 mg, 2.87 mmol). The mixture was stirred at −10° C. for 3 h. The mixture was diluted with water (50 ml) and extracted with DCM (2×50 ml). The organic phases were combined, dried over MgSO$_4$, filtered, concentrated in vacuo onto silica and then purified by chromatography on silica gel (40 g cartridge, 0-50% DCM/Isohexane) to afford the title compound (440 mg, 1.52 mmol, 80% yield, 95% purity) as a pale yellow oil. $^1$H NMR (500 MHz, DMSO-d$_6$) δ 8.36 (d, J=2.0 Hz, 1H), 7.77 (dd, J=8.2, 2.1 Hz, 1H), 6.84 (d, J=8.2 Hz, 1H), 3.84 (s, 3H), 3.22-3.01 (m, 1H), 1.08-0.98 (m, 2H), 0.79-0.70 (m, 2H).

Step 5: methyl 3-(N-(2-cyclohexyl-5-(methylsulfonyl)phenyl)sulfamoyl)-4-cyclopropylbenzoate: A solution of the product from Step 2 above (76 mg, 0.294 mmol, 98% purity), the product from Step 4 above (94 mg, 0.323 mmol, 95% purity) and pyridine (0.12 ml, 1.48 mmol) in DCM (1.0 ml) was stirred at RT for 19 h. The reaction mixture was directly purified by chromatography on silica gel (12 g cartridge, 0-50% EtOAc/isohexane) to afford the title compound (140 mg, 0.284 mmol, 97% yield) as an off-white solid. UPLC-MS (Method 1): m/z 514.3 (M+Na)⁺, 490.2 (M−H)⁻ at 1.63 min.

Step 6: 3-(N-(2-cyclohexyl-5-(methylsulfonyl)phenyl)sulfamoyl)-4-cyclopropylbenzoic acid: 1 M LiOH(aq) (1.13 ml, 1.13 mmol) was added to a solution of the product from Step 5 above (139 mg, 0.283 mmol) in THF (2.3 ml) at RT. The resultant mixture was stirred at RT for 21 h. The reaction mixture was concentrated in vacuo and the residue diluted with water (7 ml) and washed with TBME (7 ml). The aqueous phase was acidified using 1 M HCl until pH 4-5 and then extracted with EtOAc (3×7 ml). The extracts were combined and dried by passage through a phase separator, then concentrated in vacuo to afford the title compound (119 mg, 0.240 mmol, 85% yield, 96% purity) as a pale yellow solid. UPLC-MS (Method 1): m/z 500.3 (M+Na)⁺, 476.2 (M−H)⁻, at 1.47 min. ¹H NMR (500 MHz, DMSO-d₆) δ 13.22 (br s, 1H), 10.26 (br s, 1H), 8.22 (d, J=1.9 Hz, 1H), 7.98 (dd, J=8.2, 1.9 Hz, 1H), 7.72 (br d, J=8.2 Hz, 1H), 7.57 (d, J=2.0 Hz, 1H), 7.52 (d, J=8.3 Hz, 1H), 7.15 (d, J=8.3 Hz, 1H), 3.09 (s, 3H), 2.85-2.75 (m, 2H), 1.67-1.58 (m, 3H), 1.27-1.05 (m, 9H), 0.91-0.84 (m, 2H).

Example 18: 3-(N-(5-cyano-2-cyclohexylphenyl)sulfamoyl)-4-cyclopropylbenzoic Acid

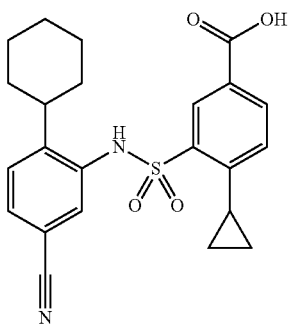 [SMILES: N#Cc1ccc(C2CCCCC2)c(NS(=O)(=O)c2cc(C(=O)O)ccc2C2CC2)c1]

Step 1: 2-amino-2',3',4',5'-tetrahydro-[1,1'-biphenyl]-4-carbonitrile: A mixture of 3-amino-4-bromobenzonitrile (500 mg, 2.54 mmol), 2-(cyclohex-1-en-1-yl)-4,4,5,5-tetramethyl-1,3,2-dioxaborolane (0.70 ml, 3.26 mmol), 1 M K₃PO₄ (aq) (4.50 ml, 4.50 mmol) and dioxane (13.5 ml) was treated with XPhos Pd G3 (107 mg, 0.127 mmol). The resultant mixture was degassed with N₂ for 10 min and then heated at 80° C. for 2 h. The mixture was allowed to cool to RT, filtered through Celite®, washing with MeOH (5 ml), and then concentrated in vacuo. The residue was purified by chromatography on silica gel (12 g cartridge, 0-20% EtOAc/isohexane) to afford the title compound (354 mg, 1.77 mmol, 70% yield, 99% purity) as a light brown solid. UPLC-MS (Method 1): m/z 199.3 (M+H)⁺ at 1.56 min.

Step 2: 3-amino-4-cyclohexylbenzonitrile: 10% Pd/C (Type 39) (32 mg, 15.0 µmol) was added to a solution of the product from Step 1 above (60 mg, 0.300 mmol, 99% purity) in THF (2 ml). The reaction mixture was stirred at RT under H₂ (3 bar) for 2 h. The mixture was then treated with 5% Pd/C (Type 87L) (71 mg, 13.3 µmol) and the reaction mixture was stirred at RT under H₂ (5 bar) for 16 h. The reaction mixture was filtered through a PTFE frit, washing with MeOH, and the filtrate concentrated in vacuo to afford the title compound (60 mg, 0.177 mmol, 59% yield, 59% purity) as a brown oil. UPLC-MS (Method 1): m/z 201.3 (M+H)⁺ at 1.57 min.

Step 3: methyl 3-(N-(5-cyano-2-cyclohexylphenyl)sulfamoyl)-4-cyclopropylbenzoate: A solution of the product from Step 2 above (60 mg, 0.177 mmol, 59% purity), the product from Example 17 Step 4 (97 mg, 0.336 mmol, 95% purity) and pyridine (0.120 ml, 1.49 mmol) in DCM (1 ml) was stirred at RT for 3 days. The reaction mixture was directly purified by chromatography on silica gel (12 g cartridge, 0-50% EtOAc/isohexane) to afford the title compound (23.3 mg, 0.052 mmol, 30% yield, 98% purity) as a colourless oil. UPLC-MS (Method 1): m/z 439.4 (M+H)⁺, 437.3 (M−H)⁻, at 1.76 min.

Step 4: 3-(N-(5-cyano-2-cyclohexylphenyl)sulfamoyl)-4-cyclopropylbenzoic acid: 1 M LiOH(aq) (0.210 ml, 0.210 mmol) was added to a solution of the product from Step 3 above (23.3 mg, 0.052 mmol, 98% purity) in THF (0.42 ml). The resultant mixture was stirred at RT for 21 h. The reaction mixture was concentrated in vacuo and the residue was diluted with water (2 ml) and then washed with TBME (2 ml). The aqueous phase was acidified using 1 M HCl until pH 4-5 and then extracted with EtOAc (3×2 ml). The extracts were combined, dried by passage through a phase separator, then concentrated in vacuo to afford the title compound (19.0 mg, 0.043 mmol, 83% yield, 96% purity) as a cream solid. UPLC-MS (Method 1): m/z 425.5 (M+H)⁺, 423.3 (M−H)⁻, at 1.61 min. ¹H NMR (500 MHz, DMSO-d₆) δ 13.22 (brs, 1H), 10.29 (brs, 1H), 8.19 (d, J=1.9 Hz, 1H), 7.99 (dd, J=8.2, 1.9 Hz, 1H), 7.65 (br d, J=8.1 Hz, 1H), 7.49 (d, J=1.8 Hz, 1H), 7.43 (d, J=8.1 Hz, 1H), 7.15 (d, J=8.3 Hz, 1H), 2.87-2.74 (m, 1H), 2.74-2.60 (m, 1H), 1.65-1.52 (m, 3H), 1.21-0.99 (m, 9H), 0.93-0.82 (m, 2H).

Example 19: 3-(N-(5-cyano-2-(piperidin-2-yl)phenyl)sulfamoyl)-4-cyclopropylbenzoic Acid

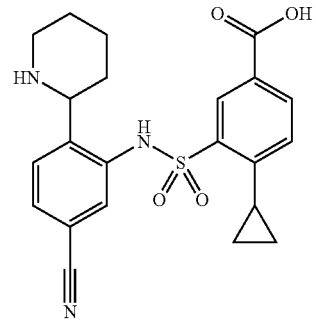 [SMILES: N#Cc1ccc(C2CCCCN2)c(NS(=O)(=O)c2cc(C(=O)O)ccc2C2CC2)c1]

Step 1: tert-butyl 6-(2-amino-4-cyanophenyl)-3,4-dihydropyridine-1-carboxylate: A mixture of 3-amino-4-bromobenzonitrile (354 mg, 1.80 mmol), tert-butyl 6-(4,4,5,5-tetramethyl-1,3,2-dioxaborolan-2-yl)-3,4-dihydropyridine-1-carboxylate (666 mg, 2.15 mmol), K₃PO₄(s) (762 mg, 3.59 mmol) was combined with PdCl₂(AmPhos)₂ (127 mg, 0.179 mmol). The solid mixture was degassed with N₂ for 5 min, then dioxane (9 ml) and water (2.25 ml) were added. The resultant mixture was degassed with N₂ for 5 min and then heated at 80° C. for 16 h. The resultant mixture was concentrated in vacuo and the residue purified by chromatography on silica gel (12 g cartridge, 0-40% EtOAc/isohexane) to afford the title compound (479 mg, 1.20 mmol, 67% yield, 75% purity) as an orange solid. UPLC-MS (Method 1): m/z 200.3 (M+H−Boc)⁺ at 1.52 min.
¹H NMR (500 MHz, Chloroform-d) δ 7.12 (d, J=7.9 Hz, 1H), 6.98 (d, J=7.8 Hz, 1H), 6.86 (br s, 1H), 5.31 (t, J=3.7

Hz, 1H), 3.73 (t, J=5.4 Hz, 2H), 2.29 (td, J=6.8, 3.7 Hz, 2H), 1.90 (dt, J=10.9, 6.5 Hz, 2H), 1.11 (s, 9H). Two exchangeable protons not observed.

Step 2: tert-butyl 6-(4-cyano-2-(2-cyclopropyl-5-(methoxycarbonyl)phenylsulfonamido)phenyl)-3,4-dihydropyridine-1-carboxylate: The product from Example 17 Step 4 (261 mg, 0.902 mmol, 95% purity) was dissolved in pyridine (2 ml) and stirred for 5 min. The product from Step 1 above (300 mg, 0.752 mmol, 75% purity) was added to the solution and then the resultant mixture was stirred at RT for 23 h. A premixed solution of the product from Example 17 Step 4 (261 mg, 0.902 mmol, 95% purity) in pyridine (2.0 ml) was added to the reaction mixture and the resultant mixture stirred at RT for 22 h. The reaction mixture was concentrated in vacuo and the residue purified by chromatography on silica gel (24 g cartridge, 0-40% EtOAc/isohexane) to afford the title compound (393 mg, 0.599 mmol, 80% yield, 82% purity) as a cream foam. UPLC-MS (Method 1): m/z 560.3 (M+Na)⁺, 536.2 (M−H)⁻, at 1.81 min.

Step 3: methyl 3-(N-(5-cyano-2-(piperidin-2-yl)phenyl)sulfamoyl)-4-cyclopropylbenzoate: TFA (2.20 ml, 28.6 mmol) was added to a solution of the product from Step 2 above (363 mg, 554 µmol, 82% purity) in DCM (2.2 ml) at RT. The resultant mixture was stirred for 17 h, then concentrated in vacuo. The residue was dissolved in THF (4 ml) and treated with Et₃N (100 µl, 0.72 mmol) and NaBH(OAc)₃ (305 mg, 1.44 mmol). The resultant mixture was stirred at RT for 23 h. The mixture was quenched with 1 M NaOH(aq) (~5 ml) until pH 8-9 and then EtOAc (4 ml) was added. The phases were separated and then the aqueous phase was extracted with EtOAc (3×4 ml). The organic phases were combined, dried by passage through a phase separator, and then concentrated in vacuo. The crude product was partially purified by chromatography on silica gel (12 g cartridge, 0-7% MeOH/DCM) and then purified by chromatography (24 g reverse phase C18 cartridge, 15-50% MeCN/0.1% formic acid(aq)) to afford the title compound (129 mg, 285 µmol, 52% yield, 97% purity) as an off-white solid. UPLC-MS (Method 1): m/z 440.4 (M+H)⁺, 438.3 (M−H)⁻, at 0.92 min.

Step 4: 3-(N-(5-cyano-2-(piperidin-2-yl)phenyl)sulfamoyl)-4-cyclopropylbenzoic acid: 1 M LiOH(aq) (1.15 ml, 1.15 mmol) was added to a suspension of the product from Step 3 above (129 mg, 285 µmol, 97% purity) in THF (2.3 ml) at RT. The resultant mixture was stirred at RT for 23 h. The reaction mixture was concentrated in vacuo to remove the THF. The residue was diluted with water (10 ml) and then washed with TBME (5 ml). The aqueous phase was acidified using 1 M HCl(aq) until pH 4-5 and then EtOAc (10 ml) and THF (5 ml) were added. The phases were separated and then the aqueous phase was extracted with EtOAc (2×10 ml). The organic phases were combined, dried by passage through a phase separator, and concentrated in vacuo. The crude product was purified by chromatography (24 g reverse phase C18 cartridge, 15-40% MeCN/0.1% formic acid(aq)) to afford the title compound (71 mg, 162 µmol, 57% yield, 97% purity) as an off-white solid. UPLC-MS (Method 1): m/z 426.4 (M+H)⁺, 424.3 (M−H)⁻ at 0.81 min. ¹H NMR (500 MHz, DMSO-d₆) δ 12.90 (br s, 1H), 9.31 (br s, 2H), 8.49 (d, J=1.9 Hz, 1H), 7.83 (dd, J=8.1, 1.9 Hz, 1H), 7.42 (d, J=1.6 Hz, 1H), 7.22 (d, J=7.8 Hz, 1H), 6.99 (dd, J=7.8, 1.7 Hz, 1H), 6.90 (d, J=8.2 Hz, 1H), 4.31 (dd, J=11.8, 3.3 Hz, 1H), 3.40-3.35 (m, 1H), 3.25-3.19 (m, 1H), 3.00-2.86 (m, 1H), 2.02-1.75 (m, 4H), 1.63-1.44 (m, 2H), 1.12-1.02 (m, 2H), 0.91-0.74 (m, 2H).

Example 20: 4-cyclopropyl-3-(N-(5-(methylsulfonyl)-2-(piperidin-2-yl)phenyl)sulfamoyl)benzoic Acid

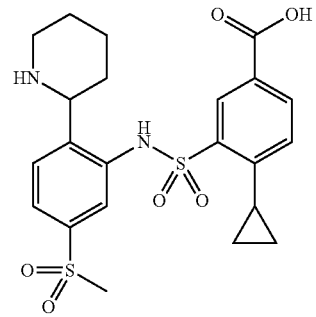 [SMILES: CS(=O)(=O)c1ccc(C2CCCCN2)c(NS(=O)(=O)c2cc(C(=O)O)ccc2C2CC2)c1]

Step 1: tert-butyl 6-(2-amino-4-(methylsulfonyl)phenyl)-3,4-dihydropyridine-1-carboxylate: A mixture of 2-bromo-5-(methylsulfonyl)aniline (250 mg, 1.00 mmol), tert-butyl 6-(4,4,5,5-tetramethyl-1,3,2-dioxaborolan-2-yl)-3,4-dihydropyridine-1-carboxylate (340 mg, 1.10 mmol), K₃PO₄(s) (424 mg, 2.00 mmol), PdCl₂(AmPhos)₂ (85 mg, 0.12 mmol) in dioxane (2 ml) and water (0.5 ml) was degassed with N₂ for 10 min, and then heated at 80° C. for 1 h. The reaction mixture was allowed to cool to RT, then was filtered through Celite®, washing with EtOAc (5 ml), and concentrated in vacuo. The crude product was purified by chromatography on silica gel (12 g cartridge, 0-70% EtOAc/isohexane) to afford the title compound (273 mg, 775 µmol, 78%) as a yellow solid. UPLC-MS (Method 1): m/z 375.4 (M+Na)⁺ at 1.30 min.

Step 2: tert-butyl 6-(2-((2-cyclopropyl-5-(methoxycarbonyl)phenyl)sulfonamido)-4-(methylsulfonyl)phenyl)-3,4-dihydropyridine-1-carboxylate: The product from Example 17 Step 4 (235 mg, 813 µmol, 95% purity) was dissolved in pyridine (2 ml) and stirred for 5 min. The product from Step 1 above (273 mg, 775 µmol) was added and then the resultant mixture was stirred vigorously at RT over the weekend. The reaction mixture was concentrated in vacuo and then the residue was partitioned between EtOAc (5 ml) and saturated NaHCO₃ (aq) (5 ml) and then the phases separated. The aqueous phase was extracted with EtOAc (2×5 ml) and then the organic phases were combined and sequentially washed with water (10 ml) and brine (30 ml), dried by passage through a phase separator, and then concentrated in vacuo. The resultant orange oil was azeotroped with PhMe (10 ml) to afford the title compound (421 mg, 0.677 mmol, 87% yield, 95% purity) as a pale orange solid. UPLC-MS (Method 1): m/z 491.3 (M+H−Boc)⁺, 589.2 (M−H)⁻, at 1.64 min.

Step 3: methyl 4-cyclopropyl-3-(N-(5-(methylsulfonyl)-2-(piperidin-2-yl)phenyl)sulfamoyl)benzoate: TFA (2.6 ml, 33.7 mmol) was added to a solution of the product from Step 2 above (421 mg, 677 µmol, 95% purity) in DCM (2.6 ml) at RT and the resultant mixture was stirred for 1 h, then concentrated in vacuo. The residue was dissolved in THF (4 ml) and treated with Et₃N (0.12 ml, 0.88 mmol) and NaBH (OAc)₃(s) (373 mg, 1.76 mmol). The resultant mixture was stirred at RT for 19 h. The mixture was quenched with 2 M NaOH(aq) (~5 ml) until pH 9 and then EtOAc (4 ml) was added. The phases were separated and then the aqueous phase was extracted with EtOAc (3×4 ml). The organic phases were combined, dried by passage through a phase separator, and then concentrated in vacuo. The crude product was purified by chromatography on silica gel (12 g cartridge, 0-5% MeOH/DCM) to afford the title compound (199 mg, 396 µmol, 58% yield, 98% purity) as a pale-yellow solid. UPLC-MS (Method 1): m/z 493.3 (M+H)⁺, 491.2 (M−H)⁻ at 0.86 min.

Step 4: 4-cyclopropyl-3-(N-(5-(methylsulfonyl)-2-(piperidin-2-yl)phenyl)sulfamoyl)benzoic acid: 1 M LiOH(aq) (1.60 ml, 1.60 mmol) was added to a suspension of the product from Step 3 above (199 mg, 396 µmol, 98% purity) in THF (3.2 ml) at RT. The resultant cloudy mixture was stirred at RT for 16 h. The reaction mixture was concentrated in vacuo to remove the THF. The residue was diluted with water (10 ml) and then washed with TBME (6 ml). The aqueous phase was acidified using 1 M HCl(aq) until pH 4-5 and then EtOAc (10 ml) and THF (5 ml) were added. The phases were separated and then the aqueous phase was extracted with EtOAc (2×10 ml). The organic phases were combined, dried by passage through a phase separator, and concentrated in vacuo. The crude product was purified by preparative HPLC (Waters, Acidic (0.1% Formic acid), Acidic, Waters X-Select Prep-C18, 5 µm, 19×50 mm column, 5-30% MeCN in Water) in two portions to afford, in total, the title compound (67 mg, 140 µmol, 35% yield, 99% purity) as an off-white solid. UPLC-MS (Method 1): m/z 479.2 (M+H)⁺, 477.3 (M−H)⁻, at 0.71 min. ¹H NMR (500 MHz, DMSO-d₆) δ 8.48 (d, J=1.9 Hz, 1H), 7.83-7.73 (m, 2H), 7.29 (d, J=8.0 Hz, 1H), 7.05 (dd, J=7.9, 1.9 Hz, 1H), 6.83 (d, J=8.2 Hz, 1H), 4.31 (dd, J=11.6, 3.3 Hz, 1H), 3.38-3.32 (m, 1H), 3.26-3.20 (m, 1H), 2.96-2.85 (m, 4H), 1.99-1.74 (m, 4H), 1.62-1.44 (m, 2H), 1.10-1.00 (m, 2H), 0.85-0.72 (m, 2H).

Example 21: 3-(N-(5-cyano-4-fluoro-2-(piperidin-2-yl)phenyl)sulfamoyl)-4-cyclopropylbenzoic Acid

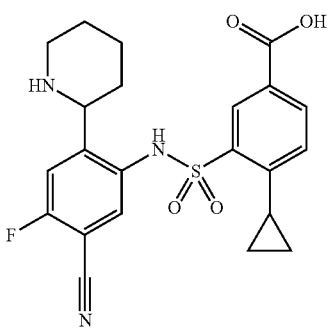

Step 1: tert-butyl 6-(2-amino-4-cyano-5-fluorophenyl)-3,4-dihydropyridine-1-carboxylate: Two reactions were performed on a 30 mg and 150 mg scale using the following procedure and combined. A mixture of 5-amino-4-bromo-2-fluorobenzonitrile (150 mg, 698 µmol), tert-butyl 6-(4,4,5,5-tetramethyl-1,3,2-dioxaborolan-2-yl)-3,4-dihydropyridine-1-carboxylate (261 mg, 837 µmol, 99% purity), K₃PO₄ (s) (296 mg, 1.40 mmol), PdCl₂(AmPhos)₂ (59 mg, 83 µmol) in dioxane (1.6 ml) was sparged with N₂ for 5 min, then heated at 80° C. for 30 min. Water (0.4 ml) was added and the reaction heated at 80° C. for 3.5 h. The reaction mixture was allowed to cool to RT, combined with the 30 mg scale reaction, filtered through Celite®, washing with EtOAc (10 ml), and concentrated in vacuo. The crude product was purified by chromatography on silica gel (24 g cartridge, 0-50% EtOAc/heptane) to afford the title compound (183 mg, 571 µmol, 68% yield, 99% purity) as a yellow-brown solid. UPLC-MS (Method 1): m/z 218.3 (M+H−Boc)⁺ at 1.57 min.

Step 2: tert-butyl 6-(4-cyano-2-((2-cyclopropyl-5-(methoxycarbonyl)phenyl)sulfonamido)-5-fluorophenyl)-3,4-dihydropyridine-1-carboxylate: The product from Example 17 Step 4 (173 mg, 599 µmol, 95% purity) was dissolved in pyridine (2 ml) and stirred for 5 min. The product from Step 1 above (183 mg, 571 µmol, 99% purity) was added and then the resultant mixture was stirred vigorously at RT for 20 h. Additional product from Example 17 Step 4 (173 mg, 599 µmol, 95% purity) in pyridine (0.50 ml) was premixed for 5 mins, then added to the reaction mixture, which was stirred vigorously at RT for 24 h. The reaction mixture was concentrated in vacuo. The residue was dissolved in EtOAc (8 ml), washed with saturated NaHCO₃ (aq) (5 ml) and then the aqueous phase was extracted with EtOAc (2×5 ml). The organic phases were combined, washed with brine (5 ml), dried by passage through a phase separator, and then concentrated in vacuo. The crude product was purified by chromatography on silica gel (12 g cartridge, 0-40% EtOAc/heptane) to afford the title compound (279 mg, 0.49 mmol, 85% yield, 97% purity) as a pale yellow solid. UPLC-MS (Method 1): m/z 456.3 (M+H−Boc)⁺, 554.3 (M−H)⁻, at 1.84 min.

Step 3: methyl 3-(N-(5-cyano-4-fluoro-2-(piperidin-2-yl)phenyl)sulfamoyl)-4-cyclopropylbenzoate: TFA (2.0 ml, 26 mmol) was added to a solution of the product from Step 2 above (279 mg, 487 µmol, 97% purity) in DCM (2.0 ml) at RT and the resultant mixture stirred for 1 h, and then concentrated in vacuo. The residue was dissolved in THF (4 ml) and treated with Et₃N (88 µL, 633 µmol) and NaBH(OAc)₃(s) (268 mg, 1.27 mmol). The resultant mixture was stirred at RT for 3 h. The reaction mixture was quenched with saturated NaHCO₃ (aq) (~7 ml) until pH ~8 and then EtOAc (5 ml) was added. The phases were separated and then the aqueous phase was extracted with EtOAc (2×5 ml). The organic phases were combined and washed with brine (5 ml), dried by passage through a phase separator, and then concentrated in vacuo. The crude product was purified by chromatography on silica gel (12 g cartridge, 0-100% (3:1 EtOAc/EtOH)/heptane) to afford the title compound (180 mg, 393 µmol, 81% yield) as a yellow solid. UPLC-MS (Method 1): m/z 458.3 (M+H)⁺, 456.3 (M−H)⁻, at 0.96 min.

Step 4: 3-(N-(5-cyano-4-fluoro-2-(piperidin-2-yl)phenyl) sulfamoyl)-4-cyclopropylbenzoic acid: 1 M LiOH(aq) (1.60 ml, 1.60 mmol) was added to a suspension of the product from Step 3 above (180 mg, 393 µmol) in THF (3.2 ml) at RT. The resultant mixture was stirred at RT for 17 h. The reaction mixture was concentrated in vacuo to remove the THF. The residue was diluted with water (10 ml) and then washed with TBME (6 ml). The aqueous phase was acidified using 1 M HCl(aq) until pH 4-5 and then EtOAc (10 ml) was added. The phases were separated and then the aqueous phase was extracted with EtOAc (2×10 ml). The organic phases were combined, dried by passage through a phase separator, and concentrated in vacuo to afford the title compound (122 mg, 0.27 mmol, 68% yield, 97% purity) as a light-yellow solid. UPLC-MS (Method 1): m/z 444.3 (M+H)⁺, 442.3 (M−H)⁻, at 0.84 min. ¹H NMR (500 MHz, DMSO-d₆) δ 12.86 (br s, 1H), 9.35 (br s, 1H), 8.45 (d, J=1.9 Hz, 1H), 7.82 (dd, J=8.2, 1.9 Hz, 1H), 7.37 (d, J=6.0 Hz, 1H), 7.26 (d, J=10.1 Hz, 1H), 6.90 (d, J=8.3 Hz, 1H), 4.38-4.24 (m, 1H), 3.42-3.35 (m, 1H), 3.24-3.17 (m, 1H), 3.00-2.86 (m, 1H), 1.90-1.73 (m, 4H), 1.60-1.43 (m, 2H), 1.11-1.00 (m, 2H), 0.88-0.74 (m, 2H).

Example 22: 3-(N-(4-chloro-5-cyano-2-(piperidin-2-yl)phenyl)sulfamoyl)-4-cyclopropylbenzoic Acid

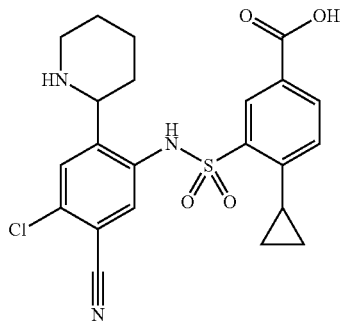 [SMILES: N#Cc1cc(NS(=O)(=O)c2cc(C(=O)O)ccc2C2CC2)c(C2CCCCN2)cc1Cl]

Step 1: 4-bromo-2-chloro-5-nitrobenzonitrile: 4-bromo-2-chlorobenzonitrile (5.00 g, 23.1 mmol) was dissolved in conc. sulfuric acid (36 ml, 645 mmol) was cooled to 0° C. and then nitric acid(aq) (22 ml, 330 mmol, 68% w/v) was added. The mixture was stirred at 0° C. for 30 min, then at RT overnight. The reaction mixture was cooled to 0° C. before the slow addition of water (50 ml). The reaction mixture was allowed to warm to RT and was extracted with DCM (2×100 ml). The organic phases were combined and passed through a phase separator, and then concentrated in vacuo to afford the title compound (6.36 g, 22.6 mmol, 98% yield, 93% purity) as an orange solid. UPLC-MS (Method 1): m/z no ionisation at 1.36 min. $^1$H NMR (500 MHz, DMSO-$d_6$) δ 8.81 (s, 1H), 8.52 (s, 1H).

Step 2: 5-amino-4-bromo-2-chlorobenzonitrile: The product from Step 1 above (5.36 g, 19.1 mmol, 93% purity) was dissolved in AcOH (40 ml) and iron powder (2.20 g, 39.4 mmol) was added with vigorous stirring. The resultant mixture was stirred at RT overnight. The reaction mixture was diluted with EtOAc, filtered through Celite®, and concentrated in vacuo onto silica. The crude product was purified by chromatography on silica gel (220 g cartridge, 0-100% TBME/isohexane) to afford the title compound (3.40 g, 14.4 mmol, 76% yield, 98% purity) as a cream solid. UPLC-MS (Method 2): m/z 229.4 (M−H)$^-$ at 1.32 min. $^1$H NMR (500 MHz, DMSO-$d_6$) δ 7.79 (s, 1H), 7.17 (s, 1H), 5.99 (s, 2H).

Step 3: tert-butyl 6-(2-amino-5-chloro-4-cyanophenyl)-3,4-dihydropyridine-1-carboxylate: Two reactions were performed on a 31 mg and 220 mg scale using the following procedure and combined. A mixture of the product from Step 1 above (220 mg, 931 μmol, 98% purity), tert-butyl 6-(4,4,5,5-tetramethyl-1,3,2-dioxaborolan-2-yl)-3,4-dihydropyridine-1-carboxylate (320 mg, 1.02 mmol, 99% purity), $K_3PO_4$(s) (395 mg, 1.86 mmol), PdCl$_2$(AmPhos)$_2$ (79 mg, 0.11 mmol) in dioxane (2 ml) and water (0.5 ml) was sparged with N$_2$ for 10 min, then heated at 80° C. for 3 h. The reaction mixture was allowed to cool to RT and was then combined with the 30 mg scale reaction, filtered through Celite®, washing with EtOAc (10 ml), and then concentrated in vacuo. The crude product was purified by chromatography on silica gel (24 g cartridge, 0-40% EtOAc/heptane) to afford the title compound (280 mg, 747 μmol, 70% yield, 89% purity) as a yellow-brown solid. UPLC-MS (Method 1): m/z 234.2 (M+H−Boc)$^+$ at 1.64 min. $^1$H NMR (500 MHz, DMSO-$d_6$) δ 7.13 (s, 1H), 7.02 (s, 1H), 5.34 (br s, 2H), 5.27 (t, J=3.8 Hz, 1H), 3.65 (t, J=5.4 Hz, 2H), 2.24-2.10 (m, 2H), 1.80-1.69 (m, 2H), 1.07 (s, 9H).

Step 4: tert-butyl 6-(5-chloro-4-cyano-2-((2-cyclopropyl-5-(methoxycarbonyl)phenyl)sulfonamido)phenyl)-3,4-dihydropyridine-1-carboxylate: The product from Example 17 Step 4 (324 mg, 1.12 mmol, 95% purity) was dissolved in pyridine (2.5 ml) and stirred for 5 min. The product from Step 3 above (280 mg, 747 μmol, 89% purity) was added and the resultant mixture was stirred vigorously at RT for 17 h. Additional product from Example 17 Step 4 (216 mg, 747 μmol, 95% purity) was added and the resultant mixture was stirred vigorously at RT over the weekend. The reaction mixture was diluted with PhMe (6 ml) and concentrated in vacuo. The residue was dissolved in EtOAc (8 ml), washed with saturated NaHCO$_3$ (aq) (5 ml) and then the aqueous phase was extracted with EtOAc (2×5 ml). The organic phases were combined and washed with brine (5 ml), dried by passage through a phase separator, and concentrated in vacuo. The crude product was purified by chromatography on silica gel (24 g cartridge, 0-40% EtOAc/heptane) to afford the title compound (331 mg, 480 μmol, 64% yield, 83% purity) as a yellow foam. UPLC-MS (Method 1): m/z 472.3 (M+H−Boc)$^+$, 570.2 (M−H)$^-$, at 1.91 min.

Step 5: methyl 3-(N-(4-chloro-5-cyano-2-(piperidin-2-yl)phenyl)sulfamoyl)-4-cyclopropylbenzoate: TFA (2 ml, 26.0 mmol) was added to a solution of the product from Step 4 above (331 mg, 480 μmol, 83% purity) in DCM (2 ml) at RT and the resultant mixture stirred for 1 h and then reaction mixture was concentrated in vacuo. The residue was dissolved in THF (4 ml) and then Et$_3$N (87 μl, 624 μmol) and NaBH(OAc)$_3$ (265 mg, 1.25 mmol) were added. The resultant mixture was stirred at RT for 3 h. The reaction mixture was quenched with saturated NaHCO$_3$ (aq) (~7 ml) until pH ~8 and then EtOAc (5 ml) was added. The phases were separated, and the aqueous phase extracted with EtOAc (2×5 ml). The organic phases were combined and washed with brine (5 ml), dried by passage through a phase separator and then concentrated in vacuo. The crude product was partially purified by chromatography on silica gel (12 g cartridge, 0-100% (3:1 EtOAc/EtOH)/heptane) and then purified by chromatography on silica gel (12 g cartridge, 0-6% MeOH/DCM) to afford the title compound (129 mg, 272 μmol, 57% yield) as an off-white solid. UPLC-MS (Method 1): m/z 474.3 (M+H)$^+$, 472.2 (M−H)$^-$, at 1.10 min.

Step 6: 3-(N-(4-chloro-5-cyano-2-(piperidin-2-yl)phenyl)sulfamoyl)-4-cyclopropylbenzoic acid: 1 M LiOH(aq) (1.1 ml, 1.10 mmol) was added to a suspension of the product from Step 5 above (129 mg, 272 μmol) in THF (2.2 ml) at RT. The resultant mixture was stirred at RT for 5 h. The reaction mixture was concentrated in vacuo to remove THF. The residue was diluted with water (10 ml) and then washed with TBME (6 ml). The aqueous phase was acidified using 1 M HCl(aq) until pH 4-5 and then EtOAc (10 ml) was added. The phases were separated, and the aqueous phase extracted with EtOAc (2×10 ml). The organic phases were combined, dried by passage through a phase separator and concentrated in vacuo to afford the title compound (105 mg, 223 μmol, 82% yield, 98% purity) as a light-yellow solid. UPLC-MS (Method 1): m/z 460.3 (M+H)$^+$, 458.2 (M−H)$^-$, at 0.93 min. $^1$H NMR (500 MHz, DMSO-$d_6$) δ 12.95 (br s, 1H), 9.10 (br s, 2H), 8.46 (d, J=1.9 Hz, 1H), 7.83 (dd, J=8.1, 2.0 Hz, 1H), 7.49 (s, 1H), 7.38 (s, 1H), 6.90 (d, J=8.3 Hz, 1H), 4.42-4.31 (m, 1H), 3.42-3.36 (m, 1H), 3.25-3.13 (m, 1H), 3.01-2.88 (m, 1H), 1.92-1.74 (m, 4H), 1.60-1.45 (m, 2H), 1.11-0.99 (m, 2H), 0.86-0.74 (m, 2H).

Example 23: 4-cyclopropyl-3-(N-(2-(piperidin-2-yl)-5-(tetrazol-1-yl)phenyl)sulfamoyl)benzoic Acid

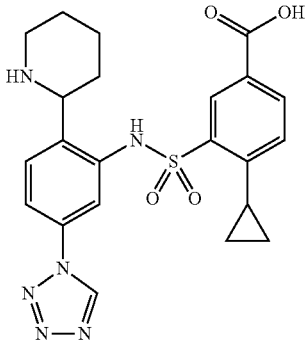

Step 1: 1-(4-bromo-3-nitrophenyl)tetrazole: A solution of 4-bromo-3-nitroaniline (3.00 g, 13.8 mmol) and triethyl orthoformate (11.5 ml, 69.1 mmol) in AcOH (54 ml) was heated at 80° C. for 1 h. Azidotrimethylsilane (2.40 ml, 18.1 mmol) was added dropwise and the resultant mixture was heated at 80° C. for 3.5 h. Additional azidotrimethylsilane (0.367 ml, 2.76 mmol) was added and the reaction heated at 80° C. for a further 1 h. The reaction mixture was allowed to cool to RT, then concentrated in vacuo and azeotroped with toluene (100 ml). The residue was purified by chromatography on silica gel (40 g cartridge, 0-2.5% MeOH/DCM) to afford the title compound (3.30 g, 12.0 mmol, 87% yield, 98% purity) as a yellow solid. UPLC-MS (Method 1) m/z no ionisation at 1.12 min. $^1$H NMR (500 MHz, DMSO-$d_6$) δ 10.20 (s, 1H), 8.70 (d, J=2.5 Hz, 1H), 8.24 (d, J=8.7 Hz, 1H), 8.19 (dd, J=8.7, 2.5 Hz, 1H).

Step 2: 2-bromo-5-(tetrazol-1-yl)aniline: Zinc powder (730 mg, 11.2 mmol) and NH$_4$Cl(s) (594 mg, 11.1 mmol) were added to a solution of the product from Step 1 above (502 mg, 1.82 mmol, 98% purity) in THF (12 ml) and water (4 ml). The suspension was stirred vigorously at RT for 4 h. Additional zinc powder (730 mg, 11.2 mmol) and NH$_4$Cl(s) (594 mg, 11.1 mmol) were added, and then the suspension was stirred vigorously at RT for 19 h. The reaction mixture was filtered through Celite®, washing sequentially with THF (20 ml) and MeCN (10 ml), and then the filtrate was concentrated in vacuo. The residue was dissolved in a mixture of THF (15 ml) and MeOH (5 ml), dried by passage through a phase separator, and then concentrated in vacuo. The resultant solid was triturated in MeCN (2 ml), filtered, and dried in vacuo to afford the title compound (277 mg, 1.08 mmol, 60% yield, 94% purity) as a cream solid.

$^1$H NMR (500 MHz, DMSO-$d_6$) δ 10.02 (s, 1H), 7.60 (d, J=8.5 Hz, 1H), 7.30 (d, J=2.6 Hz, 1H), 6.97 (dd, J=8.5, 2.6 Hz, 1H), 5.86 (s, 2H).

Step 3: tert-butyl 6-(2-amino-4-(tetrazol-1-yl)phenyl)-3,4-dihydropyridine-1(2H)-carboxylate: Two reactions were performed on a 50 mg and 227 mg scale using the following procedure and combined. A mixture of the product from Step 2 above (227 mg, 889 μmol, 94% purity), tert-butyl 6-(4,4,5,5-tetramethyl-1,3,2-dioxaborolan-2-yl)-3,4-dihydropyridine-1-carboxylate (359 mg, 1.16 mmol), K$_3$PO$_4$(s) (379 mg, 1.79 mmol), PdCl$_2$(AmPhos)$_2$ (75 mg, 0.11 mmol) in dioxane (2 ml) and water (0.5 ml) was degassed with N$_2$ for 10 min, then heated at 80° C. for 3 h. The reaction mixture was allowed to cool to RT and was then filtered through Celite®, washing with EtOAc (10 ml), and the filtrate concentrated in vacuo. The crude product was purified by chromatography on silica gel (12 g cartridge, 0-70% EtOAc/isohexane). The product was combined with the product from the 50 mg reaction to afford the title compound (253 mg, 606 μmol, 56% yield, 82% purity) was afforded as an orange solid. UPLC-MS (Method 1): m/z 343.4 (M+H)$^+$ at 1.36 min.

Step 4: tert-butyl 6-(2-((2-cyclopropyl-5-(methoxycarbonyl)phenyl)sulfonamido)-4-(tetrazol-1-yl)phenyl)-3,4-dihydropyridine-1-carboxylate: The product from Example 17 Step 4 (193 mg, 666 μmol, 95% purity) was dissolved in pyridine (2 ml) and stirred for 5 min. The product from Step 3 above (253 mg, 606 μmol, 82% purity) was added, and then the resultant mixture was stirred vigorously at RT for 20 h. Additional product from Example 17 Step 4 (87.6 mg, 303 μmol, 95% purity) was added and the reaction was stirred vigorously at RT for 2 days. The reaction mixture was diluted with PhMe (6 ml) and concentrated in vacuo. The residue was dissolved in EtOAc (8 ml), washed with saturated NaHCO$_3$ (aq) (5 ml) and the aqueous phase extracted with EtOAc (2×5 ml). The organic phases were combined and washed with brine (5 ml), dried over MgSO$_4$ and concentrated in vacuo. The crude product was purified by chromatography on silica gel (24 g cartridge, 0-70% EtOAc/isohexane) to afford the title compound (345 mg, 541 μmol, 89% yield, 91% purity) as a pale-yellow foam. UPLC-MS (Method 1): m/z 603.2 (M+Na)$^+$, 579.3 (M−H)$^-$, at 1.68 min.

Step 5: methyl 4-cyclopropyl-3-(N-(2-(piperidin-2-yl)-5-(tetrazol-1-yl)phenyl)sulfamoyl)benzoate: TFA (2.00 ml, 26.0 mmol) was added to a solution of the product from Step 4 above (345 mg, 541 μmol, 91% purity) in DCM (2 ml) at RT and the resultant mixture stirred for 30 min. The reaction mixture was concentrated in vacuo and the residue dissolved in THF (4 ml), then treated with Et$_3$N (0.11 ml, 811 μmol) and NaBH(OAc)$_3$ (344 mg, 1.62 mmol). The resultant mixture was stirred at RT for 2.5 h. The reaction mixture was quenched with saturated NaHCO$_3$ (aq) (~10 ml) until pH ~8 and then EtOAc (6 ml) was added. The phases were separated, and the aqueous phase extracted with EtOAc (2×6 ml). The organic phases were combined and concentrated in vacuo. The resultant solid was triturated with EtOAc (20 ml) and dried in vacuo to afford the title compound (298 mg, 541 μmol, 100% yield, 88% purity) as a pale yellow solid. UPLC-MS (Method 1): m/z 483.4 (M+H)$^+$, 481.2 (M−H)$^-$, at 0.45 min. $^1$H NMR (500 MHz, DMSO-$d_6$) δ 9.83 (s, 1H), 9.37 (br s, 2H), 8.55 (d, J=2.0 Hz, 1H), 7.81 (dd, J=8.2, 2.0 Hz, 1H), 7.70 (d, J=2.3 Hz, 1H), 7.32 (d, J=8.3 Hz, 1H), 7.03 (dd, J=8.2, 2.3 Hz, 1H), 6.91 (d, J=8.3 Hz, 1H), 4.32 (d, J=11.5 Hz, 1H), 3.84 (s, 3H), 3.32-3.24 (m, 1H), 2.99-2.88 (m, 1H), 2.04-1.91 (m, 1H), 1.92-1.77 (m, 4H), 1.63-1.52 (m, 2H), 1.14-1.03 (m, 2H), 0.87-0.75 (m, 2H).

Step 5: 4-cyclopropyl-3-(N-(2-(piperidin-2-yl)-5-(tetrazol-1-yl)phenyl)sulfamoyl)benzoic acid: 1 M LiOH(aq) (2.20 ml, 2.20 mmol) was added to a suspension of the product from Step 4 above (298 mg, 541 μmol, 88% purity) in THF (4.4 ml) at RT. The resultant mixture was stirred at RT for 17 h. The reaction mixture was concentrated in vacuo to remove THF. The residue was diluted with water (10 ml) and then washed with TBME (6 ml). The aqueous phase was acidified using 1 M HCl(aq) until pH 4-5 and then EtOAc (10 ml) and THF (10 ml) were added. The phases were separated, and then the aqueous phase was extracted with EtOAc (2×10 ml). The organic phases were combined and dried by passage through a phase separator, and then concentrated in vacuo. The crude product was purified by preparative HPLC (Waters, Acidic (0.1% Formic acid), Acidic, Waters X-Select Prep-C18, 5 μm, 19×50 mm column, 10-40% MeCN in Water) to afford the title compound (59 mg, 122 μmol, 23% yield, 97% purity) as an off-white solid. UPLC-MS (Method 1): m/z 469.4 (M+H)$^+$, 467.3 (M−H)$^−$, at 0.76 min. $^1$H NMR (500 MHz, DMSO-d$_6$) δ 12.89 (br s, 1H), 9.81 (s, 1H), 9.36 (br s, 2H), 8.52 (d, J=1.9 Hz, 1H), 7.80 (dd, J=8.1, 1.9 Hz, 1H), 7.68 (d, J=2.3 Hz, 1H), 7.27 (d, J=8.2 Hz, 1H), 7.04 (dd, J=8.1, 2.3 Hz, 1H), 6.88 (d, J=8.2 Hz, 1H), 4.31 (dd, J=11.9, 3.2 Hz, 1H), 3.41-3.35 (m, 1H), 3.29-3.21 (m, 1H), 2.99-2.90 (m, 1H), 2.07-1.97 (m, 1H), 1.94-1.75 (m, 3H), 1.65-1.44 (m, 2H), 1.12-1.02 (m, 2H), 0.88-0.80 (m, 1H), 0.80-0.72 (m, 1H).

Example 24: 4-cyclopropyl-3-(N-(4-fluoro-2-(piperidin-2-yl)-5-(trifluoromethyl)phenyl)sulfamoyl) benzoic Acid

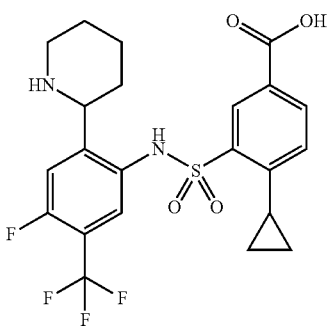 [SMILES: O=C(O)c1ccc(C2CC2)c(S(=O)(=O)Nc2cc(C(F)(F)F)c(F)cc2C2CCCCN2)c1]

Step 1: tert-butyl 6-(2-amino-5-fluoro-4-(trifluoromethyl)phenyl)-3,4-dihydropyridine-1-carboxylate: A mixture of 2-bromo-4-fluoro-5-(trifluoromethyl)aniline (224 mg, 842 μmol, 97% purity), tert-butyl 6-(4,4,5,5-tetramethyl-1,3,2-dioxaborolan-2-yl)-3,4-dihydropyridine-1-carboxylate (283 mg, 842 μmol, 92% purity), K$_3$PO$_4$(s) (360 mg, 1.70 mmol), PdCl$_2$(AmPhos)$_2$ (57 mg, 81 μmol) in dioxane (3 ml) and water (0.75 ml) was sparged with N$_2$ for 10 min, and then heated at 80° C. for 5 h. The reaction mixture was allowed to cool to RT and was filtered through Celite®, washing with EtOAc (10 ml), and the filtrate concentrated in vacuo. The crude product was purified by chromatography on silica gel (12 g cartridge, 0-30% EtOAc/isohexane) to afford the title compound (197 mg, 0.46 mmol, 55% yield, 85% purity) as an orange oil. UPLC-MS (Method 5): m/z 261.2 (M+H−Boc)$^+$, at 0.77 min.

Step 2: tert-butyl 6-(2-((2-cyclopropyl-5-(methoxycarbonyl)phenyl)sulfonamido)-5-fluoro-4-(trifluoromethyl)phenyl)-3,4-dihydropyridine-1-carboxylate: The product from Example 17 Step 4 (175 mg, 604 μmol, 95% purity) was dissolved in pyridine (2 ml) and stirred for 5 min. The product from Step 1 above (197 mg, 465 μmol, 85% purity) was added and then the resultant mixture was stirred vigorously at RT for 19 h. Additional product from Example 17 Step 4 (78 mg, 0.27 mmol, 95% purity) was added and the resultant mixture stirred at RT for 3 days. The reaction mixture was concentrated in vacuo, azeotroping with PhMe (2×6 ml). The crude product was purified by chromatography on silica gel (12 g cartridge, 0-30% EtOAc/isohexane) to afford the title compound (279 mg, 368 μmol, 79% yield, 79% purity) as an orange oil. UPLC-MS (Method 1): m/z 499.3 (M+H−Boc)$^+$, 597.1 (M−H)$^−$, at 1.99 min.

Step 3: methyl 4-cyclopropyl-3-(N-(4-fluoro-2-(piperidin-2-yl)-5-(trifluoromethyl)phenyl)sulfamoyl)benzoate: TFA (1.4 ml, 18.2 mmol) was added to a solution of the product from Step 2 above (279 mg, 368 μmol, 79% purity) in DCM (1.4 ml) at RT and stirred for 30 min. The reaction mixture was concentrated in vacuo. The residue was dissolved in THF (2.8 ml) and then Et$_3$N (77 μl, 552 μmol) and NaBH(OAc)$_3$ (237 mg, 1.12 mmol) were added. The resultant mixture was stirred at RT for 1 h. The reaction mixture was quenched with saturated NaHCO$_3$ (aq) (10 ml) until pH 8 and then EtOAc (5 ml) was added. The phases were separated and then the aqueous phase was extracted with EtOAc (3×5 ml). The organic phases were combined and washed with brine (5 ml), dried by passage through a phase separator and then concentrated in vacuo. The crude product was purified by chromatography on silica gel (12 g cartridge, 0-100% EtOAc/isohexane) to afford the title compound (147 mg, 279 μmol, 76% yield, 95% purity) as a cream solid. UPLC-MS (Method 1): m/z 501.3 (M+H)$^+$, 499.2 (M−H)$^−$, at 1.05 min. $^1$H NMR (500 MHz, DMSO-d$_6$) δ 9.24 (br s, 2H), 8.50 (d, J=1.9 Hz, 1H), 7.83 (dd, J=8.2, 2.0 Hz, 1H), 7.45 (d, J=6.8 Hz, 1H), 7.18 (d, J=11.5 Hz, 1H), 6.91 (d, J=8.2 Hz, 1H), 4.30 (dd, J=10.7, 4.4 Hz, 1H), 3.84 (s, 3H), 3.41-3.35 (m, 1H), 3.27-3.19 (m, 1H), 2.99-2.87 (m, 1H), 1.98-1.74 (m, 4H), 1.62-1.43 (m, 2H), 1.12-1.01 (m, 2H), 0.87-0.73 (m, 2H).

Example 25: 4-cyclopropyl-3-(N-(4-fluoro-5-(methylsulfonyl)-2-(piperidin-2-yl)phenyl)sulfamoyl)benzoic Acid Hydrochloride

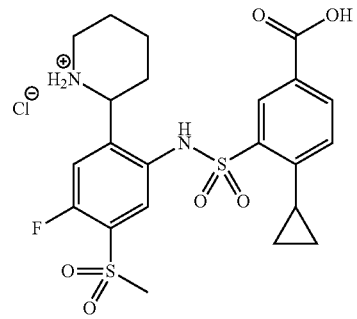

Step 1: 2-bromo-4-fluoro-5-(methylsulfonyl)aniline: Method A—Iron powder (74.9 mg, 1.34 mmol) was added to a solution of 1-bromo-5-fluoro-4-(methylsulfonyl)-2-nitrobenzene (102 mg, 335 μmol, 98% purity) in AcOH (1 ml) and EtOH (1 ml). The resultant suspension was stirred vigorously at 100° C. for 3.5 h. The reaction mixture was allowed to cool to RT, then diluted with water (5 ml), and neutralised using K$_2$CO$_3$(s). The mixture was filtered through Celite®, washing sequentially with EtOAc (10 ml) and THF (5 ml), and the filtrate concentrated in vacuo. The resultant aqueous mixture was diluted with water (5 ml) and extracted with EtOAc (3×5 ml). The organic phases were combined, dried by passage through a phase separator, and then concentrated in vacuo to afford the title compound (84 mg, 298 μmol, 89% purity, 95% purity) as a light-brown solid. $^1$H NMR (500 MHz, DMSO-d$_6$) δ 7.65 (d, J=9.5 Hz, 1H), 7.28 (d, J=6.6 Hz, 1H), 5.74 (br s, 2H), 3.26 (s, 3H).

Method B—Iron powder (142 mg, 2.54 mmol) was added to a solution of 1-bromo-5-fluoro-4-(methylsulfonyl)-2-nitrobenzene (156 mg, 513 μmol, 98% purity) and NH$_4$Cl(s) (137 mg, 2.56 mmol) in EtOH (1.2 ml) and water (240 μl). The suspension was stirred vigorously at 80° C. for 1 h. The reaction mixture was allowed to cool to RT, and then was diluted with water (3 ml) and filtered through Celite®, washing with EtOAc (10 ml). The phases were separated and then the aqueous phase was extracted with EtOAc (2×3 ml). The organic phases were combined and washed with brine (3 ml), dried over MgSO$_4$, filtered and concentrated in vacuo to afford the title compound (130 mg, 335 µmol, 65% yield, 69% purity) as a brown oil.

Step 2: tert-butyl 6-(2-amino-5-fluoro-4-(methylsulfonyl)phenyl)-3,4-dihydropyridine-1-carboxylate: A mixture of the product from Step 1 Method B above (130 mg, 335 µmol, 69% purity), tert-butyl 6-(4,4,5,5-tetramethyl-1,3,2-dioxaborolan-2-yl)-3,4-dihydropyridine-1-carboxylate (124 mg, 368 µmol, 92% purity), K$_3$PO$_4$ (142 mg, 669 µmol), PdCl$_2$(AmPhos)$_2$ (24 mg, 34 µmol) in dioxane (2.4 ml) and water (0.6 ml) was sparged with N$_2$ for 10 min, and then heated at 80° C. for 2.5 h. Additional tert-butyl 6-(4,4,5,5-tetramethyl-1,3,2-dioxaborolan-2-yl)-3,4-dihydropyridine-1-carboxylate (45 mg, 0.13 mmol, 92% purity) and PdCl$_2$(AmPhos)$_2$ (17 mg, 24 µmol) were added, and then the mixture was sparged with N$_2$ for 5 min and heated at 80° C. for 1 h. The reaction mixture was allowed to cool to RT and was filtered through Celite®, washing with EtOAc (10 ml), and concentrated in vacuo. The crude product was purified by chromatography on silica gel (12 g cartridge, 0-50% EtOAc/isohexane) to afford the title compound (87 mg, 211 µmol, 63% yield, 90% purity) as an orange oil. UPLC-MS (Method 5): m/z 271.2 (M+H−Boc)$^+$, at 0.63 min.

The above reaction was carried out using the product from Step 1 Method A above (79 mg, 280 µmol, 95% purity) to provide the title compound (87 mg, 223 µmol, 80% yield, 95% purity)

Step 3: tert-butyl 6-(2-((2-cyclopropyl-5-(methoxycarbonyl)phenyl)sulfonamido)-5-fluoro-4-(methylsulfonyl)phenyl)-3,4-dihydropyridine-1-carboxylate: The product from Example 17 Step 4 (97 mg, 335 µmol, 95% purity) was dissolved in pyridine (1 ml) and stirred for 5 min. The product from Step 2 above (87 mg, 211 µmol, 90% purity) was added and then the resultant mixture was stirred vigorously at RT for 18 h. In a separate vessel, the product from Example 17 Step 4 (77.0 mg, 266 µmol, 95% purity) was dissolved in pyridine (1 ml) and stirred for 5 min. the product from Step 2 above (87.0 mg, 223 µmol, 95% purity) was added and then the resultant mixture was stirred vigorously at RT for 5 days. Additional product from Example 17 Step 4 (33.0 mg, 114 µmol, 95% purity) was added and the resultant mixture stirred at RT for 24 h. The two reaction mixtures were combined, diluted with PhMe (6 ml) and concentrated in vacuo. The residue was dissolved in EtOAc (6 ml), washed with saturated NaHCO$_3$ (aq) (5 ml) and then the aqueous phase was extracted with EtOAc (2×6 ml). The organic phases were combined and washed with brine (6 ml), dried by passage through a phase separator and concentrated in vacuo to afford the title compound (224 mg, 0.27 mmol, 62% yield, 73% purity) as an orange foam. UPLC-MS (Method 1): m/z 509.4 (M+H−Boc)$^+$, 607.2 (M−H)$^-$, at 1.68 min.

Step 4: methyl 4-cyclopropyl-3-(N-(4-fluoro-5-(methylsulfonyl)-2-(piperidin-2-yl)phenyl)sulfamoyl)benzoate: TFA (1 ml, 13.0 mmol) was added to a solution of the product from Step 3 above (224 mg, 269 µmol, 73% purity) in DCM (1 ml) at RT and the resultant mixture was stirred for 30 min and then concentrated in vacuo. The residue was dissolved in THF (2 ml) and then treated with Et$_3$N (56 µl, 403 µmol) and NaBH(OAc)$_3$ (171 mg, 806 µmol). The resultant mixture was stirred at RT for 1.5 h. The reaction mixture was quenched with saturated NaHCO$_3$ (aq) (~8 ml) until pH 8, and then EtOAc (4 ml) was added. The phases were separated, and the aqueous phase extracted with EtOAc (3×4 ml). The organic phases were combined, washed with brine (10 ml), dried by passage through a phase separator, and then concentrated in vacuo. The crude product was partially purified by chromatography on silica gel (12 g cartridge, 0-100% EtOAc/isohexane then 5% MeOH/DCM) and then purified by chromatography on silica gel (12 g cartridge, 0-5% MeOH/DCM) to afford methyl the title compound (28 mg, 53.7 µmol, 20% yield, 98% purity) as a pale-yellow solid. UPLC-MS (Method 1): m/z 511.3 (M+H)$^+$, 509.2 (M−H)$^-$, at 0.87 min.

Step 5: 4-cyclopropyl-3-(N-(4-fluoro-5-(methylsulfonyl)-2-(piperidin-2-yl)phenyl)sulfamoyl)benzoic acid hydrochloride: 1 M LiOH(aq) (0.50 ml, 0.50 mmol) was added to a suspension of the product from Step 4 above (28 mg, 53.7 µmol, 98% purity) in THF (1 ml) at RT. The resultant mixture was stirred at RT for 19 h. The reaction mixture was concentrated in vacuo to remove THF. The residue was diluted with water (4 ml) and then washed with TBME (3 ml). The aqueous phase was acidified using 1 M HCl(aq) until pH 4-5 and then extracted with EtOAc (3×3 ml). The extracts were combined, dried by passage through a phase separator, and concentrated in vacuo. The resultant oil was dissolved in water (1 ml), filtered, washing with water (2 ml), and then the filtrate was freeze-dried to afford the title compound (7.4 mg, 13.2 µmol, 25% yield, 95% purity) as a white solid. UPLC-MS (Method 1): m/z 497.3 (M+H)$^+$, 495.2 (M−H)$^-$, at 0.74 min. $^1$H NMR (500 MHz, DMSO-d$_6$) δ 13.22 (br s, 1H), 10.59 (br s, 1H), 9.64 (br s, 1H), 9.13 (br s, 1H), 8.28 (s, 1H), 8.20-7.81 (m, 2H), 7.57-7.37 (m, 1H), 7.21-7.00 (m, 1H), 4.52-4.29 (m, 1H), 3.42-3.35 (m, 2H), 3.25 (s, 3H), 3.06-2.93 (m, 1H), 2.89-2.65 (m, 1H), 1.89-1.67 (m, 4H), 1.56-1.32 (m, 2H), 1.17-1.02 (m, 2H), 1.00-0.88 (m, 1H), 0.88-0.77 (m, 1H).

Example 26: 3-(N-(4-chloro-2-(piperidin-2-yl)-5-(trifluoromethyl)phenyl)sulfamoyl)-4-cyclopropyl-benzoic Acid

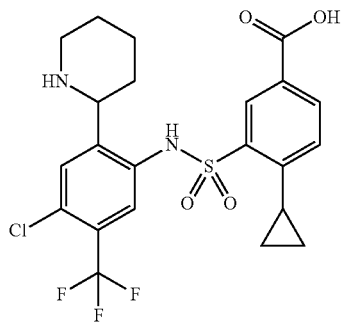 [SMILES: O=C(O)c1ccc(C2CC2)c(S(=O)(=O)Nc2cc(C(F)(F)F)c(Cl)cc2C2CCCCN2)c1]

Step 1: Methyl 3-(N-(4-chloro-2-(piperidin-2-yl)-5-(trifluoromethyl)phenyl)sulfamoyl)-4-cyclopropylbenzoate: A mixture of 4-chloro-2-iodo-5-(trifluoromethyl)aniline (250 mg, 778 µmol), tert-butyl 6-(4,4,5,5-tetramethyl-1,3,2-dioxaborolan-2-yl)-3,4-dihydropyridine-1-carboxylate (304 mg, 933 µmol, 95% purity), K$_3$PO$_4$(s) (330 mg, 1.56 mmol), PdCl$_2$(AmPhos)$_2$ (55 mg, 78 µmol) in dioxane (3.0 ml) and Water (0.75 ml) was sparged with N$_2$ for 10 min, and then heated at 80° C. for 4 h. The reaction mixture was allowed to cool to RT, and was then filtered through Celite®, washing with EtOAc (200 ml), and the filtrate concentrated in vacuo. The residue was partially purified by chromatography on silica gel (24 g cartridge, 0-50% EtOAc/isohexane) to afford a black solid (220 mg).

The product from Example 17 Step 4 (219 mg, 759 μmol, 95% purity) was dissolved in pyridine (2.0 ml) and stirred for 5 min. The black solid (220 mg) was added and then the resultant mixture was stirred vigorously at RT for 2 days. Additional product from Example 17 Step 2 (110 mg, 380 μmol, 95% purity) was dissolved in pyridine (200 μL), stirred for 5 min, then added to the reaction mixture. The resultant solution was stirred at RT for 3 days. The reaction mixture was concentrated in vacuo, azeotroping with PhMe. The residue was dissolved in DCM (10 ml) and washed with saturated NaHCO$_3$ (aq) (2×10 ml). The organic phase was passed through a phase separator, concentrated onto silica and the residue partially purified by chromatography on silica gel (12 g cartridge, 0-30% EtOAc/isohexane) to afford a brown oil (274 mg). TFA (600 μL, 7.79 mmol) was added to a solution of the brown oil (274 mg) in DCM (600 μl) at RT and the resultant mixture stirred for 30 min, and then concentrated in vacuo. The residue was dissolved in THF (1.2 ml), and then treated sequentially with Et$_3$N (100 μl, 0.72 mmol) and NaBH(OAc)$_3$ (100 mg, 472 μmol). The resultant mixture was stirred at RT for 1 h. The reaction mixture was quenched with saturated NaHCO$_3$ (aq) (20 ml) until pH 8 and then extracted with EtOAc (3×20 ml). The organic phases were combined, washed with brine (60 ml), dried by passage through a phase separator and then concentrated in vacuo. The crude product was purified by chromatography on silica gel (12 g cartridge, 0-100% EtOAc/isohexane, then 10% (0.7 M NH$_3$ in MeOH)/DCM) to afford the title compound (63 mg, 105 μmol, 13% yield, 86% purity) as a brown oil. UPLC-MS (Method 1): m/z 517.2 (M+H)$^+$, 515.2 (M−H)$^−$, at 1.18 min.

Step 2: 3-(N-(4-chloro-2-(piperidin-2-yl)-5-(trifluoromethyl)phenyl)sulfamoyl)-4-cyclopropylbenzoic acid: 1 M LiOH(aq) (420 μl, 420 μmol) was added to a suspension of the product from Step 1 above (63 mg, 105 μmol, 86% purity) in THF (840 μl) at RT. The resultant mixture was stirred at RT for 3 days. The reaction mixture was concentrated in vacuo to remove THF. The residue was diluted with water (10 ml) and then washed with EtOAc (10 ml). The aqueous phase was acidified using 1 M HCl(aq) until pH 4-5, and then extracted with EtOAc (2×10 ml), followed by 1:1 EtOAc/THF (10 ml). The extracts were combined and dried by passage through a phase separator, and then concentrated in vacuo. The crude product was purified by preparative HPLC (Waters X-Bridge BEH column C18, 5 μm 30×100 mm, 5-20% 10 mM ammonium bicarbonate(aq)/MeCN) to afford the title compound (10 mg, 18.9 μmol, 18% yield, 95% purity) as a white solid. UPLC-MS (Method 2): m/z 503.3 (M+H)$^+$, 501.1 (M−H)$^−$, at 0.69 min. $^1$H NMR (500 MHz, DMSO-d$_6$) δ 9.14 (br s, 1H), 8.50 (d, J=1.9 Hz, 1H), 7.81 (d, J=8.2, 1.9 Hz, 1H), 7.61 (s, 1H), 7.32 (s, 1H), 6.88 (d, J=8.3 Hz, 1H), 4.45-4.27 (m, 1H), 3.46-3.37 (m, 1H), 3.26-3.18 (m, 1H), 3.01-2.90 (m, 1H), 1.96-1.73 (m, 4H), 1.63-1.47 (m, 2H), 1.10-1.03 (m, 2H), 0.88-0.72 (m, 2H). Two exchangeable protons not observed.

Example 27: 3-(N-(4-chloro-5-(methylsulfonyl)-2-(piperidin-2-yl)phenyl)sulfamoyl)-4-cyclopropylbenzoic Acid Hydrochloride

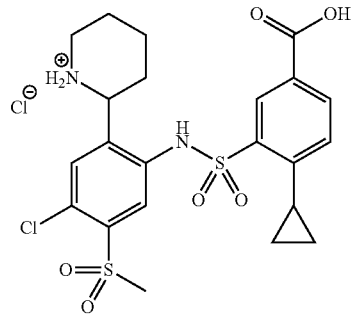 [SMILES: [Cl-] ; CS(=O)(=O)c1cc(NS(=O)(=O)c2cc(C(=O)O)ccc2C2CC2)c(C2CCCC[NH2+]2)cc1Cl]

Step 1: 1-bromo-5-chloro-4-(methylsulfonyl)-2-nitrobenzene: A stirred solution of 4-bromo-2-chloro-1-(methylsulfonyl)benzene (15 g, 55.7 mmol) in H$_2$SO$_4$ (150 ml) was treated with KNO$_3$ (16.9 g, 167 mmol) at 0° C. After 1 h, the reaction mixture was poured into ice cold water (1.5 l) and was extracted with EtOAc (2×500 ml). The extracts were combined and washed with saturated NaHCO$_3$ (aq) (1 l), dried over Na$_2$SO$_4$, and concentrated in vacuo to afford a light brown oil (25 g), which was purified by column chromatography (5-33% EtOAc/hexane), to afford the title compound (15 g, 48.1 mmol, 86% yield) as light-brown solid. $^1$H NMR (400 MHz, DMSO-d$_6$) δ 8.56 (s, 1H), 8.52 (s, 1H), 3.47 (s, 3H).

Step 2: 2-bromo-4-chloro-5-(methylsulfonyl) aniline: A stirred solution of the product from Step 1 above (7.0 g, 22.4 mmol) in EtOH (112 ml) and water (112 ml) was treated with iron powder (6.30 g, 112 mmol) and NH$_4$Cl(s) (6.0 g, 112 mmol) at RT. The resultant mixture was stirred at 80° C. for 2 h. The mixture was cooled to RT, then filtered through Celite®, washing EtOH (200 ml). The filtrate was concentrated in vacuo, and the residue suspended in water (200 ml) and extracted with EtOAc (3×100 ml). The extracts were combined and dried over Na$_2$SO$_4$(s), then concentrated in vacuo. The residue was purified by chromatography on silica gel (10-67% EtOAc/hexane) to afford the title compound (5.3 g, 18.7 mmol, 76% yield) as an off-white solid. $^1$H NMR (400 MHz, DMSO-d$_6$) δ 7.74 (s, 1H), 7.49 (s, 1H), 6.09 (1H, s 2H), 3.31 (s, 3H).

Step 3: tert-butyl 6-(2-amino-5-chloro-4-(methylsulfonyl)phenyl)-3,4-dihydropyridine-1-carboxylate: A mixture of the product from Step 2 above (200 mg, 703 μmol), tert-butyl 6-(4,4,5,5-tetramethyl-1,3,2-dioxaborolan-2-yl)-3,4-dihydropyridine-1-carboxylate (254 mg, 773 μmol, 94% purity), K$_3$PO$_4$(s) (299 mg, 1.41 mmol), PdCl$_2$(AmPhos)$_2$ (52 mg, 73 μmol) in dioxane (3 ml) and water (0.75 ml) was sparged with N$_2$ for 10 min, and then heated at 80° C. for 4 h. The reaction mixture was allowed to cool to RT, and was then filtered through Celite®, washing with EtOAc (10 ml), and the filtrate concentrated in vacuo. The crude product was purified by chromatography on silica gel (12 g cartridge, 0-45% EtOAc/isohexane) to afford the title compound (240 mg, 292 μmol, 42% yield, 47% purity) as an orange solid. UPLC-MS (Method 1): m/z 287.2 (M+H−Boc)$^+$ at 1.44 min. $^1$H NMR (500 MHz, DMSO-d$_6$) δ 7.33 (s, 1H), 7.10 (s, 1H), 5.43 (br s, 2H), 5.26 (t, J=3.7 Hz, 1H), 3.92 (s, 3H), 3.71-3.61 (m, 2H), 2.25-2.16 (m, 2H), 1.81-1.69 (m, 2H), 1.06 (s, 9H).

Step 4: tert-butyl 6-(5-chloro-2-((2-cyclopropyl-5-(methoxycarbonyl)phenyl)sulfonamido)-4-(methylsulfonyl)phenyl)-3,4-dihydropyridine-1-carboxylate: The product from Example 17 Step 4 (131 mg, 453 µmol, 95% purity) was dissolved in pyridine (2 ml) and stirred for 5 min. The product from Step 3 above (240 mg, 292 µmol, 47% purity) was added and then the resultant mixture was stirred vigorously at RT for 18 h. Additional product from Example 17 Step 4 (131 mg, 453 µmol, 95% purity) was added and stirring was continued for 31 h. A third portion of product from Example 17 Step 4 (131 mg, 453 µmol, 95% purity) was added and stirring was continued for 17 h. The reaction mixture was diluted with PhMe (15 ml) and concentrated in vacuo. The crude product was purified by chromatography on silica gel (12 g cartridge, 0-50% EtOAc/isohexane) to afford the title compound (198 mg, 257 µmol, 88% yield, 81% purity) as a yellow solid. UPLC-MS (Method 1): m/z 525.2 (M+H−Boc)+, 623.2 (M−H)−, at 1.72 min.

Step 5: methyl 3-(N-(4-chloro-5-(methylsulfonyl)-2-(piperidin-2-yl)phenyl)sulfamoyl)-4-cyclopropylbenzoate: TFA (1.00 ml, 13.0 mmol) was added to a solution of the product from Step 4 above (198 mg, 257 µmol, 81% purity) in DCM (1 ml) at RT. The resultant mixture was stirred for 30 min and then concentrated in vacuo. The residue was dissolved in THF (2 ml) and then treated with Et₃N (100 µL, 0.72 mmol) and NaBH(OAc)₃ (170 mg, 802 µmol) were added. The resultant mixture was stirred at RT for 1 h. The reaction mixture was quenched with saturated NaHCO₃ (aq) (10 ml) until pH 8, and then extracted with EtOAc (3×10 ml). The extracts were combined, washed with brine (30 ml), dried by passage through a phase separator, and then concentrated in vacuo. The crude product was purified by chromatography on silica gel (12 g cartridge, 0-100% EtOAc/isohexane followed by 10% (0.7 M NH₃ in MeOH)/DCM) to afford the title compound (43 mg, 75.9 µmol, 30% yield, 93% purity) as a yellow solid. UPLC-MS (Method 1): m/z 527.3 (M+H)+ (ES+); 525.1 (M−H)−, at 0.95 min.

Step 6: 3-(N-(4-chloro-5-(methylsulfonyl)-2-(piperidin-2-yl)phenyl)sulfamoyl)-4-cyclopropylbenzoic acid hydrochloride: 1 M LiOH(aq) (0.30 ml, 0.30 mmol) was added to a suspension of the product from Step 5 above (43 mg, 76 µmol, 93% purity) in THF (0.6 ml) at RT. The resultant mixture was stirred at RT for 3 days. The reaction mixture was concentrated in vacuo to remove THF. The residue was diluted with water (10 ml) and then washed with EtOAc (10 ml). The aqueous phase was acidified using 1 M HCl(aq) until pH 4-5, then extracted with EtOAc (2×10 ml) followed by 1:1 EtOAc/THF (10 ml). The extracts were combined and dried by passage through a phase separator, and then concentrated in vacuo to afford the title compound (12 mg, 21 µmol, 27% yield, 95% purity) as a pale yellow solid. UPLC-MS (Method 1): m/z 514.2 (M+H)+, 512.1 (M−H)−, at 0.80 min. ¹H NMR (500 MHz, DMSO-d₆) δ 13.28 (br s, 1H), 10.72 (s, 1H), 9.72-9.37 (m, 1H), 9.20-8.97 (m, 1H), 8.43-8.15 (m, 2H), 8.02 (d, J=8.2 Hz, 1H), 7.71 (s, 1H), 7.15 (d, J=8.2 Hz, 1H), 4.61-4.38 (m, 1H), 3.30 (s, 3H), 3.17-2.93 (m, 1H), 2.88-2.68 (m, 1H), 1.88-1.73 (m, 4H), 1.50-1.38 (m, 2H), 1.18-1.02 (m, 2H), 1.01-0.91 (m, 1H), 0.89-0.77 (m, 1H). One exchangeable proton not observed.

Example 28: 4-cyclopropyl-3-(N-(5-(isothiazol-5-yl)-2-(piperidin-2-yl)phenyl)sulfamoyl)benzoic Acid

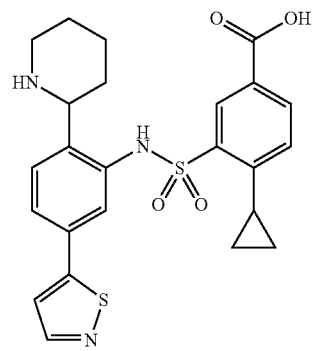 [SMILES: O=C(O)c1ccc(C2CC2)c(S(=O)(=O)Nc2cc(-c3ccns3)ccc2C2CCCCN2)c1]

Step 1: 2-nitro-4-(4,4,5,5-tetramethyl-1,3,2-dioxaborolan-2-yl)phenol: A mixture of 4-bromo-2-nitrophenol (1.00 g, 4.59 mmol), bis(pinacolato)diboron (1.28 g, 5.05 mmol), Pd(dppf)Cl₂.DCM (187 mg, 229 µmol) and KOAc (900 mg, 9.17 mmol) in dioxane (15 ml) was sparged with N₂ for 10 min. The reaction was heated at 80° C. for 2 h. The reaction mixture was allowed to cool to RT, then filtered through Celite®, washing with EtOAc (5 ml), and concentrated onto silica gel. The residue was purified by chromatography on silica gel (40 g cartridge, 0-6% EtOAc/isohexane) to afford the title compound (765 mg, 2.86 mmol, 62% yield, 99% purity) as a bright yellow solid. ¹H NMR (500 MHz, DMSO-d₆) δ 11.43 (br s, 1H), 8.07 (d, J=1.6 Hz, 1H), 7.78-7.73 (m, 1H), 7.15-7.11 (m, 1H), 1.29 (s, 12H).

Step 2: 4-(isothiazol-5-yl)-2-nitrophenol: A mixture of the product from Step 1 above (359 mg, 1.34 mmol, 99% purity), 5-iodoisothiazole (368 mg, 1.74 mmol), anhydrous K₃PO₄ (569 mg, 2.68 mmol), XPhos Pd G3 (113 mg, 134 µmol) in dioxane (5 ml) and water (1.25 ml) was sparged with N₂ for 10 min before being heated at 80° C. for 1.5 h. The reaction mixture was allowed to cool to RT, then filtered through Celite® and washed with EtOAc (15 ml). NH₄Cl (aq) (15 ml) was added to the filtrate and the layers were separated. The organic phase was washed with NH₄Cl(aq) (15 ml) and then the aqueous phases were combined and extracted with EtOAc (10 ml). The combined organic phase was dried over MgSO₄, filtered, and concentrated in vacuo to afford a light tan solid (445 mg), which was used in the next step without purification.

Step 3: 4-(isothiazol-5-yl)-2-nitrophenyl trifluoromethanesulfonate: A mixture of the product from Step 2 above (445 mg), bis(trifluoromethanesulfonyl)aniline (622 mg, 1.74 mmol) and Et₃N (486 µl, 3.48 mmol) in DCM (20 ml) was stirred at RT for 18 h. The reaction mixture was concentrated in vacuo and purified by chromatography on silica gel (12 g cartridge, 0-40% EtOAc/isohexane) to afford the title compound (337 mg, 761 µmol, 57% yield over 2 steps, 80% purity) as a dark yellow-brown oil. ¹H NMR (500 MHz, Chloroform-d) δ 8.57 (d, J=1.8 Hz, 1H), 8.37 (d, J=2.3 Hz, 1H), 7.93 (dd, J=8.6, 2.3 Hz, 1H), 7.56 (d, J=8.6 Hz, 1H), 7.52 (d, J=1.8 Hz, 1H).

Step 4: tert-butyl 6-(4-(isothiazol-5-yl)-2-nitrophenyl)-3,4-dihydropyridine-1-carboxylate: A mixture of the product from Step 3 above (261 mg, 589 µmol, 80% purity), tert-butyl 6-(4,4,5,5-tetramethyl-1,3,2-dioxaborolan-2-yl)-3,4-dihydropyridine-1-carboxylate (175 mg, 532 µmol, 94% purity), anhydrous K₃PO₄ (227 mg, 1.07 mmol), PdCl₂

(AmPhos)₂ (39 mg, 55.1 µmol) in dioxane (2.5 ml) and water (625 µl) was sparged with N₂ for 10 min before being heated at 80° C. for 2 h. The reaction mixture was allowed to cool to RT, then filtered through Celite®, washing with EtOAc (15 ml) and concentrated in vacuo. The residue was purified by chromatography on silica gel (24 g cartridge, 0-20% EtOAc/isohexane) to afford the title compound (50.3 mg, 104 µmol, 20% yield, 80% purity) as an orange oil. ¹H NMR (500 MHz, Chloroform-d) δ 8.53-8.50 (m, 1H), 7.96 (d, J=1.9 Hz, 1H), 7.75 (dd, J=8.0, 1.9 Hz, 1H), 7.51 (d, J=8.0 Hz, 1H), 7.48-7.45 (m, 1H), 5.41 (t, J=3.9 Hz, 1H), 3.69-3.61 (m, 2H), 2.33 (td, J=6.7, 3.9 Hz, 2H), 1.93-1.86 (m, 2H), 1.22-1.06 (m, 9H).

Step 5: tert-butyl 6-(2-amino-4-(isothiazol-5-yl)phenyl)-3,4-dihydropyridine-1-carboxylate: Two reactions were carried out on a 50.3 mg and a 9.6 mg scale respectively and combined for work-up and purification. Zinc (67.9 mg, 1.04 mmol) and ammonium chloride (55.6 mg, 1.04 mmol) were added to a solution of the product from Step 4 above (50.3 mg, 104 µmol, 80% purity) in THF (0.75 ml) and water (0.25 ml). The suspension was stirred vigorously at RT for 24 h. The reaction mixtures were combined, filtered through Celite®, washed with EtOAc (5 ml), and concentrated in vacuo to afford a yellow glass (66.3 mg), which was used in the next step without purification. UPLC-MS (Method 1): m/z 258.3 (M+H−Boc)⁺ at 1.63 min.

Step 6: tert-butyl 6-(2-((2-cyclopropyl-5-(methoxycarbonyl)phenyl)sulfonamido)-4-(isothiazol-5-yl)phenyl)-3,4-dihydropyridine-1-carboxylate: The product from Step 5 above (66.3 mg) was added to a solution of the product from Example 17 Step 4 (72.9 mg, 252 µmol, 95% purity, 2 equiv) in pyridine (1 ml) which had been pre-mixed for 5 min. The resultant mixture was stirred at RT for 5 days. Additional the product from Example 17 Step 4 (72.9 mg, 252 µmol, 95% purity) was added and stirred at RT. Further additions of the sulfonyl chloride were made after intervals of 22 h, 3 h and 18 h (total added=10 equiv). The reaction mixture was concentrated in vacuo. The residue was purified by chromatography on silica gel (12 g cartridge, 0-50% then 100% EtOAc/isohexane) to afford the title compound in two fractions. Fraction 1 (31.0 mg, 39.0 µmol, 31% yield over 2 steps, 75% purity) as a yellow glass and Fraction 2 (50.0 mg, 23.5 µmol, 19% yield over 2 steps, 28% purity) as a yellow oil. UPLC-MS (Method 1): m/z 496.4 (M+H−Boc)⁺, 594.3 (M−H)⁻, at 1.93 min.

Step 7: methyl 4-cyclopropyl-3-(N-(5-(isothiazol-5-yl)-2-(piperidin-2-yl)phenyl)sulfamoyl)benzoate: Two reactions were carried out using the product from Step 6 above Fraction 1 (30.7 mg, 38.7 µmol, 75% purity) and Fraction 2 (50.0 mg, 23.5 µmol, 28% purity) respectively and combined for work up and purification. TFA (0.15 ml, 1.9 mmol) was added to a solution of the product from Step 6 above Fraction 1 (30.7 mg, 38.7 µmol, 75% purity) in DCM (0.15 ml) at RT and the resultant mixture stirred for 1 h, then concentrated in vacuo. The residue was dissolved in THF (0.30 ml) and then Et₃N (8.10 µl, 58.1 µmol) and NaBH(OAc)₃ (24.6 mg, 116 µmol) were added. The resultant mixture was stirred at RT for 1 h, then combined with the corresponding reaction set up using Fraction 2, quenched with saturated NaHCO₃ (aq) (4 ml) to pH 8. EtOAc (3 ml) was added, the phases were separated, and the aqueous phase was extracted with EtOAc (3×5 ml). The organic phases were combined and concentrated onto silica gel, then purified by chromatography on silica gel (4 g cartridge, 0-10% MeOH/DCM) to afford the title compound (19.7 mg, 37.6 µmol, 61% yield, 95% purity) as a yellow solid. UPLC-MS (Method 1): m/z 498.4 (M+H)⁺, 496.2 (M−H)⁻, at 0.96 min.

Step 8: 4-cyclopropyl-3-(N-(5-(isothiazol-5-yl)-2-(piperidin-2-yl)phenyl)sulfamoyl)benzoic acid: 1 M LiOH(aq) (154 µl, 154 µmol) was added to a suspension of the product from Step 7 above (19.7 mg, 37.6 µmol, 95% purity) in THF (308 µl) at RT. The resultant mixture was stirred at RT for 18 h. The mixture was concentrated in vacuo to remove the THF. The residue was diluted with water (2 ml) and then washed with TBME (1 ml). The aqueous phase was acidified using 1 M HCl(aq) until pH 4-5 and then extracted with EtOAc (4×2 ml) was added. The organic phases were combined, dried over MgSO₄, filtered, and concentrated in vacuo. The residue was purified by preparative HPLC (Waters, Acidic (0.1% Formic acid), Acidic, Waters X-Select Prep-C18, 5 µm, 19×50 mm column, 17-47% MeCN in Water) to afford the title compound (7.8 mg, 15.2 µmol, 40% yield, 94% purity) as an off-white solid. UPLC-MS (Method 1): m/z 484.3 (M+H)⁺, 482.3 (M−H)⁻, at 0.84 min. ¹H NMR (500 MHz, DMSO-d₆) δ 9.52 (br s, 1H), 8.65 (d, J=1.9 Hz, 1H), 8.50 (d, J=1.8 Hz, 1H), 7.82 (dd, J=8.1, 1.9 Hz, 1H), 7.51 (d, J=1.8 Hz, 1H), 7.43 (d, J=1.9 Hz, 1H), 7.15 (d, J=7.9 Hz, 1H), 6.97 (dd, J=7.8, 1.9 Hz, 1H), 6.88 (d, J=8.2 Hz, 1H), 4.28-4.19 (m, 1H), 3.41-3.35 (m, 1H), 3.28-3.20 (m, 1H), 2.98-2.88 (m, 1H), 2.11-2.00 (m, 1H), 1.93-1.77 (m, 3H), 1.65-1.47 (m, 2H), 1.12-1.02 (m, 2H), 0.87-0.73 (m, 2H).

Example 29: 4-cyclopropyl-3-(N-(2-(piperidin-2-yl)-5-(trifluoromethyl)phenyl)sulfamoyl)benzoic Acid Enantiomer 1

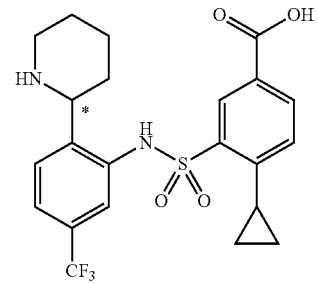 [SMILES: O=C(O)c1ccc(C2CC2)c(S(=O)(=O)Nc2cc(C(F)(F)F)ccc2C2CCCCN2)c1]

Step 1: tert-butyl 6-(2-amino-4-(trifluoromethyl)phenyl)-3,4-dihydropyridine-1-carboxylate: A mixture of 2-bromo-5-(trifluoromethyl)aniline (971 mg, 4.05 mmol), tert-butyl 6-(4,4,5,5-tetramethyl-1,3,2-dioxaborolan-2-yl)-3,4-dihydropyridine-1-carboxylate (1.49 g, 4.49 mmol) and anhydrous K₃PO₄ (1.72 g, 8.10 mmol) in dioxane (16 ml) and water (4 ml) was sparged with N₂ for 10 min. PdCl₂(AmPhos)₂ (287 mg, 405 µmol) was added and the reaction mixture sparged again with N₂ for 10 min. The resultant mixture was heated at 80° C. for 18 h. The reaction mixture was allowed to cool to RT, then filtered through Celite®, washed with EtOAc (10 ml), and concentrated in vacuo. The residue was partially purified by chromatography on silica gel (24 g cartridge, 0-15% (3:1 EtOAc/EtOH)/isohexane) and then purified by chromatography on silica gel (24 g cartridge, 10-15% EtOAc/isohexane) to afford the title compound (1.04 g, 2.46 mmol, 55% yield, 81% purity) as an orange solid. UPLC-MS (Method 1): m/z 243.3 (M+H−Boc)⁺ at 1.79 min.

Step 2: tert-butyl 6-(2-((2-cyclopropyl-5-(methoxycarbonyl)phenyl)sulfonamido)-4-(trifluoromethyl)phenyl)-3,4-dihydropyridine-1-carboxylate: Two reactions were carried out on a 58 mg and 981 mg scale respectively and combined for work-up and purification. The product from Example 17 Step 4 (805 mg, 2.79 mmol, 95% purity) was dissolved in pyridine (4 ml) at 20° C. and stirred for 5 min. The product from Step 1 above (981 mg, 2.32 mmol, 81% purity) was added and the resultant mixture was stirred vigorously at 20° C. for 90 min. Additional premixed product from Example 17 Step 4 (555 mg, 1.92 mmol, 95% purity) and pyridine (1 ml) was added and the resultant mixture stirred at 20° C. for 18 h. The reaction mixtures were combined, concentrated in vacuo, azeotroping with PhMe (2×20 ml). The residue was diluted with EtOAc (30 ml), washed with sat. NaHCO$_3$ (aq) (3×20 ml) and then the aqueous phases were combined and extracted with EtOAc (10 ml). The organic phases were combined and dried over MgSO$_4$, filtered, and concentrated in vacuo to afford the title compound (1.72 g, 1.75 mmol, 71% yield, 59% purity) as an orange oil. This material was used in the next step without purification. UPLC-MS (Method 1): m/z 481.4 (M+H–Boc)$^+$, 579.3 (M–H)$^-$, at 2.00 min.

Step 3: methyl 4-cyclopropyl-3-(N-(2-(piperidin-2-yl)-5-(trifluoromethyl)phenyl)sulfamoyl)benzoate: TFA (5 ml, 64.9 mmol) was added to a solution of the product from Step 2 above (1.72 g, 1.75 mmol, 59% purity) in DCM (5.00 ml) at RT and the resultant mixture stirred for 1 h. The mixture was concentrated in vacuo, then dissolved in THF (10 ml). Et$_3$N (0.36 ml, 2.63 mmol) and NaBH(OAc)$_3$ (1.11 g, 5.25 mmol) were added. The resultant mixture was stirred at RT for 1 h. The reaction was quenched with saturated NaHCO$_3$ (aq) (30 ml) to pH 8 and left to stand over the weekend. The resultant mixture was extracted with EtOAc (4×15 ml). The organic phases were combined and washed with brine (50 ml), dried over MgSO$_4$, filtered, and concentrated in vacuo onto silica. Purification by chromatography on silica gel (80 g cartridge, 0-3% MeOH/DCM) afforded the title compound (607 mg, 1.26 mmol, 72% yield) as a cream solid. UPLC-MS (Method 1): m/z 483.4 (M+H)$^+$, 481.2 (M–H)$^-$, at 1.04 min.

Step 4: methyl 4-cyclopropyl-3-(N-(2-(piperidin-2-yl)-5-(trifluoromethyl)phenyl)sulfamoyl)benzoate Enantiomer 1: The product from Step 3 above (50 mg, 104 µmol) was dissolved in 1:1 DCM:MeOH (1 ml) with sonication, and was then filtered and separated by chiral SFC (Waters prep 15 with UV detection by DAD at 210-400 nm, 40° C., 120 bar, ChiralPAK IC 10×250 mm, 5 µm column, flow rate 15 ml/min, 20% (0.07 M NH$_3$/EtOH)/CO$_2$)). The clean fractions were pooled, rinsed with MeOH, then concentrated in vacuo to afford the title compound (18 mg, 37 µmol, 36% yield, 99% purity) as a white solid. SFC (Waters UPC$^2$, ChiralPak IC, 4.6×250 mm column, flow rate 4 ml/min eluting with 20% (0.07 M NH$_3$/EtOH)/CO$_2$) t$_R$ 1.88 min. UPLC-MS (Method 1): m/z 483.2 (M+H)$^+$, 481.4 (M–H)$^-$, at 1.06 min.

Step 5: 4-cyclopropyl-3-(N-(2-(piperidin-2-yl)-5-(trifluoromethyl)phenyl)sulfamoyl)benzoic acid Enantiomer 1:1 M LiOH(aq) (150 µl, 150 µmol) was added to a suspension of the product from Step 4 above (18 mg, 37 µmol, 99% purity) in THF (300 µl). The resultant solutions were stirred at RT overnight. The reaction mixture was concentrated in vacuo to remove the THF. The residue was purified by chromatography (24 g reverse phase C18 cartridge, 5-40% MeCN/10 mM ammonium bicarbonate(aq) to afford the title compound (7 mg, 14 µmol, 38% yield, 95% purity) as a white solid. UPLC-MS (Method 1): m/z 469.4 (M+H)$^+$, 467.2 (M–H)$^-$, at 0.89 min. $^1$H NMR (500 MHz, Methanol-d$_4$) δ 8.55 (d, J=1.8 Hz, 1H), 8.46 (s, 1H), 8.02 (dd, J=8.2, 1.8 Hz, 1H), 7.43 (d, J=8.0 Hz, 1H), 7.41-7.37 (m, 1H), 7.19 (d, J=8.0 Hz, 1H), 7.01 (d, J=8.2 Hz, 1H), 4.49 (dd, J=12.2, 2.9 Hz, 1H), 3.56-3.46 (m, 1H), 3.15 (td, J=12.7, 3.1 Hz, 1H), 3.10-3.03 (m, 1H), 2.29-2.13 (m, 1H), 2.05-1.93 (m, 3H), 1.86-1.67 (m, 2H), 1.19-1.09 (m, 2H), 0.99-0.82 (m, 2H). Two exchangeable protons not observed.

Example 30: 4-cyclopropyl-3-(N-(2-(piperidin-2-yl)-5-(trifluoromethyl)phenyl)sulfamoyl)benzoic Acid Enantiomer 2

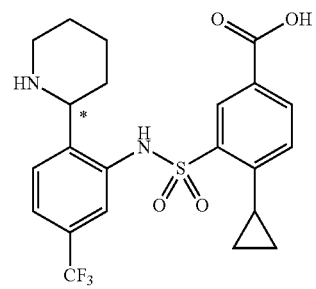 [SMILES: O=C(O)c1ccc(C2CC2)c(S(=O)(=O)Nc2cc(C(F)(F)F)ccc2C2CCCCN2)c1]

The title compound (8 mg, 17 µmol, 45% yield, 98% purity) was obtained as a white solid from the chiral separation performed in Example 29 Step 4, followed by hydrolysis using the procedure outlined in Example 29 Step 5. methyl 4-cyclopropyl-3-(N-(2-(piperidin-2-yl)-5-(trifluoromethyl)phenyl)sulfamoyl)benzoate Enantiomer 2 was isolated as a white solid (18 mg, 37 µmol, 36% yield, 99% purity). SFC (Waters UPC$^2$, ChiralPak IC, 4.6×250 mm column, flow rate 4 ml/min eluting with 20% (0.07 M NH$_3$/EtOH)/CO$_2$) t$_R$ 2.19 min. Other analytical data consistent with Example 29.

Example 31: 4-cyclopropyl-3-fluoro-5-(N-(2-(piperidin-2-yl)-5-(trifluoromethyl)phenyl)sulfamoyl) benzoic Acid

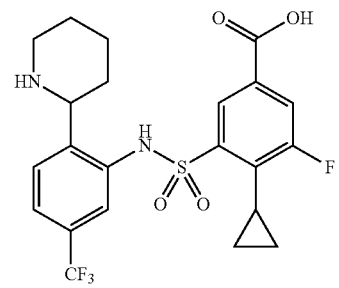 [SMILES: O=C(O)c1cc(F)c(C2CC2)c(S(=O)(=O)Nc2cc(C(F)(F)F)ccc2C2CCCCN2)c1]

Step 1: tert-butyl 6-(2-((2-bromo-3-fluoro-5-(methoxycarbonyl)phenyl)sulfonamido)-4-(trifluoromethyl)phenyl)-3,4-dihydropyridine-1-carboxylate: methyl 4-bromo-3-(chlorosulfonyl)-5-fluorobenzoate (360 mg, 1.09 mmol) was dissolved in pyridine (2 ml) and stirred for 5 min. The product from Example 29 Step 1 (340 mg, 894 µmol, 90% purity) was added and the resultant mixture was stirred vigorously at RT overnight. The reaction mixture was heated at 35° C. for 24 h, then at 60° C. for another 24 h. The reaction mixture was concentrated in vacuo, azeotroping with PhMe (2×10 ml). The residue was diluted with EtOAc (30 ml) and washed with saturated NaHCO$_3$ (aq) (2×20 ml). The organic phase was dried over MgSO$_4$, filtered, and concentrated in vacuo onto silica. Partial purification by chromatography on silica gel (24 g cartridge, 0-50% EtOAc/isohexane) followed by purification by chromatography (24 g reverse phase C18 cartridge, 15-100% (0.1% formic acid in MeCN)/(0.1% formic acid(aq))) afforded the title compound (222 mg, 0.31 mmol, 34% yield, 88% purity) as a pale yellow oil. UPLC-MS (Method 1): m/z 537.6 (M+H−Boc)$^+$, 535.5 (M−H−Boc)$^-$, at 2.02 min. $^1$H NMR (500 MHz, DMSO-d$_6$) δ 10.01 (s, 1H), 8.36-8.25 (m, 1H), 8.12-8.07 (m, 1H), 7.54-7.48 (m, 1H), 7.38-7.33 (m, 1H), 7.31-7.27 (m, 1H), 5.07 (t, J=3.7 Hz, 1H), 3.88 (s, 3H), 3.64-3.55 (m, 2H), 2.16-2.09 (m, 2H), 1.81-1.65 (m, 2H), 0.99 (s, 9H).

Step 2: tert-butyl 6-(2-((2-cyclopropyl-3-fluoro-5-(methoxycarbonyl)phenyl)sulfonamido)-4-(trifluoromethyl)phenyl)-3,4-dihydropyridine-1-carboxylate: A rigorously dried flask was charged with magnesium turnings (110 mg, 4.52 mmol) and iodine (8 mg, 0.03 mmol). An aliquot (0.5 ml) of a solution of bromocyclopropane (250 μl, 3.12 mmol) in THF (2.8 ml) was added and the mixture was heated to reflux with a heat gun. Once the brown colour disappeared the remaining solution was added at a rate that reflux was maintained. Upon complete addition the mixture was stirred at RT for 30 min. The mixture was slowly added to zinc chloride (1.9 M solution in 2-methyltetrahydrofuran) (2.40 ml, 4.56 mmol) at 0° C. The resultant mixture was then warmed to RT and stirred for 20 min. The resultant mixture was then treated with a solution of the product from Step 1 above (222 mg, 306 μmol, 88% purity) in THF (2 ml). Pd(dppf)Cl$_2$.DCM (46 mg, 56 μmol) was added and the mixture heated at 70° C. for 45 min. The mixture was allowed to cool to RT, then quenched with saturated NH$_4$Cl (aq) (10 ml) and extracted with EtOAc (2×20 ml). The extracts were combined, washed with brine (40 ml), dried over MgSO$_4$, filtered, and concentrated in vacuo to afford the title compound (250 mg, 0.30 mmol, 99% yield, 73% purity) as a dark brown oil, which was used in the next step without purification. UPLC-MS (Method 1): m/z 499.4 (M+H−Boc)$^+$, 597.3 (M−H)$^-$, at 2.08 min.

Step 3: methyl 4-cyclopropyl-3-fluoro-5-(N-(2-(piperidin-2-yl)-5-(trifluoromethyl)phenyl)sulfamoyl)benzoate: TFA (900 μl, 11.7 mmol) was added to a solution of the product from Step 2 above (250 mg, 305 μmol, 73% purity) in DCM (900 μl) at RT and the resultant mixture stirred for 1 h, then concentrated in vacuo. The residue was dissolved in THF (1.8 ml), then treated with Et$_3$N (70 μl, 0.50 mmol) and NaBH(OAc)$_3$ (200 mg, 944 μmol). The resultant mixture was stirred at RT for 2 h. Additional NaBH(OAc)$_3$ (100 mg, 472 μmol) was added and the mixture was stirred at RT for 3 h. The reaction was quenched with saturated NaHCO$_3$ (aq) (10 ml) to pH 8 and allowed to stand overnight. The resultant mixture extracted with DCM (2×10 ml). The organic phases were combined, washed with brine (20 ml), dried over MgSO$_4$, filtered, and concentrated in vacuo. The residue was partially purified by chromatography on silica gel (12 g cartridge, 0-3% MeOH/DCM) to afford a dark brown oil, which partially solidified on standing (47 mg). Unreacted starting material (0.1 g) was also recovered in the partial purification. This was resubjected to the same reaction and purification conditions to provide a dark brown solid (24 mg). A portion of the dark brown oil (27 mg) and the dark brown solid (24 mg) were separately further purified by preparative HPLC (Waters X-Select CSH C18 ODB prep column, 130A, 5 μm, 30 mm×100 mm, 20-50% MeCN/(0.1% formic acid(aq))) to afford the title compound Batch 1 (6.0 mg, 12 μmol, 6% overall yield, 96% purity) and the title compound Batch 2 (11 mg, 22 μmol, 7% overall yield, 98% purity) respectively as white solids. UPLC-MS (Method 1): m/z 501.3 (M+H)$^+$, 499.2 (M−H)$^-$, at 1.11 min.

Step 4: 4-cyclopropyl-3-fluoro-5-(N-(2-(piperidin-2-yl)-5-(trifluoromethyl)phenyl)sulfamoyl)benzoic acid: Two reactions were carried out on a 6 mg and 11 mg scale respectively and combined for work-up. 1 M LiOH(aq) (100 μl, 100 μmol) was added to a suspension of the product from Step 3 Batch 2 above (11 mg, 22 μmol, 98% purity) in THF (200 μl). The resultant mixture was stirred at RT overnight. The reaction mixtures were combined then concentrated in vacuo to remove the THF. 1 M HCl(aq) was added dropwise until pH 7 and the resultant precipitate was collected by filtration to afford the title compound (10 mg, 20 μmol, 59% yield, 95% purity) as a white solid. UPLC-MS (Method 2): m/z 487.3 (M+H)$^+$, 485.3 (M−H)$^-$, at 0.83 min. $^1$H NMR (500 MHz, Methanol-d$_4$) δ 8.38 (d, J=1.7 Hz, 1H), 7.75 (dd, J=12.9, 1.8 Hz, 1H), 7.57 (d, J=8.1 Hz, 1H), 7.39 (d, J=8.1 Hz, 1H), 7.32-7.28 (m, 1H), 4.65 (dd, J=12.0, 3.2 Hz, 1H), 3.61-3.48 (m, 1H), 3.25-3.14 (m, 1H), 2.89-2.75 (m, 1H), 2.23-1.94 (m, 4H), 1.93-1.68 (m, 2H), 1.49-1.29 (m, 2H), 1.08 (dq, J=9.0, 2.5 Hz, 2H). Three exchangeable protons not observed.

Biological Investigations

The following assays can be used to illustrate the commercial utilities of the compounds according to the present invention.

Biological Assay 1: ERAP1 Mediated Hydrolysis of an Amide Substrate Measured in a Biochemical System Materials and Solutions 1× Assay buffer (AB): 25 mM Bis-tris propane, 0.05% w/v Hydroxypropylmethylcellulose pH 7.75 made with Optima grade water Decapeptide WRVYEKC(Dnp)ALK-acid (where Dnp is Dinitrophenyl maleimide) (10-mer)

L-Leucine 7-amido-4-methylcoumarin (L-AMC)

Purified ERAP1(37-941)-10 His (ERAP1)

Assay Procedure:

12.5 μL ERAP1 enzyme in 1×AB was combined with 250 nL test compound in DMSO. 12.5 μL of either 240 μM L-AMC in 1×AB or 100 μM 10-mer in 1×AB was added to the reaction and incubated at 23° C. for 1 h. For detection, plates were read at excitation 365 nm and emission 442 nm (L-AMC) or excitation 279 nm and emission 355 nm (10-mer). Compound IC$_{50}$ was determined using a 4-parameter equation. The results for selected compounds according to the invention are shown in Table 1.

OVA Antigen Presentation Assay

The cellular effect of representative compounds according to the invention on antigen presentation can be measured by assessing their effect on the presentation of an ovalbumin-specific peptide (SIINFEKL) to T-cells, as previously described [Reeves et al, (2014) *Proc. Natl. Acad. Sci. USA* 111; 17594-17599]. Briefly, SiHa cells are transiently transfected with plasmids encoding mouse H2Kb and an ER-targeted N-terminally extended precursor peptide derived from ovalbumin (MRYMILGLLALAAVCSAAIVMKSIIN-FEHL) using Lipofectamine 3000. The cells are harvested 6 h post-transfection and transfected SiHa cells are plated compounds across a 12-point concentration response curve to quantify ERAP1 inhibitor $IC_{50}$. SiHa cells are cultured in the presence of compound for 48 h. Subsequently, B3Z cells [Karttunen et al, (1992) *Proc. Natl. Acad. Sci. USA* 89; 6020-6024] are added to the cell culture for 4 h; the B3Z T-cell hybridoma encodes a TCR recognizing specifically the SIINFEHL/H2Kb complex at the cell surface, which upon activation, triggers a signalling cascade leading to the transcription of the LacZ gene that is under the control of the IL-2 promoter. Intracellular β-galactosidase activity as a readout of T-cell activation is measured by quantifying the conversion of chlorophenored-β-D-galacto-pyranoside (CPRG) to chlorophenol red by measuring absorbance at 570 nm.

Immunopeptidomics

The effect of representative compounds according to the invention on global antigen processing can be determined using an unbiased proteomics pipeline as described by Purcell and colleagues [Purcell et al, (2019) Nat Protoc. 14; 1687-1707]. Briefly, 500 million SiHa cells are treated with compound for 24 h or siRNA for 72 hours and then harvested, lysed and MHC-bound peptides isolated by immunoaffinity capture. The peptides are eluted using 10% (v/v) acetic acid and separated from the MHC-1 and β2-microglobulin proteins by HPLC before analysis by LC-MS/MS.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

TABLE 1

Activity of selected compounds according to the invention

| | |
|---|---|
| 1 | Low |
| 2 | Medium |
| 3 | High |
| 4 | High |
| 5 | Medium |
| 6 | Medium |
| 7 | High |
| 8 | High |
| 9 | High |
| 10 | High |
| 11 | High |
| 12 | High |
| 13 | High |
| 14 | High |
| 15 | High |
| 16 | High |
| 17 | High |
| 18 | High |

TABLE 1-continued

Activity of selected compounds according to the invention

| | |
|---|---|
| 19 | High |
| 20 | High |
| 21 | High |
| 22 | High |
| 23 | High |
| 24 | High |
| 25 | High |
| 26 | High |
| 27 | High |
| 28 | High |
| 29 | High |
| 30 | High |
| 31 | High |

$IC_{50}$ vs Decapeptide WRVYEKC(Dnp)ALK-acid (where Dnp is Dinitrophenyl maleimide) (10-mer); High (<100 nM), Medium (100 nM to 500 nM), Low (>500 nM).

REFERENCES

1. Serwold et al, (2002), ERAAP customizes peptides for MHC class I molecules in the endoplasmic reticulum; Nature: 419, p 480.
2. Snyder et al, (2014), Genetic Basis for Clinical Response to CTLA-4 Blockade in Melanoma; NEJM: 371, p 2189.
3. Van Allen et al, (2015), Genomic correlates of response to CTLA-4 blockade in metastatic melanoma; Science: 348, p 124.
4. James et al, (2013), Induction of Protective Antitumor Immunity through Attenuation of ERAAP Function; J Immunol: 190, p 5839.
5. Niranjana et al, (2016), ERAAP Shapes the Peptidome Associated with Classical and Nonclassical MHC Class I Molecules; J Immunol: 197, p 1035.
6. Pepelyayeva et al, (2018), ERAP1 deficient mice have reduced Type 1 regulatory T cells and develop skeletal and intestinal features of Ankylosing Spondylitis; Sci. Reports: 8: p 12464.
7. Cifaldi et al, (2015), ERAP1 Regulates Natural Killer Cell Function by Controlling the Engagement of Inhibitory Receptors, Cancer Res.: 75, p 824.
8. Steinbach et al, (2017), ERAP1 overexpression in HPV-induced malignancies: A possible novel immune evasion mechanism, Oncoimmunol: 6, e1336594.
9. Kim et al, (2011), Human cytomegalovirus microRNA miR-US4-1 inhibits CD8+ T cell responses by targeting the aminopeptidase ERAP1, Nat. Immunol.: 12, p 984.
10. Tenzer et al, (2009), Antigen processing influences HIV-specific cytotoxic T lymphocyte immunodominance, Nat. Immunol.: 10, p 636.
11. Reeves et al, (2018), The role of polymorphic ERAP1 in autoinflammatory disease, Biosci. Rep.: 29, p 38.
12. Chen et al, (2014), Silencing or inhibition of endoplasmic reticulum aminopeptidase 1 (ERAP1) suppresses free heavy chain expression and Th17 responses in ankylosing spondylitis, Ann Rheum Dis: 75, p 916.
13. Sheehan, N J (January 2004). "The ramifications of HLA-B27". *Journal of the Royal Society of Medicine*. 97 (1): 10-4.
14. Smith, J A (January 2015). "Update on ankylosing spondylitis: current concepts in pathogenesis". *Current allergy and asthma reports*. 15 (1): 489.

15. Kuiper J J W, Mutis T, de Jager W, de Groot-Mijnes J D, Rothova A (2011). "Intraocular interleukin-17 and proinflammatory cytokines in HLA-A29-associated birdshot chorioretinopathy". *Am J Ophthalmol.* 152 (2): 177-182
16. Kuiper J J W, Emmelot M E, Rothova A, Mutis T (2013). "Interleukin-17 production and T helper 17 cells in peripheral blood mononuclear cells in response to ocular lysate in patients with birdshot chorioretinopathy". *Mol Vis.* 19: 2606-14
17. Kuiper J J W, van Setten J, Ripke S, Van't Slot R, Mulder F, Missotten T, Baarsma G S, Francioli L C, Pulit S L, de Kovel C G, Ten Dam-van Loon N, den Hollander A I, Huis In Het Veld P, Hoyng C B, Cordero-Coma M, Martin J, Llorenç V, Arya B, Thomas D, Bakker S C, Ophoff R A, Rothova A, de Bakker P I, Mutis T, Koeleman B P (2014). "A genome-wide association study identifies a functional ERAP2 haplotype associated with birdshot chorioretinopathy". *Hum Mol Genet.* 23 (22): 6081-6087
18. Evans et al (2011), Interaction between ERAP1 and HLA-B27 in ankylosing spondylitis implicates peptide handling in the mechanism for HLA-B27 in disease susceptibility. Nat Genet. 10; 43(8):761-7
19. Conde-Jaldon et al (2014), Epistatic interaction of ERAP1 and HLA-B in Behçet disease: a replication study in the Spanish population. PLoS One. 14; 9 (7)
20. Kuiper et al (2018), Functionally distinct ERAP1 and ERAP2 are a hallmark of HLA-A29-(Birdshot) Uveitis. Hum Mol Genet. doi: 10.1093/hmg/ddy319
21. Strange et al (2010), A genome-wide association study identifies new psoriasis susceptibility loci and an interaction between HLA-C and ERAP1. Nat Genet.; 42(11): 985-90.

The invention claimed is:
1. A compound of formula (I), or a pharmaceutically acceptable salt or hydrate thereof,

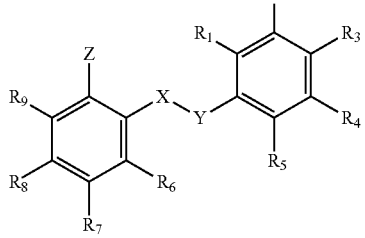

(1)

wherein:
Z is a group of formula:

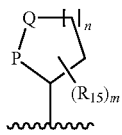

wherein P and Q are each independently $CR_{12}R_{13}$; or one of P and Q is $NR_{14}$ and the other is $CR_{12}R_{13}$;
the group X—Y is —NHSO$_2$— or —SO$_2$NH—;
$R_1$ is H, CN or alkyl;
$R_2$ is selected from COOH and a tetrazolyl group;
$R_3$ is selected from H, Cl and alkyl;
$R_4$ is selected from H and halo;
$R_5$ is selected from H, alkyl, haloalkyl, SO$_2$-alkyl, Cl, alkoxy, OH, CN, hydroxyalkyl, alkylthio, heteroaryl, cycloalkyl, heterocycloalkyl and haloalkoxy;
$R_6$ is H;
$R_7$ is selected from H, CN, haloalkyl, halo, SO$_2$-alkyl, heteroaryl, SO$_2$NR$_{16}$R$_{17}$, CONR$_{10}$R$_{11}$ and alkyl, wherein said heteroaryl group is optionally substituted by one or more substituents selected from alkyl, halo, alkoxy, CN, haloalkyl and OH;
$R_8$ is selected from H, alkyl, haloalkyl and halo;
$R_9$ is H or halo; and
$R_{10}$, $R_{11}$, $R_{12}$, $R_{13}$, $R_{14}$, $R_{16}$ and $R_{17}$ are each independently H or alkyl;
$R_{15}$ is selected from alkyl, halo, alkoxy, CN, haloalkyl and OH; and
m and n are each independently 0, 1, 2 or 3.

2. The compound of formula (I) according to claim 1 wherein n is 1 or 2.

3. The compound of formula (I) according to claim 1 wherein Z is selected from the group consisting of:
a cyclohexyl group optionally substituted by one or more substituents selected from alkyl, halo, alkoxy, CN, haloalkyl and OH;
a piperidin-3-yl group optionally substituted by one or more substituents selected from alkyl, halo, alkoxy, CN, haloalkyl and OH;
a piperidin-2-yl group optionally substituted by one or more substituents selected from alkyl, halo, alkoxy, CN, haloalkyl and OH;
a pyrrolidin-2-yl group optionally substituted by one or more substituents selected from alkyl, CN, halo, alkoxy, haloalkyl and OH; and
a pyrrolidin-3-yl group optionally substituted by one or more substituents selected from alkyl, CN, halo, alkoxy, haloalkyl and OH.

4. The compound of formula (I) according to claim 1 wherein $R_2$ is COOH.

5. The compound of formula (I) according to claim 1 wherein X—Y is NH—SO$_2$.

6. The compound of formula (I) according to claim 1 wherein $R_5$ is selected from alkyl, haloalkyl, SO$_2$-alkyl, Cl, alkoxy, OH, CN, hydroxyalkyl, alkylthio, heteroaryl, cycloalkyl, heterocycloalkyl and haloalkoxy.

7. The compound of formula (I) according to claim 1 wherein $R_5$ is selected from OMe, OEt, Me, Et, and cyclopropyl.

8. The compound of formula (I) according to claim 1 wherein R is selected from CN, haloalkyl, SO$_2$-alkyl, SO$_2$NR$_{16}$R$_{17}$, CONR$_{10}$R$_{11}$ and tetrazolyl.

9. The compound of formula (I) according to claim 1 wherein $R_7$ is selected from CF$_3$, CN, CONH$_2$, SO$_2$NH$_2$, 1H-1,2,3,4-tetrazol-1-yl and SO$_2$Me.

10. The compound of formula (I) according to claim 1 wherein $R_8$ is selected from H, Cl, F and Me.

11. The compound of formula (I) according to claim 1 wherein $R_1$, $R_3$, $R_4$, $R_6$, $R_8$ and $R_9$ are all H.

12. The compound of formula (I) according to claim 1 wherein:
$R_2$ is COOH;
X-Y is NH—SO$_2$;
$R_5$ is selected from cyclopropyl, OMe and Et;
$R_1$, $R_3$, $R_4$, $R_6$ and $R_9$ are all H;
$R_7$ is selected from CN, haloalkyl, heteroaryl and SO$_2$-alkyl;
$R_8$ is selected from H, Cl and F; and
Z is selected from the following:

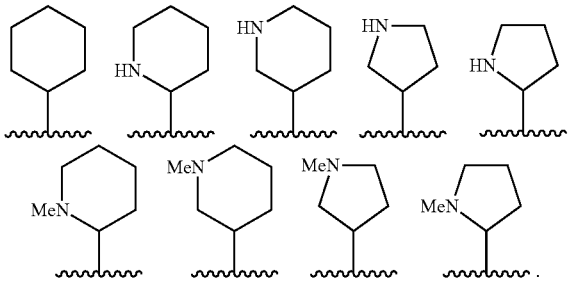

13. The compound according to claim 1 which is selected from the following:
(1)
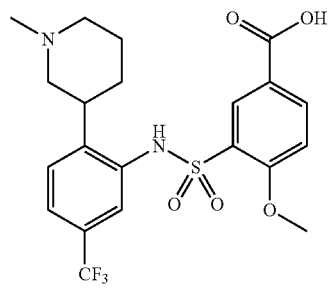
(2)
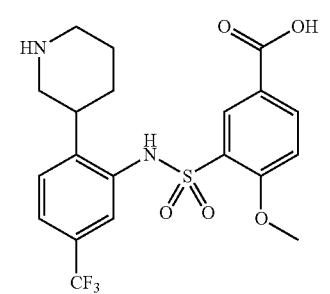
(3)
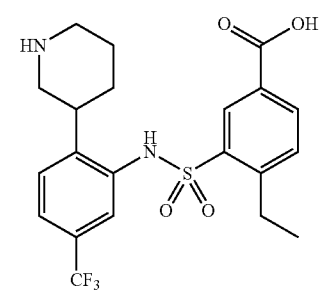
(4)
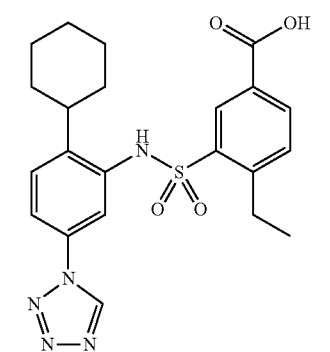
(5)
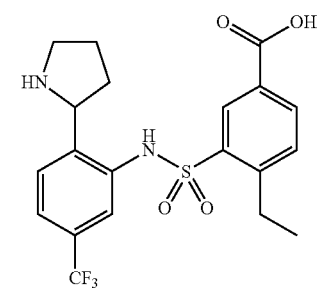
-continued
(6)
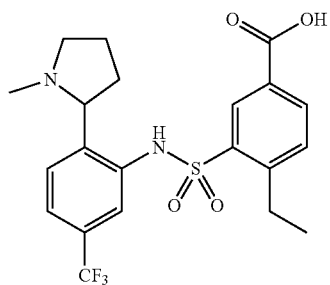
(7)
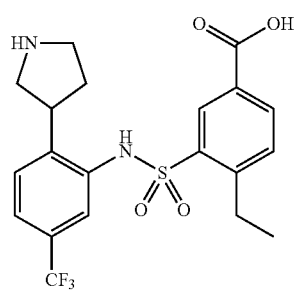
(8)
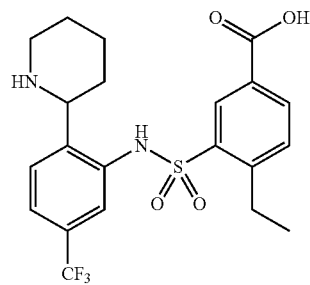
(9)
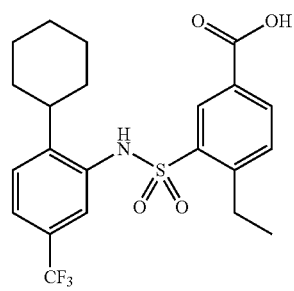
(10)
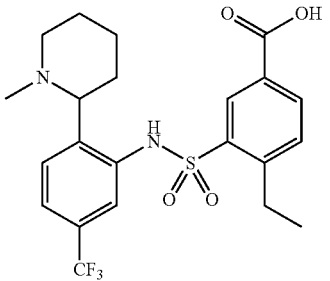

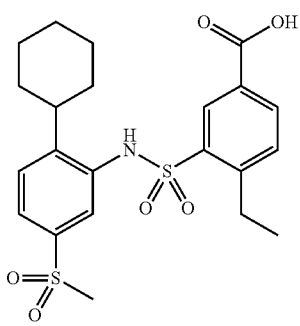 (11)
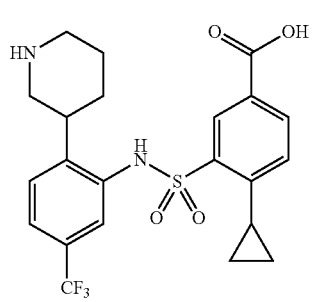 (12)
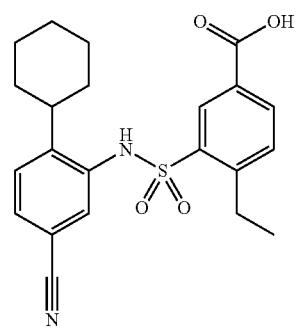 (13)
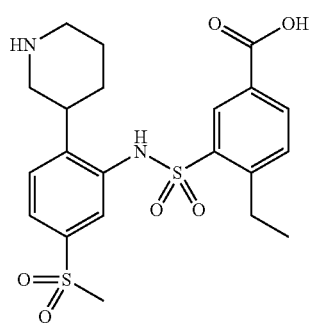 (14)
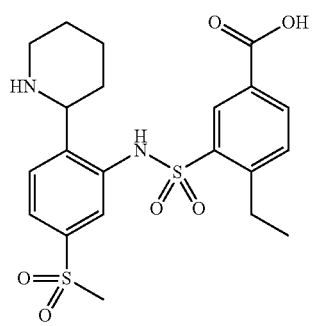 (15)
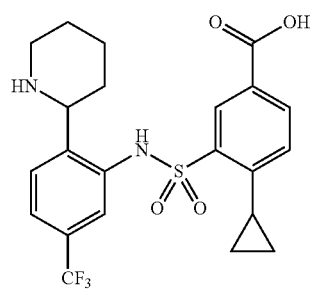 (16)
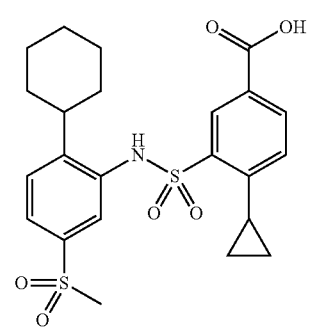 (17)
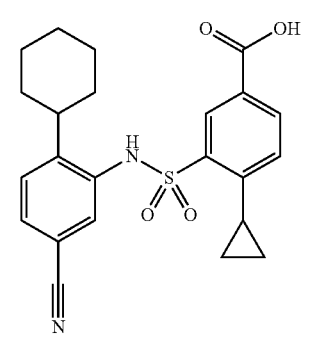 (18)
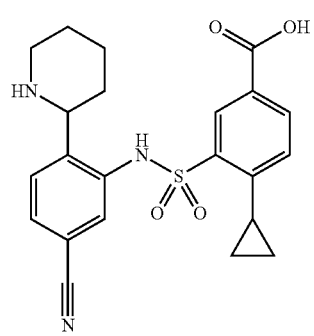 (19)
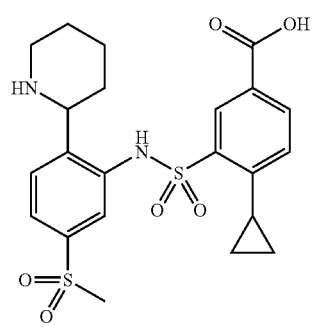 (20)

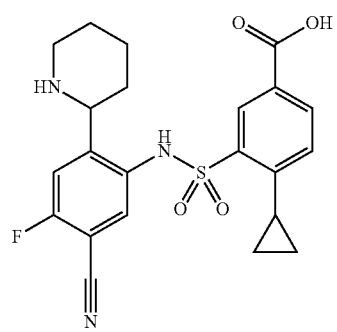
(21)
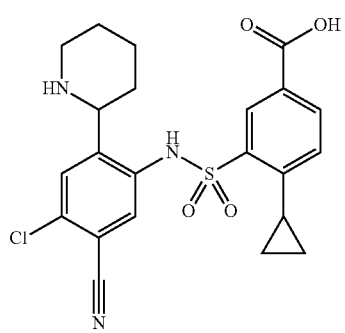
(22)
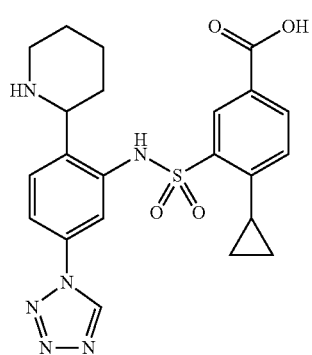
(23)
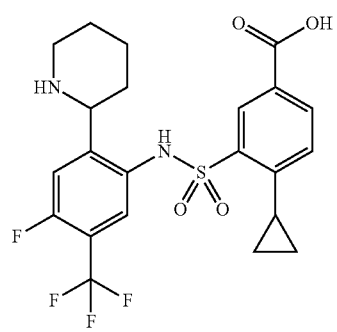
(24)
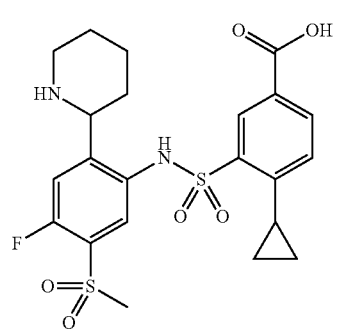
(25)
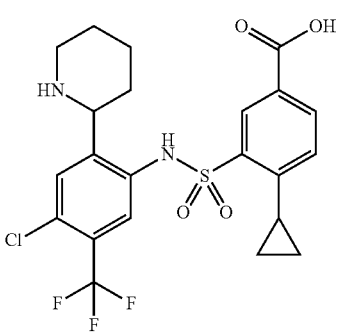
(26)
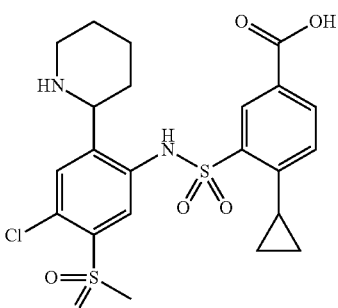
(27)
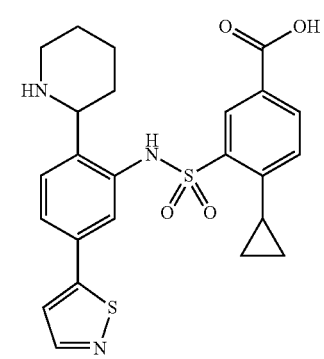
(28)
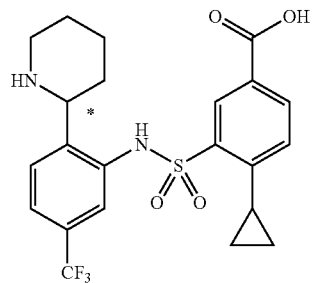
(29)E1
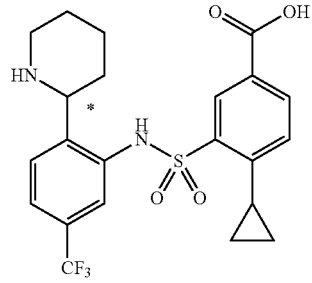
(30)E2

-continued (31)

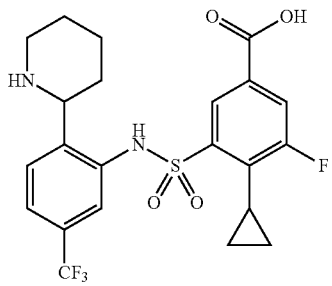

or a pharmaceutically acceptable salt or hydrate thereof.

14. A pharmaceutical composition comprising the compound of formula (I) as defined in claim 1 admixed with a pharmaceutically acceptable excipient, diluent or carrier, and optionally one or more additional active agents.

15. A combination comprising the compound according to claim 1 and a further active agent.

16. A method of treating a disorder selected from the group consisting of a proliferative disorder, an immune disorder, a viral disorder, and an inflammatory disorder in a subject, wherein the disorder is caused by, associated with or accompanied by abnormal ERAP1 activity, and wherein the method comprises administering to the subject a therapeutically effective amount of a compound of formula (I), or a pharmaceutically acceptable salt or hydrate thereof:

(1)

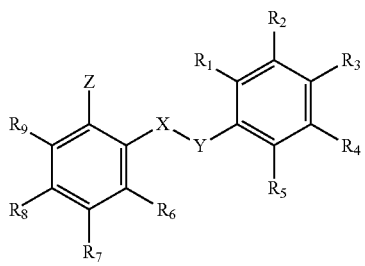

wherein:

Z is a group of formula:

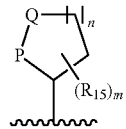

wherein P and Q are each independently $CR_{12}R_{13}$; or one of P and Q is $NR_{14}$ and the other is $CR_{12}R_{13}$;

the group X—Y is —NHSO$_2$— or —SO$_2$NH—;

$R_1$ is H, CN or alkyl;

$R_2$ is selected from COOH and a tetrazolyl group;

$R_3$ is selected from H, Cl and alkyl;

$R_4$ is selected from H and halo;

$R_5$ is selected from H, alkyl, haloalkyl, SO$_2$-alkyl, Cl, alkoxy, OH, CN, hydroxyalkyl, alkylthio, heteroaryl, cycloalkyl, heterocycloalkyl and haloalkoxy;

$R_6$ is H;

$R_7$ is selected from H, CN, haloalkyl, halo, SO$_2$-alkyl, heteroaryl, SO$_2$NR$_{16}$R$_{17}$, CONR$_{10}$R$_{11}$ and alkyl, wherein said heteroaryl group is optionally substituted by one or more substituents selected from alkyl, halo, alkoxy, CN, haloalkyl and OH;

$R_8$ is selected from H, alkyl, haloalkyl and halo;

$R_9$ is H or halo; and $R_{10}$, $R_{11}$, $R_{12}$, $R_{13}$, $R_{14}$, $R_{16}$ and $R_{17}$ are each independently H or alkyl;

$R_{15}$ is selected from alkyl, halo, alkoxy, CN, haloalkyl and OH; and m and n are each independently 0, 1, 2 or 3.

17. The method according to claim 16, wherein the compound modulates ERAP1.

18. The method according to claim 16, wherein the disorder is a proliferative disorder.

19. The method according to claim 16, wherein the disorder is cancer.

20. The method according to claim 16, wherein said compound is used in combination with an immunotherapy.

* * * * *

SEQUENCE LISTING

```
<160> NUMBER OF SEQ ID NOS: 4

<210> SEQ ID NO 1
<211> LENGTH: 10
<212> TYPE: PRT
<213> ORGANISM: Artificial Sequence
<220> FEATURE:
<223> OTHER INFORMATION: decapeptide substrate
<220> FEATURE:
<221> NAME/KEY: MISC_FEATURE
<222> LOCATION: (7)..(7)
<223> OTHER INFORMATION: dinitrophenyl maleimide (Dnp) residue labeling

<400> SEQUENCE: 1

Trp Arg Val Tyr Glu Lys Cys Ala Leu Lys
1               5                   10

<210> SEQ ID NO 2
<211> LENGTH: 8
<212> TYPE: PRT
<213> ORGANISM: Artificial Sequence
<220> FEATURE:
<223> OTHER INFORMATION: ovalbumin-specific peptide

<400> SEQUENCE: 2

Ser Ile Ile Asn Phe Glu Lys Leu
1               5

<210> SEQ ID NO 3
<211> LENGTH: 30
<212> TYPE: PRT
<213> ORGANISM: Artificial Sequence
<220> FEATURE:
<223> OTHER INFORMATION: ER-targeted N-terminally extended precursor
      peptide derived from ovalbumin

<400> SEQUENCE: 3

Met Arg Tyr Met Ile Leu Gly Leu Leu Ala Leu Ala Ala Val Cys Ser
1               5                   10                  15

Ala Ala Ile Val Met Lys Ser Ile Ile Asn Phe Glu His Leu
            20                  25                  30

<210> SEQ ID NO 4
<211> LENGTH: 8
<212> TYPE: PRT
<213> ORGANISM: Artificial Sequence
<220> FEATURE:
<223> OTHER INFORMATION: specific recognition complex peptide sequence
```

```
<400> SEQUENCE: 4

Ser Ile Ile Asn Phe Glu His Leu
1               5
```